US011370775B2

United States Patent
Tseng et al.

(10) Patent No.: US 11,370,775 B2
(45) Date of Patent: Jun. 28, 2022

(54) SUBSTITUTED BENZIMIDAZOLE DERIVATIVES AS D-AMINO ACID OXIDASE (DAAO) INHIBITORS

(71) Applicants: NATIONAL TAIWAN UNIVERSITY, Taipei (TW); NATIONAL YANG MING CHIAO TUNG UNIVERSITY, Hsinchu (TW); NATIONAL HEALTH RESEARCH INSTITUTES, Miaoli County (TW); Yufeng Jane Tseng, Stafford, VA (US)

(72) Inventors: Yufeng Jane Tseng, Stafford, VA (US); Yu-Li Liu, Miaoli County (TW); Chung-Ming Sun, Hsinchu (TW); Wen-Sung Lai, Taipei (TW); Chih-Min Liu, Taipei (TW); Hai-Gwo Hwu, Taipei (TW)

(73) Assignees: Yufeng Jane Tseng, Stafford, VA (US); NATIONAL TAIWAN UNIVERSITY, Taipei (TW); NATIONAL YANG MING CHIAO TUNG UNIVERSITY, Hsinchu (TW); NATIONAL HEALTH RESEARCH INSTITUTES, Miaoli County (TW)

( * ) Notice: Subject to any disclaimer, the term of this patent is extended or adjusted under 35 U.S.C. 154(b) by 140 days.

(21) Appl. No.: 16/332,628

(22) PCT Filed: Sep. 14, 2017

(86) PCT No.: PCT/US2017/051610
§ 371 (c)(1),
(2) Date: Mar. 12, 2019

(87) PCT Pub. No.: WO2018/053161
PCT Pub. Date: Mar. 22, 2018

(65) Prior Publication Data
US 2020/0361894 A1 Nov. 19, 2020

Related U.S. Application Data

(60) Provisional application No. 62/394,479, filed on Sep. 14, 2016.

(51) Int. Cl.
C07D 401/12 (2006.01)
C07D 401/14 (2006.01)
C07D 405/14 (2006.01)
C07D 409/14 (2006.01)
C07D 413/14 (2006.01)
A61P 25/18 (2006.01)

(52) U.S. Cl.
CPC ............ C07D 401/12 (2013.01); A61P 25/18 (2018.01); C07D 401/14 (2013.01); C07D 405/14 (2013.01); C07D 409/14 (2013.01); C07D 413/14 (2013.01)

(58) Field of Classification Search
CPC .................................................. C07D 401/14
See application file for complete search history.

(56) References Cited

U.S. PATENT DOCUMENTS

| | | |
|---|---|---|
| 5,373,018 A | 12/1994 | Cugola et al. |
| 5,374,649 A | 12/1994 | Cugola et al. |
| 5,686,461 A | 11/1997 | Cugola et al. |
| 5,962,496 A | 10/1999 | Cugola et al. |
| 6,100,289 A | 8/2000 | Cugola et al. |
| 2008/0146564 A1 | 6/2008 | Bonfanti et al. |
| 2014/0194386 A1 | 7/2014 | Burns et al. |

FOREIGN PATENT DOCUMENTS

| | | |
|---|---|---|
| EP | 0198208 A1 | 10/1986 |
| EP | 0396124 A2 | 11/1990 |
| JP | 2008-533103 A | 8/2008 |
| JP | 2016-506419 A | 3/2016 |
| WO | 2003039540 A2 | 5/2003 |
| WO | 2005089753 A2 | 9/2005 |
| WO | 2007/133983 A2 | 11/2007 |
| WO | 2010042785 A1 | 4/2010 |
| WO | 2015168346 A1 | 5/2015 |

OTHER PUBLICATIONS

CA Registry No. 1923077-96-6, entered into CA Registry File on Jun. 2, 2016,supplied by Aurora Fine Chemicals. (Year: 2016).*
Aurora Product Guide, 1 page,retrieved from the Internet at http://www.aurorafinechemicals.com/about.html on Apr. 28, 2015. (Year: 2015 ).*
Roesner et al. Chemical Abstracts vol. 106, No. 5044 (Abstract for EP 198208 Oct. 22, 86). (Year: 1987).*
CA Registry No. 1989498-52-3, entered into CA Registry File on Sep. 8, 2016,supplied by Aurora Fine Chemicals. (Year: 2016).*
International Search Report in International Patent Application No. PCT/US2017/051610, dated Dec. 22, 2017, in 4 pages.

(Continued)

Primary Examiner — Erich A Leeser
(74) Attorney, Agent, or Firm — Duane Morris LLP

(57) ABSTRACT

The present invention provides novel substituted benzimidazole derivatives of formula (I) used as DAAO inhibitors and for treatment and/or prevention of neurological disorders.

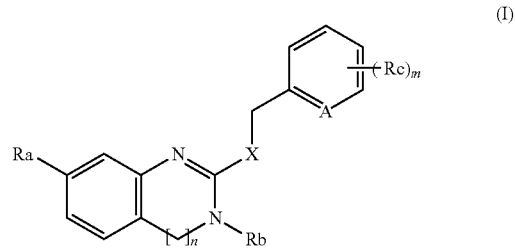

10 Claims, 3 Drawing Sheets

(56) References Cited

OTHER PUBLICATIONS

Chemical Abstract Compound, STN express, RNs 1501768-59-7 (Entered STN: Dec. 23, 2013), 1393593-13-9 (Entered STN: Sep. 5, 2012), 943423-66-3 (Entered STN: Jul. 26, 2007), 927151-47-1 (Entered STN: Mar. 18, 2007), 487033-13-6 (Entered STN: Feb. 7, 2003), 351192-79-5 (Entered STN: Aug. 13, 2001).
Chemical Abstract Compound, STN express, RN 1784175-58-1 (Entered STN: Jun. 19, 2015).
Oguri, Shigeyuki, et al. "Screening of D-amino acid oxidase inhibitor by a new multi-assay method." Food chemistry 100.2 (2007): 616-622.
Brandish, Philip E., et al. "A cell-based ultra-high-throughput screening assay for identifying inhibitors of D-amino acid oxidase." Journal of biomolecular screening 11.5 (2006): 481-487.
Chemical Abstract Compound, STN express, RNs 924815-36-1, 924806-17-7, 924765-23-1, 924757-75-5, 924732-12-7 (Entered STN: Mar. 5, 2007), 924614-51-7, 924588-10-3 (Entered STN: Mar. 4, 2007), 924520-11-6, 924512-11-8, 924495-21-6 (Entered STN: Mar. 2, 2007), 923544-81-4 (Entered STN: Feb. 27, 2007), 880273-86-9 (Entered STN: Apr. 13, 2006).
Office Action in Japan Counterpart Application No. 2019-513382, dated Oct. 6, 2020, in 3 pages; English translation provided.
Paramashivappa, R., et al. "Design, synthesis and biological evaluation of benzimidazole/benzothiazole and benzoxazole derivatives as cyclooxygenase inhibitors." Bioorganic & Medicinal Chemistry Letters 13.4 (2003): 657-660.
Andrews, Stephen P., et al. "Automated parallel, multi-step polymer-assisted solution phase (PASP) synthesis of substituted benzimidazole derivatives." Combinatorial Chemistry & High Throughput Screening 7.2 (2004): 163-178.
Vickerstaffe, Emma, et al. "A Highly Automated, Polymer-Assisted Strategy for the Preparation of 2-Alkylthiobenzimidazoles and N, N'-Dialkylbenzimidazolin-2-ones." Journal of Combinatorial Chemistry 7.3 (2005): 385-397.
Carlton, David L., et al. "Discovery of small molecule agonists for the bombesin receptor subtype 3 (BRS-3) based on an omeprazole lead." Bioorganic & Medicinal Chemistry Letters 18.20 (2008): 5451-5455.
Foti, Robert S., et al. "Ligand-based design of a potent and selective inhibitor of cytochrome P450 2C19." Journal of Medicinal Chemistry 55.3 (2012): 1205-1214.
Office Action in Korean Counterpart Application No. 10-2019-7010035, dated Dec. 4, 2020, in 15 pages; English translation provided.
Wu, Cheng-Yi, and Chung-Ming Sun. "Soluble polymer-supported synthesis of 2-(arylamino) benzimidazoles." Tetrahedron Letters 43.8 (2002): 1529-1533.
Chemical Abstract Compound, STN, RN 145326-41-6, (Entered STN: Jan. 14, 1993.).
Chemical Abstract Compound, STN, RN 1784175-58-1, (Entered STN: Jun. 19, 2015.).

* cited by examiner ered the NMDA receptor as a co-agonist. This in turn may regulate the NMDA receptor in opening its calcium channel. D-serine has been found to inhibit the α-amino-3-hydroxy-5-methyl-4-isoxazole propionic acid (AMPA) receptor-mediated current in rat hippocampus neurons.
SUBSTITUTED BENZIMIDAZOLE DERIVATIVES AS D-AMINO ACID OXIDASE (DAAO) INHIBITORS

CROSS-REFERENCE TO RELATED APPLICATION

This application is a § 371 national stage entry of International Application No. PCT/US17/51610, filed Sep. 14, 2017, which claims the benefit of U.S. Provisional Application Ser. No. 62/394,479, filed on Sep. 14, 2016, the entire disclosures of which are incorporated herein by reference in their entireties.

FIELD OF THE INVENTION

The invention relates to D-amino acid oxidase (DAAO) inhibitors. Particularly, the present invention provides novel substituted benzimidazole derivatives used as DAAO inhibitors and for treatment and/or prevention of neurological disorders.

BACKGROUND OF THE INVENTION

The aberrant regulatory mechanism of glutamate transmission on N-methyl-D-aspartic acid (NMDA) receptor has been reported as one of the neuropathology in schizophrenia. The receptor is a heterotetramer composed of two structure subunits of NMDA receptor 1 (NR1) and NR2. Modulation of the glycine binding site of NMDA receptor may improve the cognitive function and negative symptoms in schizophrenia. D-amino acid oxidase (DAAO) was found to be involved in the activation process of the NMDA receptor. The substrates of DAAO, especially the D-serine, may bind to the glycine site of the NMDA receptor as a co-agonist. This in turn may regulate the NMDA receptor in opening its calcium channel. D-serine has been found to inhibit the α-amino-3-hydroxy-5-methyl-4-isoxazole propionic acid (AMPA) receptor-mediated current in rat hippocampus neurons.

Accordingly, there is a need to develop candidate drugs having DAAO inhibitory effect to treat various neurological and physical disorder.

SUMMARY OF THE INVENTION

The present invention pertains to a list of substituted benzimidazole derivatives used as DAAO inhibitors and for treatment and/or prevention of neurological disorders.

The present invention provides a compound having the following formula (I), wherein each substituent is described herein.

The present invention also provides a pharmaceutical composition comprising a compound of the present invention.

The present invention also provides a method of inhibiting a DAAO comprising contacting a cell with a compound of the present invention.

The present invention also provides a method of treating or preventing the disease associated with DAAO dysregulation in a subject comprising administrating an effective amount of a compound of the present invention to the subject.

In some embodiments, the disease is symptom domains of schizophrenia and schizoaffective disorder, depression, Tourette Syndrome, Post-traumatic stress disorder (PTSD), Obsessive-compulsive disorder (OCD), analgesics, loss of memory and/or cognition associated with neurodegenerative diseases or loss of neuronal function characteristic of neurodegenerative diseases. Certain embodiments include mild cognitive impairment (MCI), Alzheimer's disease, Parkinson's disease and schizophrenia.

DETAILED DESCRIPTION OF THE INVENTION

Figure 1:
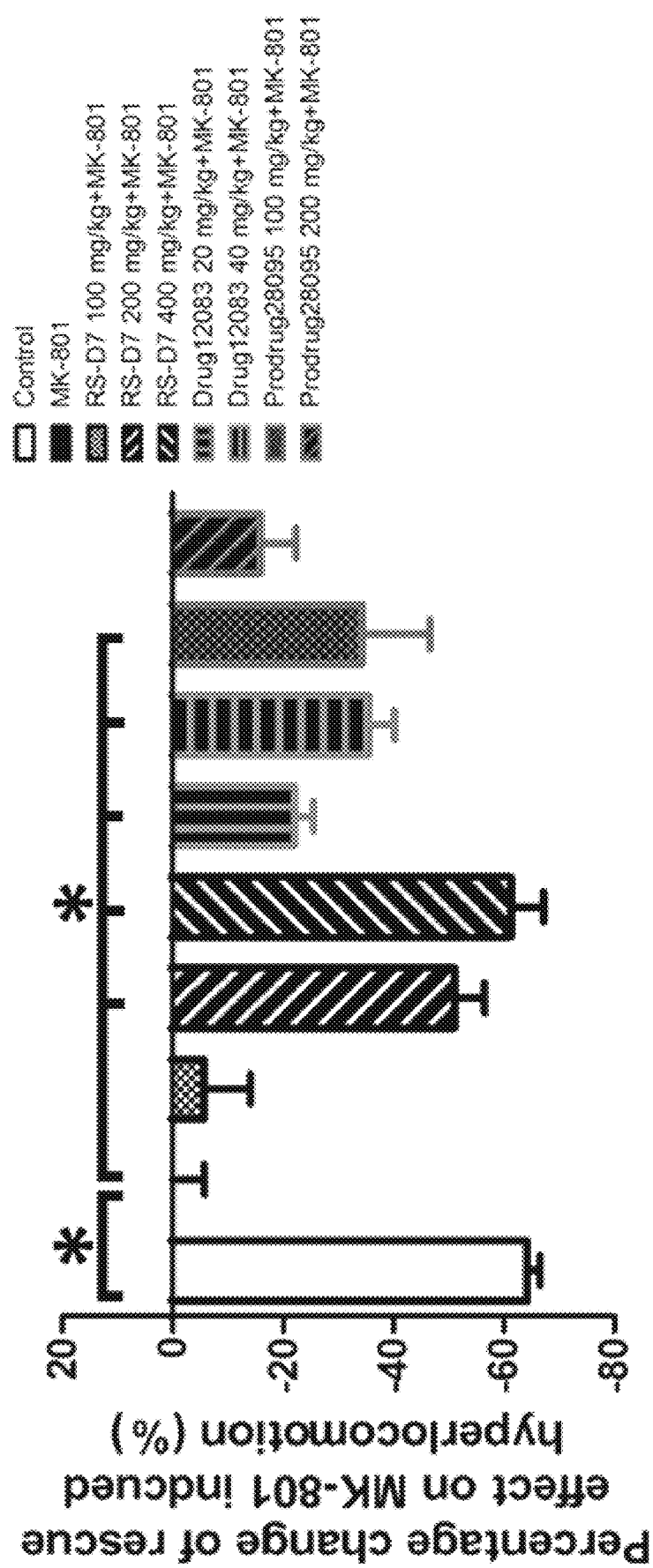
FIG. 1 shows that compared to the MK-801 group, different dosages of RS-D7, Drug 12083 and Prodrug 28095 can rescue the MK-801-induced hyperlocomotion.

Accordingly, DAAO was hypothesized to be implicated in the pathogenesis of schizophrenia. As the NMDA receptor also involved in affective disorder, it is likely that inhibiting the DAAO may elevate the function of NMDA and improve both the symptoms of schizophrenia and depression affective disorder.

Known inhibitors of DAAO include benzoic acid, pyrrole-2-carboxylic acids, and indole-2-carboxylic acids. Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. U.S. Pat. Nos. 5,373,018; 5,374,649; 5,686,461; 5,962,496 and 6,100,289 disclose treatment of neurotoxic injury and neurodegenerative disease using indole derivatives. WO 03/039540 disclose DAAO inhibitors, including indole-2-carboxylic acids, and methods of enhancing learning, memory and cognition as well as methods for treating neurodegenerative disorders. Patent Application No. WO/2005/089753 discloses benzisoxazole analogs and methods of treating mental disorders, such as Schizophrenia. WO/2015/168346 discloses a list of known known compounds as DAAO inhibitors.

As used herein and in the appended claims, the singular forms "a," "and," and "the" include plural referents unless the context clearly dictates otherwise. When ranges are used herein for physical properties, such as molecular weight, or chemical properties, such as chemical formulae, all combinations and subcombinations of ranges and specific embodiments therein are intended to be included. The term "or" refers to "and/or" unless explicitly indicated to refer to alternatives only or unless the alternatives are mutually exclusive. The term "about" when referring to a number or a numerical range means that the number or numerical range referred to is an approximation within experimental variability (or within statistical experimental error). The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{10}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_6$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless specifically stated otherwise in the specification, an alkyl group is optionally substituted by one or more of substituents.

"Alkoxy" refers to a radical bonded through an oxygen atom of the formula —O— alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless specifically stated otherwise in the specification, an alkenyl group is optionally substituted by one or more of substituents.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless specifically stated otherwise in the specification, an alkynyl group is optionally substituted by one or more of substituents.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) pi-electron system in accordance with the Huckel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, $R^b$—C(O)$R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$) C(O)$R^a$, —$R^b$—N($R^a$)S(O)$_t R^a$ (where t is 1 or 2), —$R^b$—S(O)$_t OR^a$ (where t is 1 or 2), —$R^b$—S(O).sub.$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R.sup.b is independently a direct bond or a straight or branched alkylene or alkenylene chain, and R.sup.c is a straight or branched alkylene or alkenylene chain, and where each of the above substituents is unsubstituted unless otherwise indicated.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) pi-electron system in accordance with the Huckel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo [b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c] pyridinyl, 5,6,7,8,9,10-hexahydrocycloocta[d]pyrimidinyl, 5,6,7,8,9,10-hexahydrocycloocta[d]pyridazinyl, 5,6,7,8,9, 10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d] pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno [2,3-d]pyrimidinyl, 6,7,8,9-tetrahydro-5H-cyclohepta[4,5] thieno[2,3-d]pyrimidinyl, 5,6,7,8-tetrahydropyrido[4,5-c] pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R$—$C(O)N(R^a)_2$, —$R^b$—$N(R^a)C(O)OR^a$, —$R^b$—$N(R^a)$ $C(O)R^a$, —$R^b$—$N(R^a)S(O)_tR^a$ (where t is 1 or 2), —$R^b$—$S(O)_tOR^a$ (where t is 1 or 2), —$R^b$—$S(O).sub_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R.sup.b is independently a direct bond or a straight or branched alkylene or alkenylene chain, and R.sup.c is a straight or branched alkylene or alkenylene chain, and where each of the above substituents is unsubstituted unless otherwise indicated.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups that may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredient of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "prevent," "prevention" or "preventing" means inhibition or averting of symptoms associated with the target disease.

The phrase "therapeutically effective amount" refers to that amount of a compound, material, or composition comprising a compound of the present invention which is effective for producing a desired therapeutic effect, at a reasonable benefit/risk ratio applicable to any medical treatment.

The term "neurological disorder" refers to any undesirable condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any undesirable condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

Compounds of the Present Invention

In one aspect, the present invention provides a compound of formula (I):

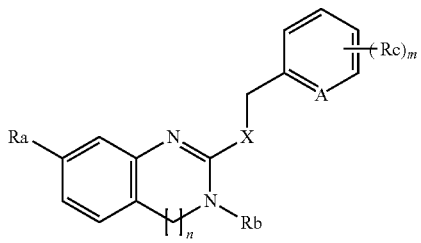
(I)

wherein n is 0 or 1,
X is —S—, —S(=O)— or —NR$_n$—; wherein
R$_n$ is H or

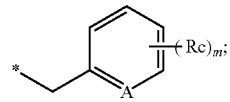

A is —CH, —CR$_c$ or N;
R$_a$ is —C(=O)OR$_{a1}$, —OR$_{a2}$, —O—C(=O)R$_{a3}$ or —O—C(=O)-T-OR$_{a4}$; wherein
R$_{a1}$ is H or linear or branched C$_{1-15}$alkyl;
R$_{a2}$ is H, linear or branched C$_{1-15}$alkyl, phosphonate, diarylphosphonate or an O-protecting group;
R$_{a3}$ and R$_{a4}$ are independently a protecting group, linear or branched C$_{1-15}$alkyl, linear or branched C$_{2-15}$alkenyl, -T-C$_{3-10}$cycloalkyl, -T-NHR$_{a3p}$, -T-C$_{3-10}$cycloalkenyl, -T-C$_{6-10}$aryl, -T-C$_{5-10}$heteroaryl, -T-NH—C(=O)—O—C$_{1-10}$alkyl, -T-adamantyl or —C$_{1-3}$alkylene-C$_{6-10}$aryl where the alkylene is substituted with -T-NHR$_{a3p}$;
R$_{a3p}$ is H or an N-protecting group;
R$_b$ is H, linear or branched C$_{1-15}$alkyl, linear or branched C$_{2-15}$alkenyl, C$_{1-3}$alkoxy-C$_{1-15}$alkyl-, -T'-C$_{3-10}$cycloalkyl, -T'-C$_{3-10}$cycloalkenyl, -T'-C$_{6-10}$ aryl or -T'-C$_{5-10}$heteroaryl;
R$_c$ each is independently linear or branched C$_{1-15}$alkyl, linear or branched C$_{1-15}$alkoxyl, unprotected or protected hydroxyl group, or —C$_{1-10}$alkylene-Y—C$_{6-10}$heteroaryl wherein —Y— is —CH$_2$—, —NH—, —O— or —S—;
symbol * represents the bonding position;
m is an integer from 0 to 4;
-T- is absent, C$_{1-3}$alkylene or C$_{2-3}$alkenylene;
-T'- is C$_{1-3}$alkylene or C$_{2-3}$alkenylene; and
wherein the heteroaryl contains at least one heteroatom, each heteroatom being independently S, N or O;
wherein the alkyl, alkenyl, alkoxy, cycloalkyl, aryl, heteroaryl, alkylene and alkenylene are each independently unsubstituted or substituted with at least one substituent;
wherein the substituent is each independently a halogen, a protecting group, protected or unprotected amino group, nitro, nitroso, linear or branched C$_{1-15}$ alkyl, or linear or branched C$_{1-15}$ alkoxy or C$_{3-10}$cycloalkyl; and
when R$_b$ is H, the tautomers are included,
with the proviso that
when X is —S— or —S(=O)—, R$_a$ is —OR$_{a2}$ and R$_{a2}$ is H or linear or branched C$_{1-15}$alkyl, then A is —CH or —CR$_c$;

when X is —S— or —S(=O)— and R$_a$ is —C(=O)OR$_{a1}$, R$_b$ is linear or branched C$_{6-15}$alkyl, linear or branched C$_{6-15}$alkenyl, C$_{1-3}$alkoxy-C$_{1-15}$alkyl-, -T'-C$_{3-10}$cycloalkyl, -T'-C$_{3-10}$cycloalkenyl, -T'-C$_{6-10}$ aryl or -T'-C$_{5-10}$heteroaryl;
or a pharmaceutically acceptable salt thereof.

In one embodiment, the present invention provides a compound of formula (I-a):
wherein n is 0 or 1,

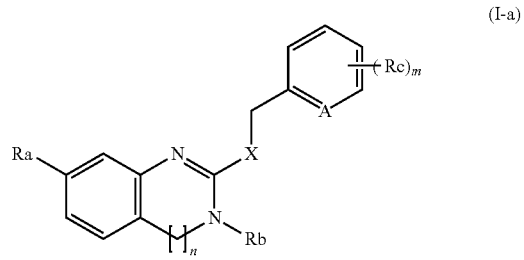
(I-a)

X is —S—, —S(=O)— or —NR$_n$—; wherein
R$_n$ is H or

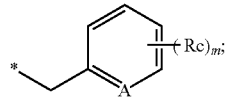

A is —CH, —CR$_c$ or N;
R$_a$ is —C(=O)OR$_{a1}$, —OR$_{a2}$, —O—C(=O)R$_{a3}$ or —O—C(=O)-T-OR$_{a4}$; wherein
R$_{a1}$ is H or linear or branched C$_{1-15}$alkyl;
R$_{a2}$ is H, linear or branched C$_{1-15}$alkyl, diarylphosphonate or an O-protecting group;
R$_{a3}$ and R$_{a4}$ are independently a protecting group, linear or branched C$_{1-15}$alkyl, linear or branched C$_{2-15}$alkenyl, -T-C$_{3-10}$cycloalkyl, -T-NHR$_{a3p}$, -T-C$_{3-10}$cycloalkenyl, -T-C$_{6-10}$aryl, -T-C$_{5-10}$heteroaryl, -T-NH—C(=O)—O—C$_{1-10}$alkyl or -T-adamantyl;
R$_{a3p}$ is H or an N-protecting group;
R$_b$ is H, linear or branched C$_{1-15}$alkyl, linear or branched C$_{2-15}$alkenyl, C$_{1-3}$alkoxy-C$_{1-15}$alkyl-, -T'-C$_{3-10}$cycloalkyl, -T'-C$_{3-10}$cycloalkenyl, -T'-C$_{6-10}$ aryl or -T'-C$_{5-10}$heteroaryl;
R$_c$ each is independently linear or branched C$_{1-15}$alkyl, linear or branched C$_{1-15}$alkoxyl, unprotected or protected hydroxyl group, or —C$_{1-10}$alkylene-Y—C$_{6-10}$heteroaryl wherein —Y— is —CH$_2$—, —NH—, —O— or —S—;
symbol * represents the bonding position;
m is an integer from 0 to 4;
-T- is absent, C$_{1-3}$alkylene or C$_{2-3}$alkenylene;
-T'- is C$_{1-3}$alkylene or C$_{2-3}$alkenylene; and
wherein the heteroaryl contains at least one heteroatom, each heteroatom being independently S, N or O;
wherein the alkyl, alkenyl, alkoxy, cycloalkyl, aryl, heteroaryl, alkylene and alkenylene are each independently unsubstituted or substituted with at least one substituent;
wherein the substituent is each independently a halogen, a protecting group, protected or unprotected amino group, nitro, nitroso, linear or branched C$_{1-15}$ alkyl, linear or branched C$_{1-15}$ alkoxy or C$_{3-10}$cycloalkyl and when $R_b$ is H, the tautomers are included,
with the proviso that
when X is —S— or —S(=O)—, $R_a$ is —$OR_{a2}$ and $R_{a2}$ is H or linear or branched $C_{1-15}$alkyl, then A is —CH or —$CR_c$;
when X is —S— or —S(=O)— and $R_a$ is —C(=O)$OR_{a1}$, $R_b$ is linear or branched $C_{6-15}$alkyl, linear or branched $C_{6-15}$alkenyl, $C_{1-3}$alkoxy-$C_{1-15}$alkyl-, -T'-$C_{3-10}$cycloalkyl, -T'-$C_{3-10}$cycloalkenyl, -T'-$C_{6-10}$ aryl or -T'-$C_{5-10}$heteroaryl;
or a pharmaceutically acceptable salt thereof.

In one embodiment, the present invention provides a compound of formula (I-b),

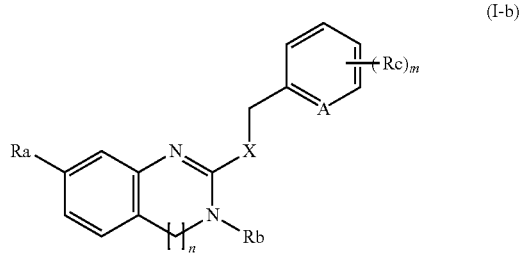

(I-b)

wherein n is 0 or 1,
X is —S—, —S(=O)— or —$NR_n$—;
$R_n$ is H or

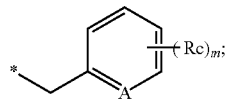

A is —CH, —$CR_c$ or N;
$R_a$ is —C(=O)$OR_{a1}$, —$OR_{a2}$ or —O—C(=O)$R_{a3}$;
wherein
$R_{a1}$ is H or linear or branched $C_{1-15}$alkyl;
$R_{a2}$ is H, linear or branched $C_{1-15}$alkyl, phosphonate, diarylphosphonate or an O-protecting group;
$R_{a3}$ is -T-$NHR_{a3p}$, -T-NH—C(=O)—O—$C_{1-10}$alkyl or —$C_{1-3}$alkylene-$C_{6-10}$aryl where the alkylene is substituted with -T-$NHR_{a3p}$;
$R_{a3p}$ is H or an N-protecting group;
$R_b$ is H, linear or branched $C_{1-15}$alkyl, $C_{1-3}$alkoxy-$C_{1-10}$alkyl-, -T'-$C_{3-10}$ cycloalkyl, -T'-$C_{3-10}$cycloalkenyl, -T'-$C_{6-10}$ aryl or -T'-$C_{5-10}$ heteroaryl;
$R_c$ each is independently linear or branched $C_{1-15}$alkyl, linear or branched $C_{1-15}$alkoxyl, unprotected or protected hydroxyl group or —$C_{1-10}$alkylene-Y—$C_{6-10}$heteroaryl wherein —Y— is —$CH_2$—, —NH—, —O— or —S—;
symbol * represents the bonding position;
m is an integer from 0 to 4;
-T- is absent, $C_{1-3}$alkylene or $C_{2-3}$alkenylene;
-T'- is $C_{1-3}$alkylene; and
wherein the heteroaryl contains at least one heteroatom, each heteroatom being independently S, N or O;
wherein the alkyl, alkenyl, alkoxy, cycloalkyl, aryl and heteroaryl are each independently unsubstituted or substituted with at least one substituent;
wherein the substituent is each independently a halogen, protected or unprotected amino group, nitro, nitroso, linear or branched $C_{1-15}$ alkyl, linear or branched $C_{1-15}$ alkoxy or $C_{3-10}$cycloalkyl; and when $R_b$ is H, the tautomers are included, with the proviso that
when X is —S— or —S(=O)—, $R_a$ is —$OR_{a2}$ and $R_{a2}$ is H or linear or branched $C_{1-15}$alkyl, then A is-CH or —$CR_c$;
when X is —S— or —S(=O)— and $R_a$ is —C(=O)$OR_{a1}$, $R_b$ is linear or branched $C_{6-15}$alkyl, linear or branched $C_{6-15}$alkenyl, $C_{1-3}$alkoxy-$C_{1-15}$alkyl-, -T'-$C_{3-10}$cycloalkyl, -T'-$C_{3-10}$cycloalkenyl, -T'-$C_{6-10}$ aryl or -T'-$C_{5-10}$heteroaryl;
or a pharmaceutically acceptable salt thereof.

In one embodiment, the present invention provides the compound of formula (I),
wherein n is 0 or 1;
X is —S—, —S(=O)— or —NR—; wherein
$R_n$ is H or

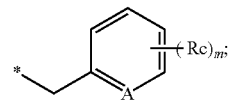

A is —CH, —$CR_c$ or N;
$R_a$ is —$OR_{a2}$, —O—C(=O)$R_{a3}$ or —O—C(=O)-T-$OR_{a4}$;
wherein
$R_{a2}$ is H, linear or branched $C_{1-15}$alkyl, phosphonate, diarylphosphonate or an O-protecting group;
$R_{a3}$ and $R_{a4}$ are independently a protecting group, linear or branched $C_{1-15}$alkyl, linear or branched $C_{2-15}$alkenyl, -T-$C_{3-10}$cycloalkyl, -T-$NHR_{a3p}$, -T-$C_{3-10}$cycloalkenyl, -T-$C_{6-10}$aryl, -T-$C_{5-10}$heteroaryl, -T-NH—C(=O)—O—$C_{1-10}$alkyl, -T-adamantyl or —$C_{1-3}$alkylene-$C_{6-10}$aryl where the alkylene is substituted with -T-$NHR_{a3p}$;
$R_{a3p}$ is H or an N-protecting group;
$R_b$ is H, linear or branched $C_{1-15}$alkyl, linear or branched $C_{2-15}$alkenyl, $C_{1-3}$alkoxy-$C_{1-5}$alkyl-, -T'-$C_{3-10}$cycloalkyl, -T'-$C_{3-10}$cycloalkenyl, -T'-$C_{6-10}$ aryl or -T'-$C_{5-10}$heteroaryl;
$R_c$ each is independently linear or branched $C_{1-15}$alkyl, linear or branched $C_{1-15}$alkoxyl, unprotected or protected hydroxyl group, or —$C_{1-10}$alkylene-Y—$C_{6-10}$heteroaryl wherein —Y— is —$CH_2$—, —NH—, —O— or —S—;
symbol * represents the bonding position;
m is an integer from 0 to 4;
-T- is absent, $C_{1-3}$alkylene or $C_{2-3}$alkenylene;
-T'- is $C_{1-3}$alkylene or $C_{2-3}$alkenylene; and
wherein the heteroaryl contains at least one heteroatom, each heteroatom being independently S, N or O;
wherein the alkyl, alkenyl, alkoxy, cycloalkyl, aryl, heteroaryl, alkylene and alkenylene are each independently unsubstituted or substituted with at least one substituent;
wherein the substituent is each independently a halogen, a protecting group, protected or unprotected amino group, nitro, nitroso, linear or branched $C_{1-15}$ alkyl, or linear or branched $C_{1-15}$ alkoxy or $C_{3-10}$cycloalkyl; and
when $R_b$ is H, the tautomers are included,
with the proviso that
when X is —S— or —S(=O)—, $R_a$ is —$OR_{a2}$ and $R_{a2}$ is H or linear or branched $C_{1-15}$alkyl, then A is —CH or —$CR_c$;
or a pharmaceutically acceptable salt thereof.

In a further embodiment, the present invention provides the compound of formula (I), wherein
n is 0;
X is —S(=O)—;
A is N;

$R_a$ is —$OR_{a2}$, —O—C(=O)$R_{a3}$ or —O—C(=O)-T-OR$_{a4}$, wherein $R_{a2}$ is H, linear or branched $C_{1-15}$alkyl, phosphonate, diarylphosphonate or an O-protecting group;

$R_{a3}$ and $R_{a4}$ are independently a protecting group, linear or branched $C_{1-15}$alkyl, linear or branched $C_{2-15}$alkenyl, -T-$C_{3-10}$cycloalkyl, -T-NHR$_{a3p}$, -T-$C_{3-10}$cycloalkenyl, -T-$C_{6-10}$aryl, -T-$C_{5-10}$heteroaryl, -T-NH—C(=O)—O—$C_{1-10}$alkyl, -T-adamantyl or —$C_{1-3}$alkylene-$C_{6-10}$aryl where the alkylene is substituted with -T-NHR$_{a3p}$; R$_{a3p}$ is H or an N-protecting group;

$R_b$ is H;

m is 3; and $R_c$ each is independently linear or branched $C_{1-15}$alkyl, linear or branched $C_{1-15}$alkoxyl;

or a pharmaceutically acceptable salt thereof.

In one embodiment, n is 0.

In one embodiment, m is an integer from 0 to 3.

In some embodiments, $R_a$ is —C(=O)OH, —C(=O)OC$_{1-4}$alkyl, H, —OR$_{a2}$ wherein $R_{a2}$ is H, linear or branched $C_{1-10}$alkyl or an O-protecting group; —O—C(=O)R$_{a3}$ wherein $R_{a3}$ is independently tert-butyl protecting group; linear or branched $C_{1-10}$alkyl unsubstituted or substituted by halogen, tert-butyl protecting group or protected amino group; linear or branched $C_{2-10}$alkenyl; $C_{1-4}$alkoxy; $C_{3-10}$cycloalkyl; —$C_{1-3}$alkylene-$C_{3-10}$cycloalkyl; —$C_{3-10}$cycloalkenyl; —$C_{6-10}$aryl unsubstituted or substituted by $C_{1-10}$ alkyl, nitro, $C_{1-15}$alkoxy or halogen; —$C_{5-10}$heteroaryl unsubstituted or substituted by $C_{1-10}$alkoxy; $C_{2-3}$alkenylene-$C_{6-10}$aryl wherein $C_{6-10}$aryl is unsubstituted or substituted by halogen; —$C_{1-3}$alkylene-NH—C(=O)—O—$C_{1-10}$alkyl; or adamantyl; or —O—C(=O)—O—$C_{1-10}$alkyl.

In some embodiments, $R_a$ is —O—$C_{1-10}$alkyl; —O-protecting group or —O—C(=O)R$_{a3}$ wherein $R_{a3}$ is a tert-butyl protecting group; adamantyl; linear or branched $C_{1-10}$alkyl unsubstituted or substituted by halogen or a tert-butyl protecting group; $C_{1-4}$alkoxy; —$C_{6-10}$aryl unsubstituted or substituted by $C_{1-10}$ alkyl, nitro, $C_{1-15}$alkoxy or halogen; $C_{3-10}$cycloalkyl; —$C_{3-10}$cycloalkenyl; linear or branched $C_{2-10}$alkenyl; —$C_{5-10}$heteroaryl; —$C_{1-3}$alkylene-$C_{3-10}$cycloalkyl; $C_{2-3}$alkenylene-$C_{6-10}$aryl wherein $C_{6-10}$aryl is unsubstituted or substituted by halogen; —O—C(=O)—$C_{1-10}$alkyl. In some embodiments, $R_a$ is —O—$C_{1-4}$alkyl, —O-tert-butyloxycarbonyl protecting group or —O—C(=O)R$_{a3}$ wherein $R_{a3}$ is a tert-butyl protecting group; adamantyl; linear or branched $C_{1-8}$alkyl unsubstituted or substituted by halogen or a tert-butyl protecting group; $C_{1-4}$alkoxy; -phenyl unsubstituted or substituted by $C_{1-6}$ alkyl, nitro, $C_{1-4}$alkoxy or halogen; $C_{3-6}$cycloalkyl; —$C_{3-6}$cycloalkenyl; linear or branched $C_{2-6}$alkenyl; —$C_{5-6}$heteroaryl; —$C_{1-3}$alkylene-$C_{3-6}$cycloalkyl; $C_{2-3}$alkenylene-phenyl wherein phenyl is unsubstituted or substituted by halogen; —O—C(=O)—O—$C_{1-4}$alkyl. In some further embodiments, $C_{3-6}$cycloalkyl is cyclopropyl or cyclohexyl. In some further embodiments, —$C_{3-10}$cycloalkenyl is cyclohexenyl.

In some further embodiments, heteroaryl is pyrrolidinyl, pyrrolinyl, pyrazolidinyl, imidazolidinyl, pyrazolinyl, imidazolinyl, pyrazolyl, imidazolyl, tetrahydrofuranyl, furanyl, dioxolanyl, tetrahydrothiophenyl, thiophenyl, oxazolyl, isoxazolyl, isothiazolyl, thiazolyl, oxathiolanyl, piperidinyl, pyridinyl, piperazinyl, pyridazinyl, pyrimidinyl, pyrazinyl, tetrahydropyranyl, pyranyl, dioxanyl, thianyl, thiopyranyl, morpholinyl, oxazinyl or thiazinyl. In further embodiments, heteroaryl is furanyl, isoxazolyl or thiophenyl.

In some embodiments, $R_a$ is —OH, —C$_{00}$H, —O-phosphate, —O—$C_{1-6}$alkyl or —O—C(=O)—$C_{1-6}$alkyl, —O—C(=O)—$C_{1-4}$alkylene-NH(Fmoc or Bocprotecting group), or —O—C(=O)—NH—C(=O)—O—$C_{1-10}$alkyl.

In some embodiments, $R_c$ each is independently linear or branched $C_{1-6}$alkyl or linear or branched $C_{1-6}$alkoxyl. In some embodiments, $R_c$ each is independently halogen, linear or branched $C_{1-6}$alkyl, linear or branched $C_{1-6}$alkoxyl, or $C_{1-10}$alkenylene-Y—$C_{6-10}$heteroaryl; wherein Y is S and $C_{6-10}$heteroaryl is unsubstituted or substituted by $C_{1-15}$alkyl (preferably $C_{1-4}$alkyl), $C_{1-15}$alkenyl (preferably $C_{2-4}$alkyl), $C_{1-15}$alkoxy (preferably $C_{1-4}$alkoxy), —OH, —NH$_2$, —NO$_2$ or halogen. In a further embodiment, $C_{1-10}$alkenylene-Y—$C_{6-10}$heteroaryl is

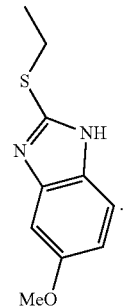

In some embodiments, the compound of the present invention is selected from the group consisting of:

| NCTU-SUN-ID | M.W. | Chemical Structure |
|---|---|---|
| 13001 | 488.56 | 2-(((4-methoxy-3,5-dimethylpyridin-2-yl)methyl)sulfinyl)-1H-benzo[d]imidazol-6-yl 2-((tert-butoxycarbonyl)amino)acetate |

| NCTU-SUN-ID | M.W. | Chemical Structure |
|---|---|---|
| 26090 | 410.52 | 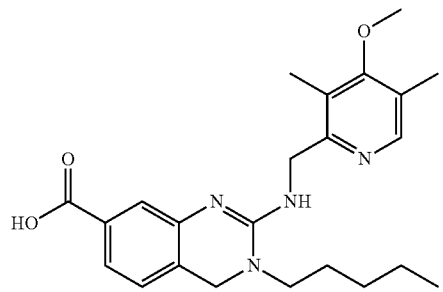 [SMILES: CCCCCN1Cc2ccc(C(=O)O)cc2N=C1NCc1ncc(C)c(OC)c1C]<br>2-(((4-methoxy-3,5-dimethylpyridin-2-yl)methyl)amino)-3-pentyl-3,4-dihydroquinazoline-7-carboxylic acid |
| 21115 | 398.46 | 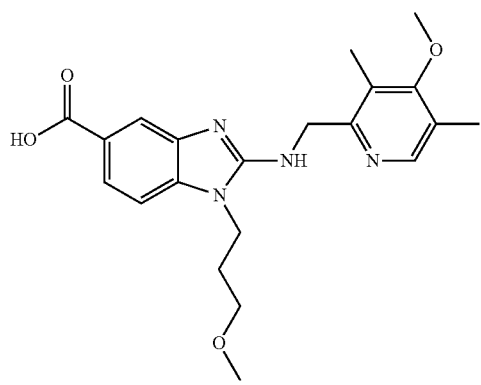 [SMILES: COCCCn1c(NCc2ncc(C)c(OC)c2C)nc2cc(C(=O)O)ccc21]<br>2-(((4-methoxy-3,5-dimethylpyridin-2-yl)methyl)amino)-1-(3-methoxypropyl)-1H-benzo[d]imidazole-5-carboxylic acid |
| 25030 | 429.17 | 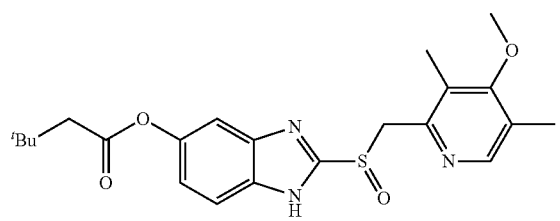 [SMILES: COc1c(C)cnc(CS(=O)c2nc3cc(OC(=O)CC(C)(C)C)ccc3[nH]2)c1C]<br>(2-(((4-methoxy-3,5-dimethylpyridin-2-yl)methyl)sulfinyl)-1H-benzo[d]imidazol-5-yl 3,3-dimethylbutanoate) |
| 28096 | 479.55 | 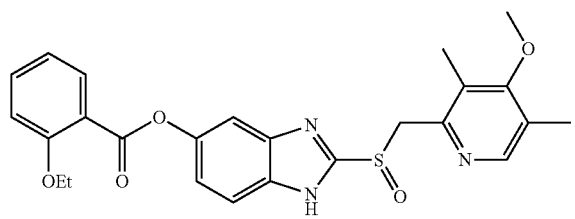 [SMILES: CCOc1ccccc1C(=O)Oc1ccc2[nH]c(S(=O)Cc3ncc(C)c(OC)c3C)nc2c1]<br>(2-(((5-methoxy-4,6-dimethylpyridin-2-yl)methyl)sulfinyl)-1H-benzo[d]imidazol-5-yl 2-ethoxybenzoate) |

-continued

| NCTU-SUN-ID | M.W. | Chemical Structure |
|---|---|---|
| 12093 | 472.56 | 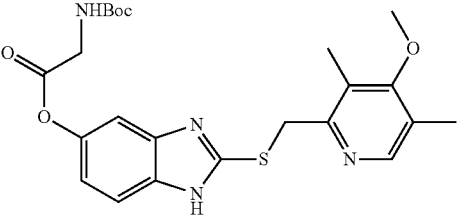 [SMILES: COc1c(C)cnc(CSc2nc3cc(OC(=O)CNC(=O)OC(C)(C)C)ccc3[nH]2)c1C]<br>2-(((4-methoxy-3,5-dimethylpyridin-2-yl)methyl)thio)-1H-benzo[d]imidazol-5-yl (tert-butoxycarbonyl)glycinate |
| 25016 | 415.16 | 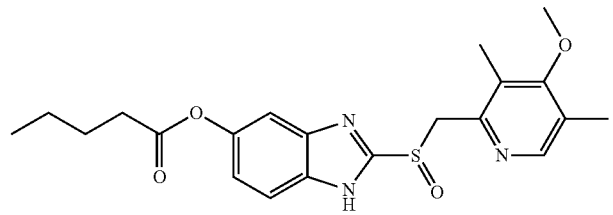 [SMILES: CCCCC(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl pentanoate) |
| 12130 | 508.43 | 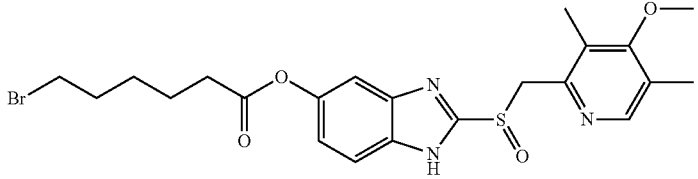 [SMILES: COc1c(C)cnc(CS(=O)c2nc3cc(OC(=O)CCCCCBr)ccc3[nH]2)c1C]<br>(2-(((4-methoxy-3,5-dimethylpyridin-2-yl)methyl)sulfinyl)-1H-benzo[d]imidazol-5-yl 6-bromohexanoate) |
| 27077 | 401.48 | 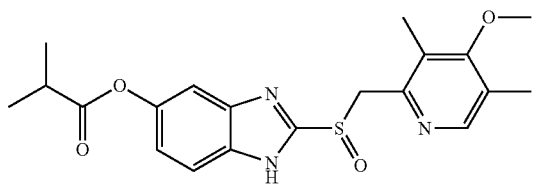<br>2-(((4-methoxy-3,5-dimethylpyridin-2-yl)methyl)sulfinyl)-1H-benzo[d]imidazol-5-yl isobutyrate |
| 27079 | 449.52 | 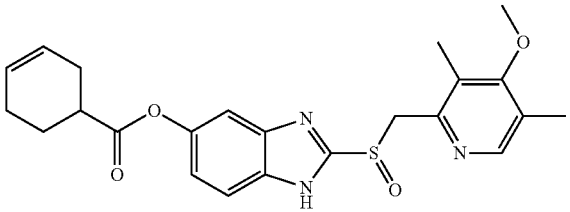<br>2-(((4-methoxy-3,5-dimethylpyridin-2-yl)methyl)sulfinyl)-1H-benzo[d]imidazol-5-yl cyclohex-3-enecarboxylate |

| NCTU-SUN-ID | M.W. | Chemical Structure |
|---|---|---|
| 26089 | 420.47 | 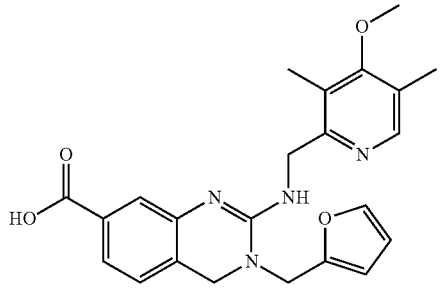 [SMILES: COc1c(C)cnc(CNC2=Nc3cc(C(=O)O)ccc3CN2Cc2ccco2)c1C]<br>3-(furan-2-ylmethyl)-2-(((4-methoxy-3,5-dimethylpyridin-2-yl)methyl)amino)-3,4-dihydroquinazoline-7-carboxylic acid |
| 21129 | 453.12 | 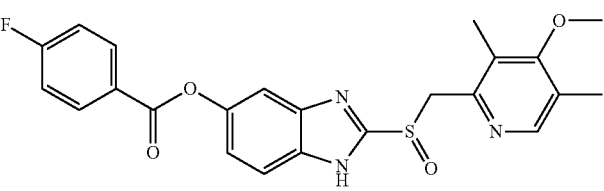 [SMILES: COc1c(C)cnc(CS(=O)c2nc3cc(OC(=O)c4ccc(F)cc4)ccc3[nH]2)c1C]<br>(2-(((4-methoxy-3,5-dimethylpyridin-2-yl)methyl)sulfinyl)-1H-benzo[d]imidazol-5-yl 4-fluorobenzoate) |
| 25032 | 403.12 | 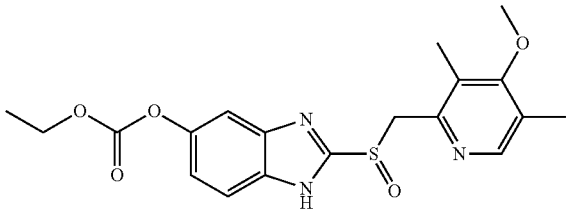<br>(ethyl (2-(((4-methoxy-3,5-dimethylpyridin-2-yl)methyl)sulfinyl)-1H-benzo[d]imidazol-5-yl) carbonate) |
| 26098 | 491.61 | 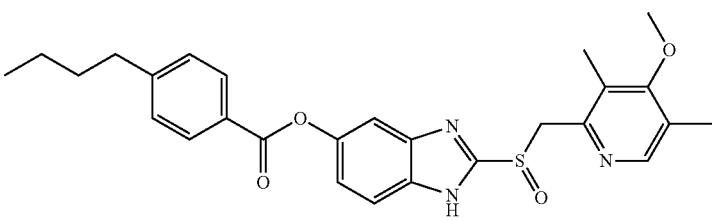 [SMILES: CCCCc1ccc(C(=O)Oc2ccc3[nH]c(S(=O)Cc4ncc(C)c(OC)c4C)nc3c2)cc1]<br>(2-(((4-methoxy-3,5-dimethylpyridin-2-yl)methyl)sulfinyl)-1H-benzo[d]imidazol-5-yl 4-butylbenzoate) |
| 21127 | 449.14 | 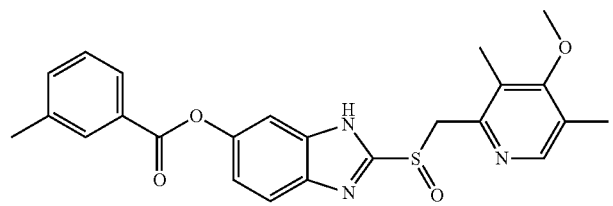<br>(2-(((4-methoxy-3,5-dimethylpyridin-2-yl)methyl)sulfinyl)-1H-benzo[d]imidazol-5-yl 3-methylbenzoate) |

-continued

| NCTU-SUN-ID | M.W. | Chemical Structure |
|---|---|---|
| 25017 | 480.11 | 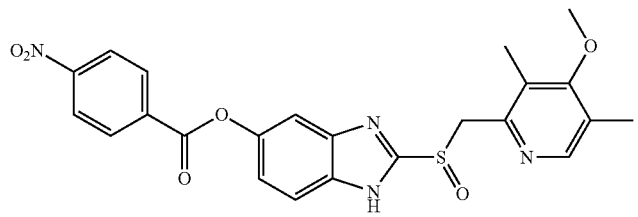 [SMILES: COc1c(C)cnc(CS(=O)c2nc3cc(OC(=O)c4ccc([N+](=O)[O-])cc4)ccc3[nH]2)c1C]<br>(2-(((4-methoxy-3,5-dimethylpyridin-2-yl)methyl)sulfinyl)-1H-benzo[d]imidazol-5-yl 4-nitrobenzoate) |
| 12128 | 455.18 | 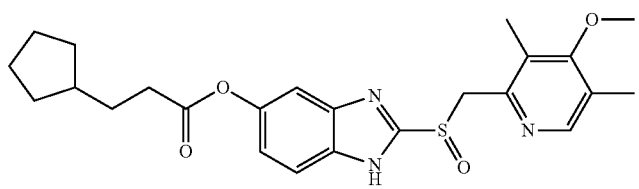 [SMILES: COc1c(C)cnc(CS(=O)c2nc3cc(OC(=O)CCC4CCCC4)ccc3[nH]2)c1C]<br>(2-(((4-methoxy-3,5-dimethylpyridin-2-yl)methyl)sulfinyl)-1H-benzo[d]imidazol-5-yl 3-cyclopentylpropanoate) |
| 26071 | 460.53 | 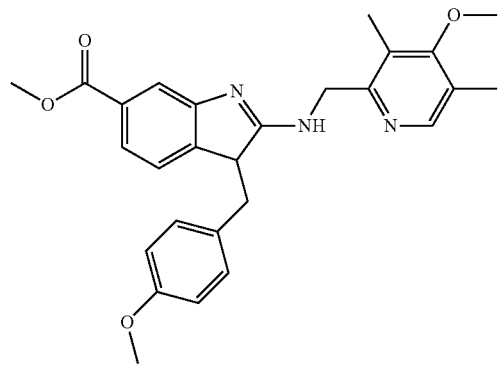<br>Methyl 2-(((4-methoxy-3,5-dimethylpyridin-2-yl)methyl)amino)-1-(4-methoxybenzyl)-1H-benzo[d]imidazole-5-carboxylate |
| 11021 | 453.12 | 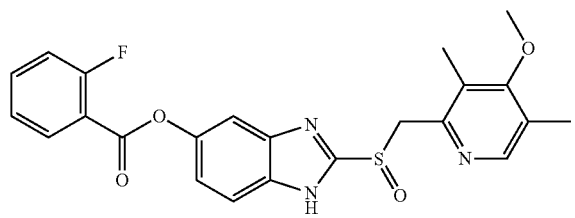<br>(2-(((4-methoxy-3,5-dimethylpyridin-2-yl)methyl)sulfinyl)-1H-benzo[d]imidazol-5-yl 2-fluorobenzoate) |

| NCTU-SUN-ID | M.W. | Chemical Structure |
|---|---|---|
| 21118 | 444.22 | 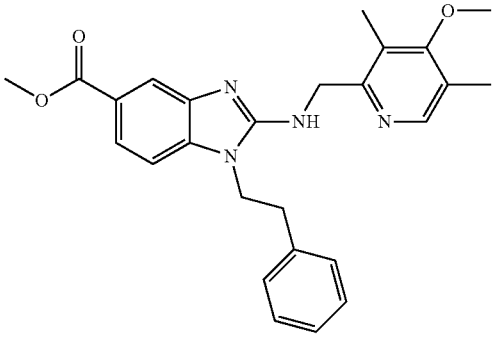<br>Methyl 2-(((4-methoxy-3,5-dimethylpyridin-2-yl)methyl)amino)-1-phenethyl-1H-benzo[d]imidazole-5-carboxylate |
| 26070 | 406.44 | 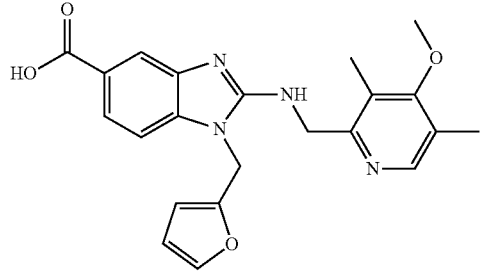 [SMILES: COc1c(C)cnc(CNc2nc3cc(C(=O)O)ccc3n2Cc2ccco2)c1C]<br>1-(furan-2-ylmethyl)-2-(((4-methoxy-3,5-dimethylpyridin-2-yl)methyl)amino)-1H-benzo[d]imidazole-5-carboxylic acid |
| 25029 | 415.16 | 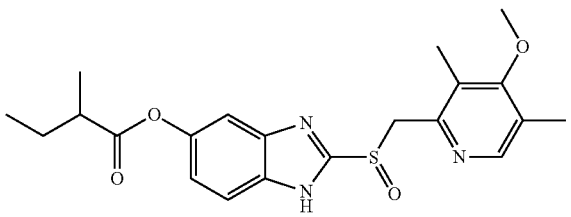 [SMILES: CCC(C)C(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl 2-methylbutanoate) |
| 12129 | 495.98 | 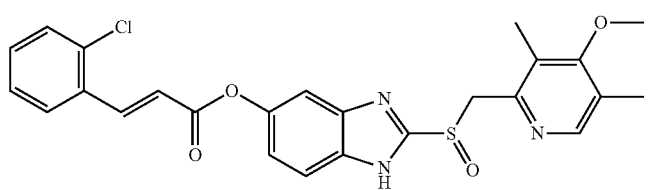 [SMILES: COc1c(C)cnc(CS(=O)c2nc3cc(OC(=O)/C=C/c4ccccc4Cl)ccc3[nH]2)c1C]<br>(2-(((4-methoxy-3,5-dimethylpyridin-2-yl)methyl)sulfinyl)-1H-benzo[d]imidazol-5-yl (E)-3-(2-chlorophenyl)acrylate) |

-continued

| NCTU-SUN-ID | M.W. | Chemical Structure |
|---|---|---|
| 11023 | 426.10 | 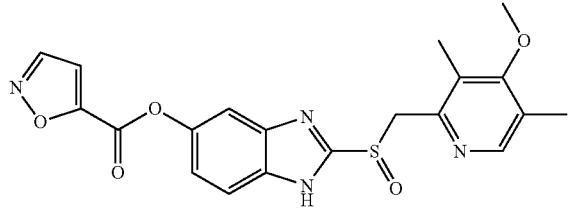 [SMILES: COc1c(C)cnc(CS(=O)c2nc3cc(OC(=O)c4ccno4)ccc3[nH]2)c1C] (2-(((4-methoxy-3,5-dimethylpyridin-2-yl)methyl)sulfinyl)-1H-benzo[d]imidazol-5-yl isoxazole-5-carboxylate) |
| 26096 | 401.48 | 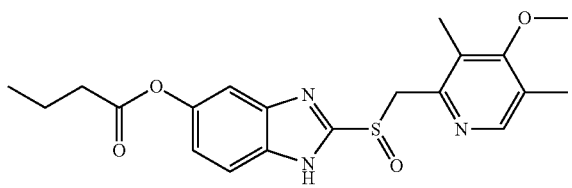 [SMILES: CCCC(=O)Oc1ccc2[nH]c(S(=O)Cc3ncc(C)c(OC)c3C)nc2c1] (2-(((4-methoxy-3,5-dimethylpyridin-2-yl)methyl)sulfinyl)-1H-benzo[d]imidazol-5-yl butyrate) |
| 25027 | 413.14 | 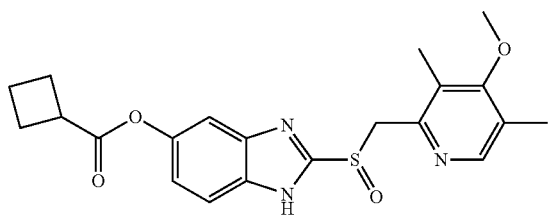 [SMILES: COc1c(C)cnc(CS(=O)c2nc3cc(OC(=O)C4CCC4)ccc3[nH]2)c1C] (2-(((4-methoxy-3,5-dimethylpyridin-2-yl)methyl)sulfinyl)-1H-benzo[d]imidazol-5-yl cyclobutanecarboxylate) |
| 28092 | 399.13 | 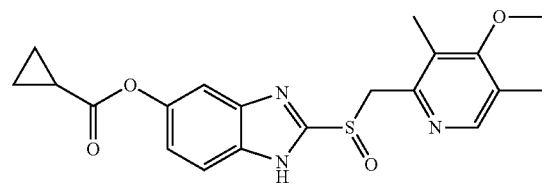 [SMILES: COc1c(C)cnc(CS(=O)c2nc3cc(OC(=O)C4CC4)ccc3[nH]2)c1C] (2-(((4-methoxy-3,5-dimethylpyridin-2-yl)methyl)sulfinyl)-1H-benzo[d]imidazol-5-yl cyclopropanecarboxylate) |

| NCTU-SUN-ID | M.W. | Chemical Structure |
|---|---|---|
| 12088 | 469.64 | 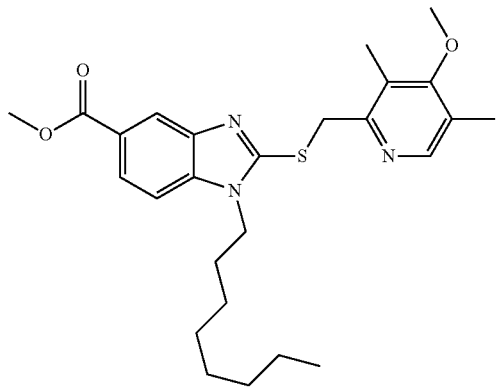<br>methyl 2-(((4-methoxy-3,5-dimethylpyridin-2-yl)methyl)thio)-1-octyl-1H-benzo[d]imidazole-5-carboxylate |
| 12127 | 415.5 | 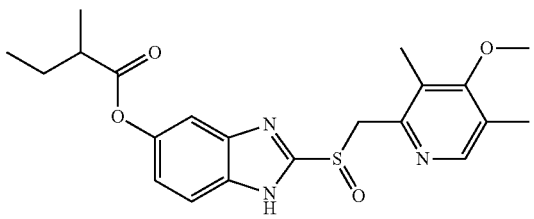 [SMILES: CCC(C)C(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl 2-methylbutanoate) |
| 21117 | 434.54 | 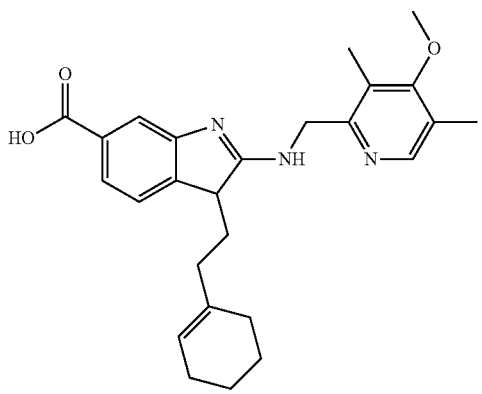 [SMILES: COc1c(C)cnc(CNC2=Nc3cc(C(=O)O)ccc3C2CCC2=CCCCC2)c1C]<br>1-(2-(cyclohex-1-en-1-yl)ethyl)-2-(((4-methoxy-3,5-dimethylpyridin-2-yl)methyl)amino)-1H-benzo[d]imidazole-5-carboxylic acid |

-continued

| NCTU-SUN-ID | M.W. | Chemical Structure |
|---|---|---|
| 12084 | 481.61 | 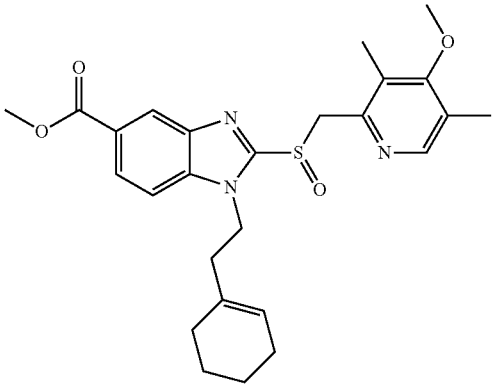<br>Methyl 1-(2-(cyclohex-1-en-1-yl)ethyl)-2-(((4-methoxy-3,5-dimethylpyridin-2-yl)methyl)sulfinyl)-1H-benzo[d]imidazole-5-carboxylate |
| 21126 | 480.11 | 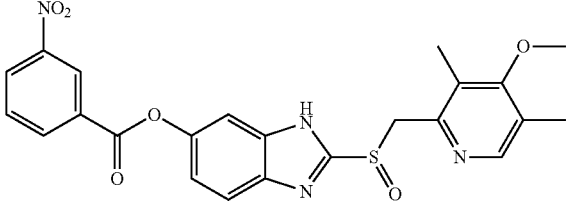 [SMILES: COc1c(C)cnc(CS(=O)c2nc3ccc(OC(=O)c4cccc([N+](=O)[O-])c4)cc3[nH]2)c1C]<br>(2-(((4-methoxy-3,5-dimethylpyridin-2-yl)methyl)sulfinyl)-1H-benzo[d]imidazol-5-yl 3-nitrobenzoate) |
| 26097 | 441.55 | 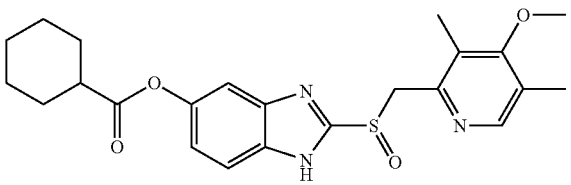 [SMILES: COc1c(C)cnc(CS(=O)c2nc3cc(OC(=O)C4CCCCC4)ccc3[nH]2)c1C]<br>(2-(((4-methoxy-3,5-dimethylpyridin-2-yl)methyl)sulfinyl)-1H-benzo[d]imidazol-5-yl cyclohexanecarboxylate) |
| 21110 | 412.49 | 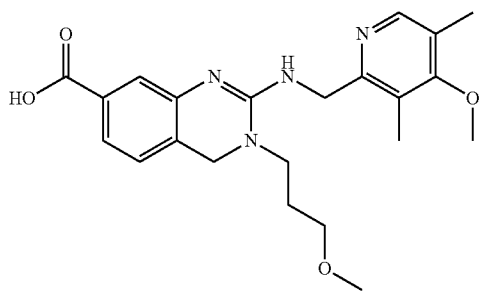 [SMILES: COCCCN1Cc2ccc(C(=O)O)cc2N=C1NCc1ncc(C)c(OC)c1C]<br>2-(((4-methoxy-3,5-dimethylpyridin-2-yl)methyl)amino)-3-(3-methoxypropyl)-3,4-dihydroquinazoline-7-carboxylic acid |

-continued
| NCTU-SUN-ID | M.W. | Chemical Structure |
|---|---|---|
| 21116 | 448.57 | 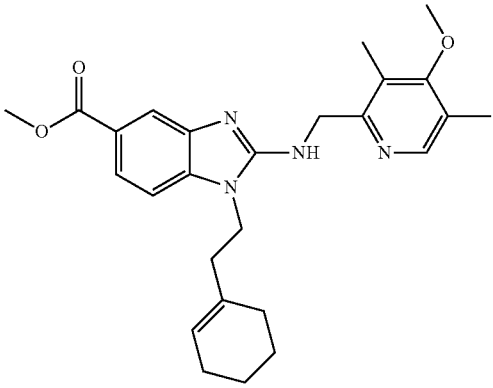<br>Methyl 1-(2-(cyclohex-1-en-1-yl)ethyl)-2-(((4-methoxy-3,5-dimethylpyridin-2-yl)methyl)amino)-1H-benzo[d]imidazole-5-carboxylate |
| 21120 | 517.27 | 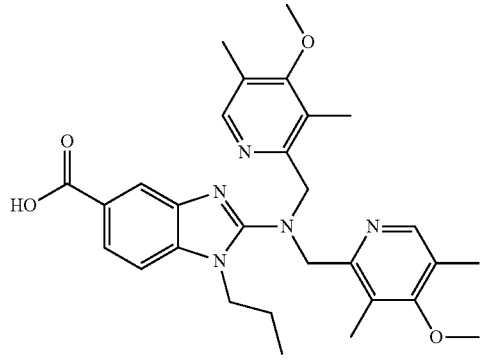 [SMILES: CCCn1c(N(Cc2ncc(C)c(OC)c2C)Cc2ncc(C)c(OC)c2C)nc2cc(C(=O)O)ccc21]<br>2-(bis((4-methoxy-3,5-dimethylpyridin-2-yl)methyl)amino)-1-propyl-1H-benzo[d]imidazole-5-carboxylic acid |
| 21121 | 579.28 | 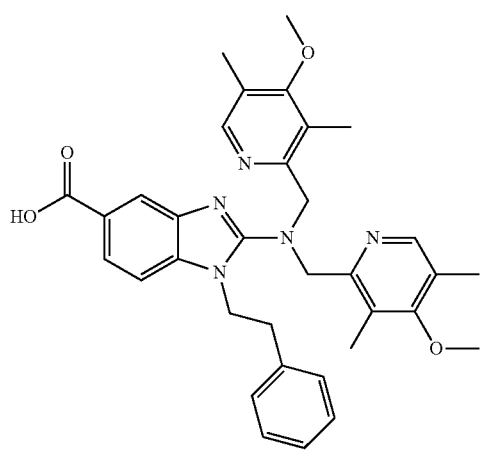 [SMILES: COc1c(C)cnc(CN(Cc2ncc(C)c(OC)c2C)c2nc3cc(C(=O)O)ccc3n2CCc2ccccc2)c1C]<br>2-(bis((4-methoxy-3,5-dimethylpyridin-2-yl)methyl)amino)-1-phenethyl-1H-benzo[d]imidazole-5-carboxylic acid |

-continued

| NCTU-SUN-ID | M.W. | Chemical Structure |
|---|---|---|
| 22138 | 328.43 | 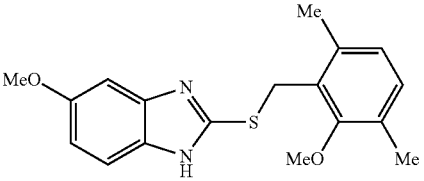 [SMILES: COc1ccc2[nH]c(SCc3c(C)ccc(C)c3OC)nc2c1]<br>5-methoxy-2-((2-methoxy-3,6-dimethylbenzyl)thio)-1H-benzo[d]imidazole |
| 25015 | 415.16 | 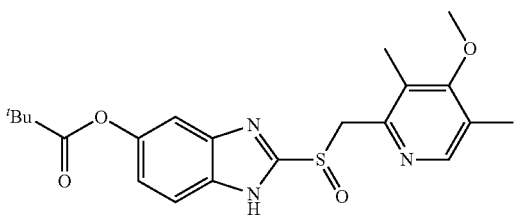 [SMILES: COc1c(C)cnc(CS(=O)c2nc3cc(OC(=O)C(C)(C)C)ccc3[nH]2)c1C]<br>(2-(((4-methoxy-3,5-dimethylpyridin-2-yl)methyl)sulfinyl)-1H-benzo[d]imidazol-5-yl pivalate) |
| 28094 | 449.52 | 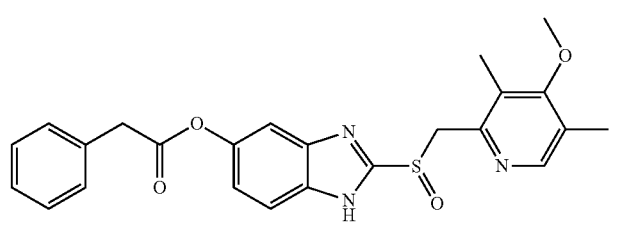 [SMILES: COc1c(C)cnc(CS(=O)c2nc3cc(OC(=O)Cc4ccccc4)ccc3[nH]2)c1C]<br>(2-(((4-methoxy-3,5-dimethylpyridin-2-yl)methyl)sulfinyl)-1H-benzo[d]imidazol-5-yl 2-phenylacetate) |
| 28091 | 480.11 | 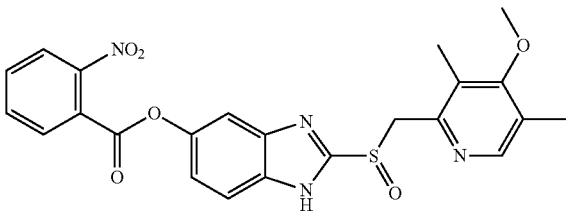 [SMILES: COc1c(C)cnc(CS(=O)c2nc3cc(OC(=O)c4ccccc4[N+](=O)[O-])ccc3[nH]2)c1C]<br>(2-(((4-methoxy-3,5-dimethylpyridin-2-yl)methyl)sulfinyl)-1H-benzo[d]imidazol-5-yl 2-nitrobenzoate) |
| 21130 | 413.14 | 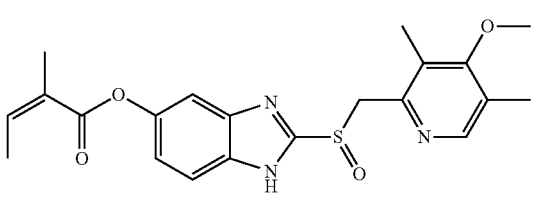 [SMILES: C/C=C(/C)C(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl (Z)-2-methylbut-2-enoate) |

| NCTU-SUN-ID | M.W. | Chemical Structure |
|---|---|---|
| 21103 | 412.49 | 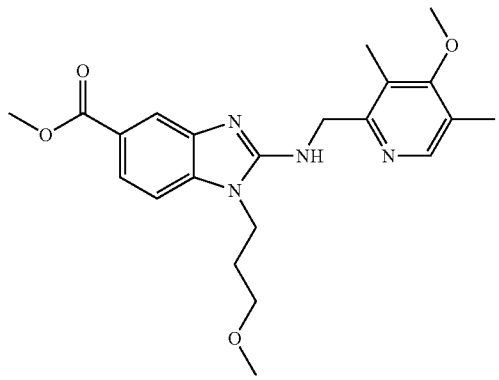<br>Methyl 2-(((4-methoxy-3,5-dimethylpyridin-2-yl)methyl)amino)-1-(3-methoxypropyl)-1H-benzo[d]imidazole-5-carboxylate |
| 21122 | 373.11 | 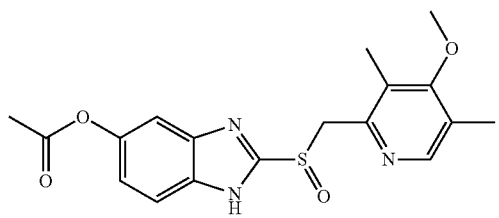 [SMILES: COc1c(C)cnc(CS(=O)c2nc3cc(OC(C)=O)ccc3[nH]2)c1C]<br>(2-(((4-methoxy-3,5-dimethylpyridin-2-yl)methyl)sulfinyl)-1H-benzo[d]imidazol-5-yl acetate) |
| 11022 | 493.62 | 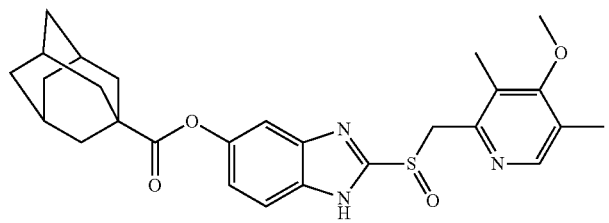 [SMILES: COc1c(C)cnc(CS(=O)c2nc3cc(OC(=O)C45CC6CC(CC(C6)C4)C5)ccc3[nH]2)c1C]<br>(2-(((4-methoxy-3,5-dimethylpyridin-2-yl)methyl)sulfinyl)-1H-benzo[d]imidazol-5-yl (3r,5r,7r)-adamantane-1-carboxylate) |
| 11030 | 491.61 | 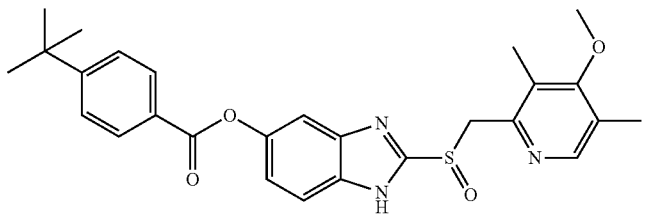 [SMILES: COc1c(C)cnc(CS(=O)c2nc3cc(OC(=O)c4ccc(C(C)(C)C)cc4)ccc3[nH]2)c1C]<br>(2-(((4-methoxy-3,5-dimethylpyridin-2-yl)methyl)sulfinyl)-1H-benzo[d]imidazol-5-yl 4-(tert-butyl)benzoate) |

-continued

| NCTU-SUN-ID | M.W. | Chemical Structure |
|---|---|---|
| 21102 | 368.44 | 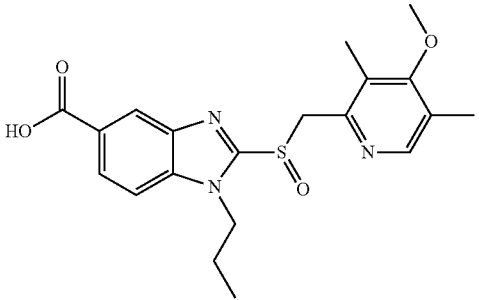 [SMILES: CCCn1c(S(=O)Cc2ncc(C)c(OC)c2C)nc2cc(C(=O)O)ccc21]<br>2-(((4-methoxy-3,5-dimethylpyridin-2-yl)methyl)amino)-1-propyl-1H-benzo[d]imidazole-5-carboxylic acid |
| 21132 | 431.15 | 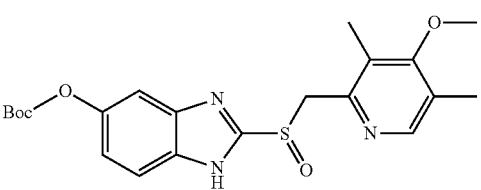 [SMILES: COc1c(C)cnc(CS(=O)c2nc3cc(OC(=O)OC(C)(C)C)ccc3[nH]2)c1C]<br>tert-butyl (2-(((4-methoxy-3,5-dimethylpyridin-2-yl)methyl)sulfinyl)-1H-benzo[d]imidazol-5-yl) carbonate |
| 12123 | 385.44 | 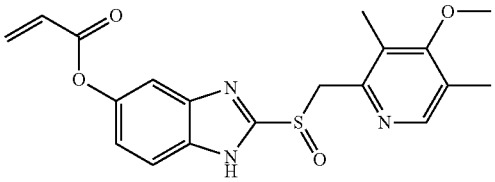 [SMILES: C=CC(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl acrylate) |
| 13084 | 563.56 | 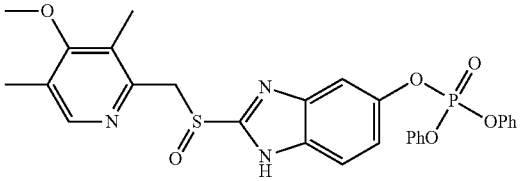 [SMILES: COc1c(C)cnc(CS(=O)c2nc3cc(OP(=O)(Oc4ccccc4)Oc4ccccc4)ccc3[nH]2)c1C]<br>2-(((4-methoxy-3,5-dimethylpyridin-2-yl)methyl)sulfinyl)-1H-benzo[d]imidazol-5-yl diphenyl phosphate |
| 12094 | 670.78 | 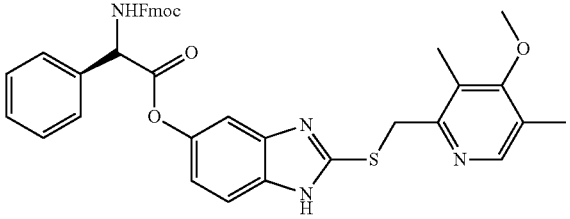<br>2-((((4-methoxy-3,5-dimethylpyridin-2-yl)methyl)thio)-1H benzo[d]-imidazole-5-yl (S)-2-((((9H-fluoren-9-yl)methoxy)carbonyl)amino)-2-phenylacetate |

| NCTU-SUN-ID | M.W. | Chemical Structure |
|---|---|---|
| 21105 | 583.73 | 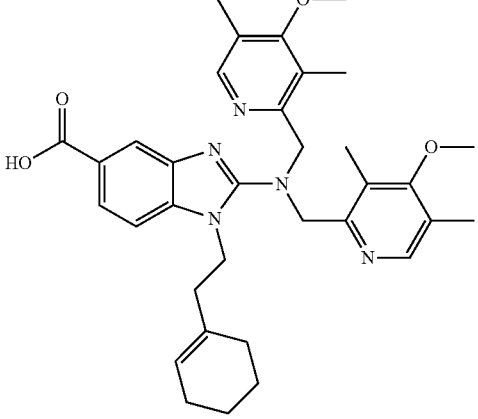<br>2-(bis((4-methoxy-3,5-dimethylpyridin-2-yl)methyl)amino)-1-(2-(cyclohex-1-en-1-yl)ethyl)-1H-benzo[d]imidazole-5-carboxylic acid |
| 12124 | 399.46 | 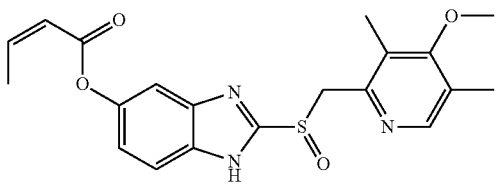 [SMILES: C/C=C\C(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl (Z)-but-2-enoate) |
| 12122 | 425.46 | 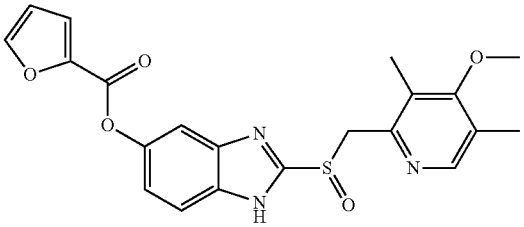 [SMILES: COc1c(C)cnc(CS(=O)c2nc3cc(OC(=O)c4ccco4)ccc3[nH]2)c1C]<br>(2-(((4-methoxy-3,5-dimethylpyridin-2-yl)methyl)sulfinyl)-1H-benzo[d]imidazol-5-yl furan-2-carboxylate) |
| 26072 | 583.69 | 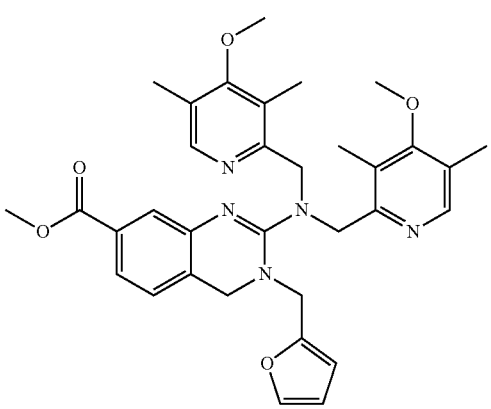<br>Methyl 2-(bis((4-methoxy-3,5-dimethylpyridin-2-yl)methyl)amino)-3-(furan-2-ylmethyl)-3,4-dihydroquinazoline-7-carboxylate |

| NCTU-SUN-ID | M.W. | Chemical Structure |
|---|---|---|
| 22140 | 506.14 | 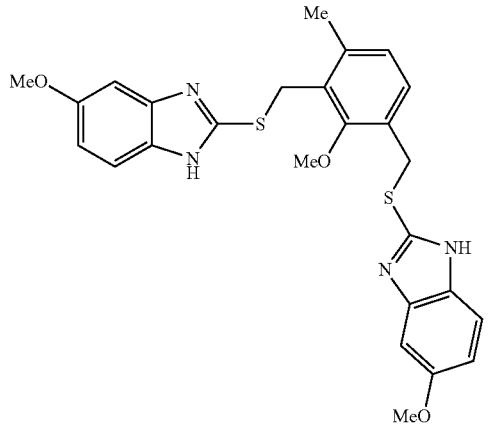 [SMILES: COc1ccc2[nH]c(SCc3ccc(C)c(CSc4nc5cc(OC)ccc5[nH]4)c3OC)nc2c1]
2,2'-(((2-methoxy-4-methyl-1,3-phenylene)bis(methylene))bis(sulfanediyl))bis(5-methoxy-1H-benzo[d]imidazole) |
| 21133 | 506.11 | 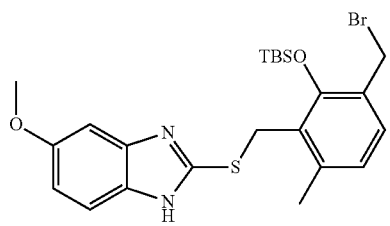 [SMILES: COc1ccc2[nH]c(SCc3c(C)ccc(CBr)c3O[Si](C)(C)C(C)(C)C)nc2c1]
2-((3-(bromomethyl)-2-((tert-butyldimethylsilyl)oxy)-6-methylbenzyl)thio)-5-methoxy-1H-benzo[d]imidazole |
| 21125 | 469.09 | 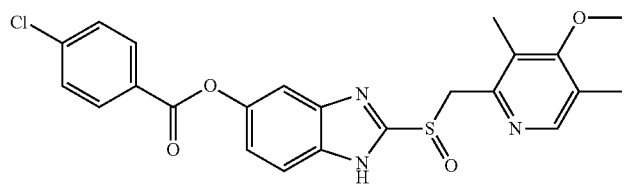 [SMILES: COc1c(C)cnc(CS(=O)c2nc3cc(OC(=O)c4ccc(Cl)cc4)ccc3[nH]2)c1C]
2-(((4-methoxy-3,5-dimethylpyridin-2-yl)methyl)sulfinyl)-1H-benzo[d]imidazol-5-yl 4-chlorobenzoate |
| 27078 | 439.53 | 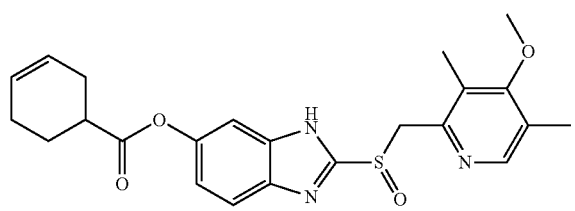 [SMILES: COc1c(C)cnc(CS(=O)c2nc3ccc(OC(=O)C4CC=CCC4)cc3[nH]2)c1C]
(2-(((4-methoxy-3,5-dimethylpyridin-2-yl)methyl)sulfinyl)-1H-benzo[d]imidazol-5-yl cyclohex-3-ene-1-carboxylate) |

| NCTU-SUN-ID | M.W. | Chemical Structure |
|---|---|---|
| 11020 | 465.13 | 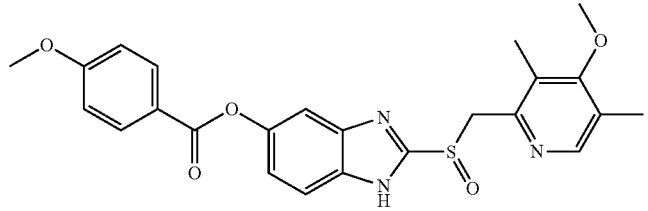<br>(2-(((4-methoxy-3,5-dimethylpyridin-2-yl)methyl)sulfinyl)-1H-benzo[d]imidazol-5-yl 4-methoxybenzoate) |
| 26076 | 396.49 | 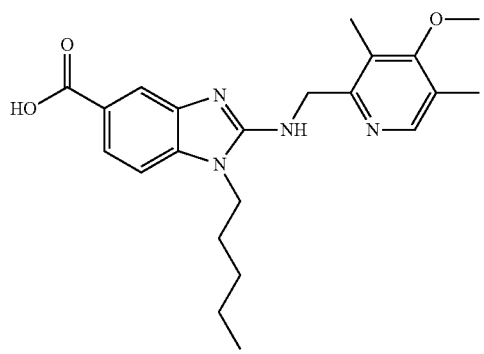 [SMILES: CCCCCn1c(NCc2ncc(C)c(OC)c2C)nc2cc(C(=O)O)ccc21]<br>2-(((4-methoxy-3,5-dimethylpyridin-2-yl)methyl)amino)-1-pentyl-1H-benzo[d]imidazole-5-carboxylic acid |
| 25031 | 403.12 | 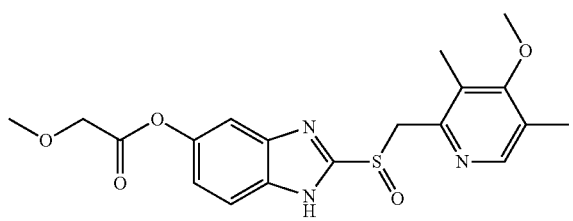<br>(2-(((4-methoxy-3,5-dimethylpyridin-2-yl)methyl)sulfinyl)-1H-benzo[d]imidazol-5-yl 2-methoxyacetate) |
| 21128 | 443.19 | 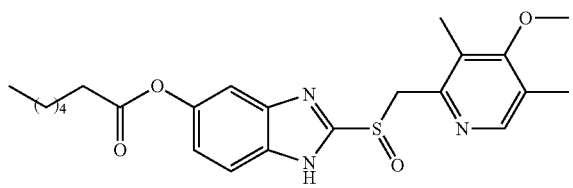<br>2-(((4-methoxy-3,5-dimethylpyridin-2-yl)methyl)sulfinyl)-1H-benzo[d]imidazol-5-yl heptanoate |

| NCTU-SUN-ID | M.W. | Chemical Structure |
|---|---|---|
| 27076 | 429.53 | 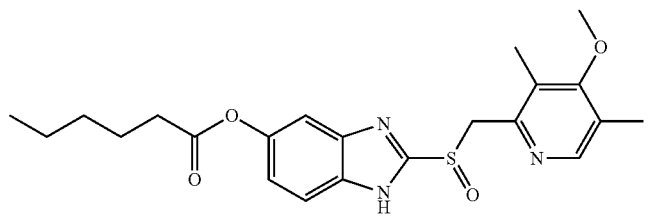 [SMILES: CCCCCC(=O)Oc1ccc2[nH]c(S(=O)Cc3ncc(C)c(OC)c3C)nc2c1]<br>2-(((4-methoxy-3,5-dimethylpyridin-2-yl)methyl)sulfinyl)-1H-benzo[d]imidazol-5-yl hexanoate |
| 12083 | 451.58 | 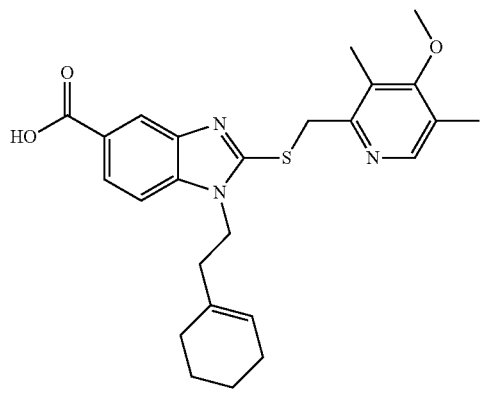 [SMILES: COc1c(C)cnc(CSc2nc3cc(C(=O)O)ccc3n2CCC2=CCCCC2)c1C]<br>1-(2-(cyclohex-1-en-1-yl)ethyl)-2-(((4-methoxy-3,5-dimethylpyridin-2-yl)methyl)thio)-1H-benzo[d]imidazole-5-carboxylic acid |
| 21119 | 430.20 | 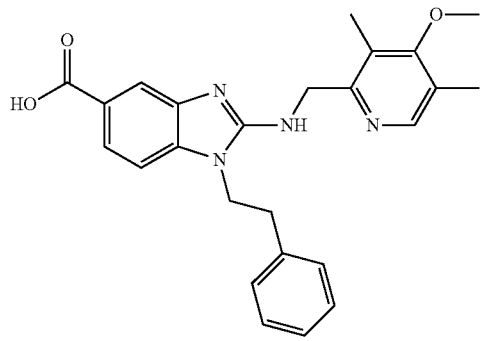 [SMILES: COc1c(C)cnc(CNc2nc3cc(C(=O)O)ccc3n2CCc2ccccc2)c1C]<br>2-(((4-methoxy-3,5-dimethylpyridin-2-yl)methyl)amino)-1-phenethyl-1H-benzo[d]imidazole-5-carboxylic acid |

| NCTU-SUN-ID | M.W. | Chemical Structure |
|---|---|---|
| 21104 | 547.65 | 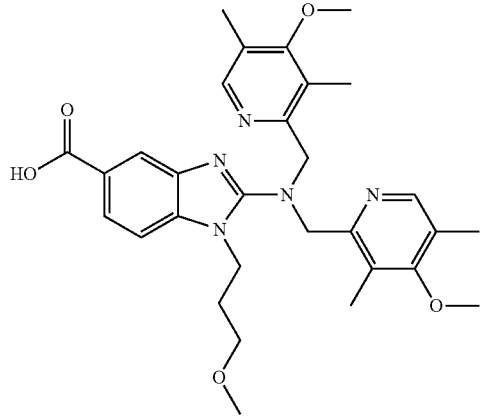 [SMILES: COCCCn1c(N(Cc2ncc(C)c(OC)c2C)Cc2ncc(C)c(OC)c2C)nc2cc(C(=O)O)ccc21]
2-(bis((4-methoxy-3,5-dimethylpyridin-2-yl)methyl)amino)-1-(3-methoxypropyl)-1H-benzo[d]imidazole-5-carboxylic acid |
| 21106 | 462.59 | 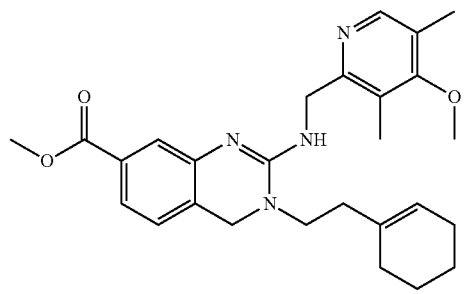
Methyl 3-(2-(cyclohex-1-en-1-yl)ethyl)-2-(((4-methoxy-3,5-dimethylpyridin-2-yl)methyl)amino)-3,4-dihydroquinazoline-7-carboxylate |
| 26077 | 446.51 | 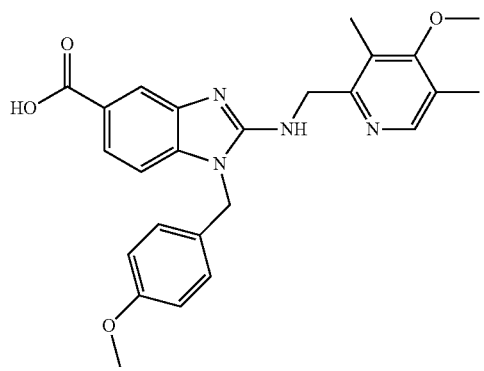 [SMILES: COc1ccc(Cn2c(NCc3ncc(C)c(OC)c3C)nc3cc(C(=O)O)ccc32)cc1]
2-(((4-methoxy-3,5-dimethylpyridin-2-yl)methyl)amino)-1-(4-methoxybenzyl)-1H-benzo[d]imidazole-5-carboxylic acid |

-continued

| NCTU-SUN-ID | M.W. | Chemical Structure |
|---|---|---|
| 26066 | 410.52 | 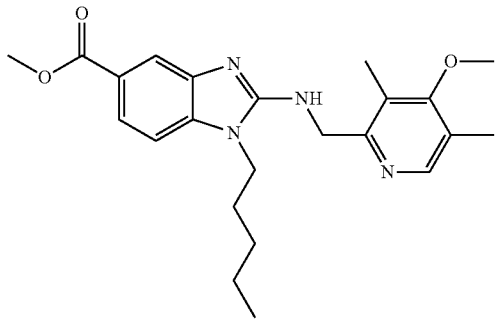
Methyl 2-(((4-methoxy-3,5-dimethylpyridin-2-yl)methyl)amino)-1-pentyl-1H-benzo[d]imidazole-5-carboxylate |
| 12125 | 413.49 | 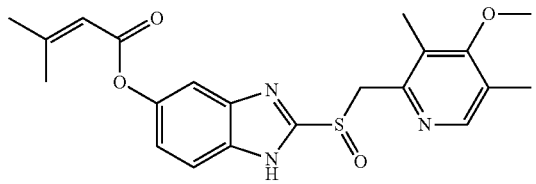 [SMILES: COc1c(C)cnc(CS(=O)c2nc3cc(OC(=O)C=C(C)C)ccc3[nH]2)c1C]
(2-(((4-methoxy-3,5-dimethylpyridin-2-yl)methyl)sulfinyl)-1H-benzo[d]imidazol-5-yl 3-methylbut-2-enoate) |
| 26065 | 420.46 | 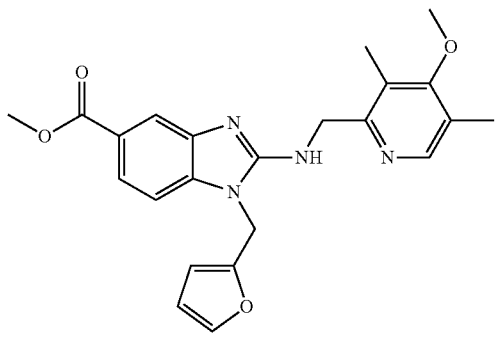
Methyl 1-(furan-2-ylmethyl)-2-(((4-methoxy-3,5-dimethylpyridin-2-yl)methyl)amino)-1H-benzo[d]imidazole-5-carboxylate |
| 26079 | 434.50 | 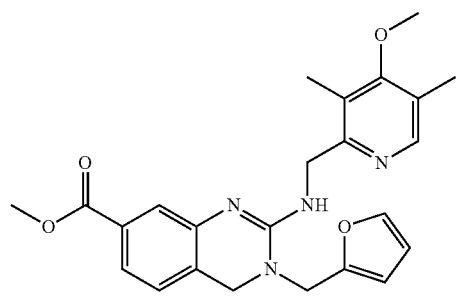
Methyl 3-(furan-2-ylmethyl)-2-(((4-methoxy-3,5-dimethylpyridin-2-yl)methyl)amino)-3,4-dihydroquinazoline-7-carboxylate |

-continued

| NCTU-SUN-ID | M.W. | Chemical Structure |
|---|---|---|
| 25028 | 441.08 | 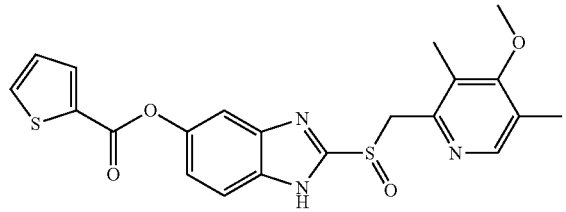 [SMILES: COc1c(C)cnc(CS(=O)c2nc3cc(OC(=O)c4cccs4)ccc3[nH]2)c1C]<br>(2-(((4-methoxy-3,5-dimethylpyridin-2-yl)methyl)sulfinyl)-1H-benzo[d]imidazol-5-yl thiophene-2-carboxylate) |
| 26092 | 474.56 | 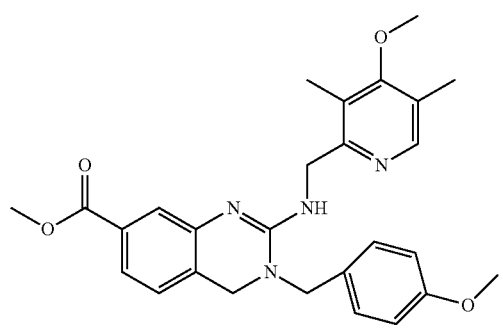<br>Methyl 2-(((4-methoxy-3,5-dimethylpyridin-2-yl)methyl)amino)-3-(4-methoxybenzyl)-3,4-dihydroquinazoline-7-carboxylate |
| 21124 | 435.13 | 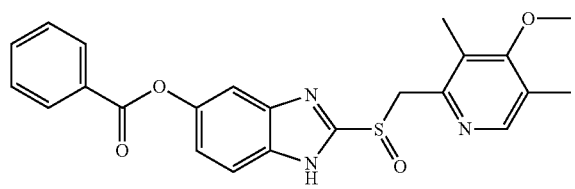 [SMILES: COc1c(C)cnc(CS(=O)c2nc3cc(OC(=O)c4ccccc4)ccc3[nH]2)c1C]<br>(2-(((4-methoxy-3,5-dimethylpyridin-2-yl)methyl)sulfinyl)-1H-benzo[d]imidazol-5-yl benzoate) |
| 28093 | 429.53 | 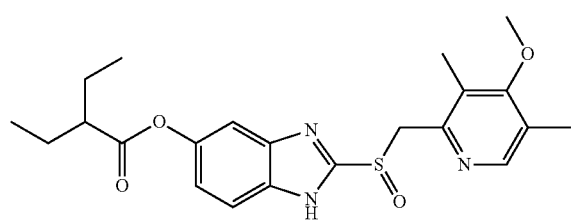 [SMILES: CCC(CC)C(=O)Oc1ccc2[nH]c(S(=O)Cc3ncc(C)c(OC)c3C)nc2c1]<br>(2-(((4-methoxy-3,5-dimethylpyridin-2-yl)methyl)sulfinyl)-1H-benzo[d]imidazol-5-yl 2-ethylbutanoate) |

-continued

| NCTU-SUN-ID | M.W. | Chemical Structure |
|---|---|---|
| 26091 | 424.55 | 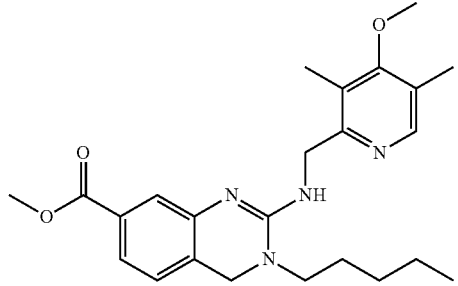 [SMILES: CCCCCN1Cc2ccc(C(=O)OC)cc2N=C1NCc1ncc(C)c(OC)c1C]
Methyl 2-(((4-methoxy-3,5-dimethylpyridin-2-yl)methyl)amino)-3-pentyl-3,4-dihydroquinazoline-7-carboxylate |
| 22139 | 344.11 | 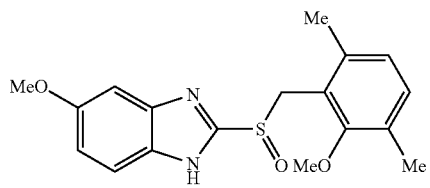 [SMILES: COc1ccc2[nH]c(S(=O)Cc3c(C)ccc(C)c3OC)nc2c1]
5-methoxy-2-((2-methoxy-3,6-dimethylbenzyl)sulfinyl)-1H-benzo[d]imidazole |
| 22141 | 314.1 | 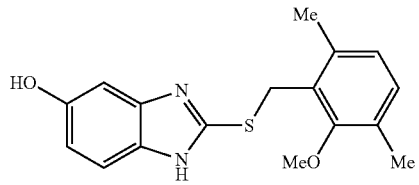 [SMILES: COc1c(C)ccc(C)c1CSc1nc2cc(O)ccc2[nH]1]
2-((2-methoxy-3,6-dimethylbenzyl)thio)-1H-benzo[d]imidazol-5-ol |
| 28087 | 449.14 | 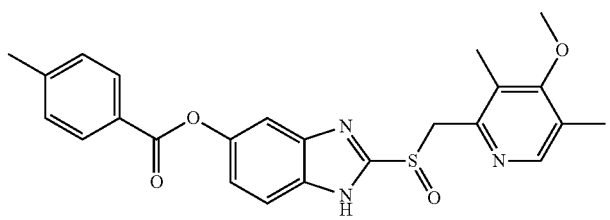
(2-(((4-methoxy-3,5-dimethylpyridin-2-yl)methyl)sulfinyl)-1H-benzo[d]imidazol-5-yl 4-methylbenzoate) |
| 21123 | 387.13 | 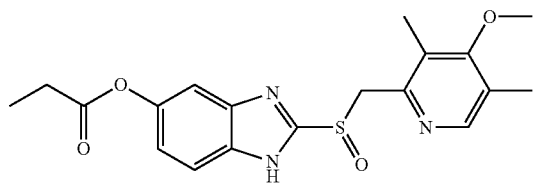 [SMILES: CCC(=O)Oc1ccc2[nH]c(S(=O)Cc3ncc(C)c(OC)c3C)nc2c1]
(2-(((4-methoxy-3,5-dimethylpyridin-2-yl)methyl)sulfinyl)-1H-benzo[d]imidazol-5-yl propionate) |

-continued

| NCTU-SUN-ID | M.W. | Chemical Structure |
|---|---|---|
| 12092 | 594.69 | 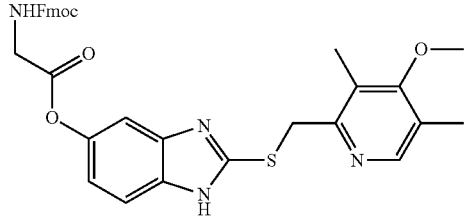<br>2-(((4-methoxy-3,5-dimethylpyridin-2-yl)methyl)thio)-1H-benzo[d]imidazol-5-yl (((9H-fluoren-9-yl)methoxy)carbonyl)glycinate |
| 21098 | 382.46 | 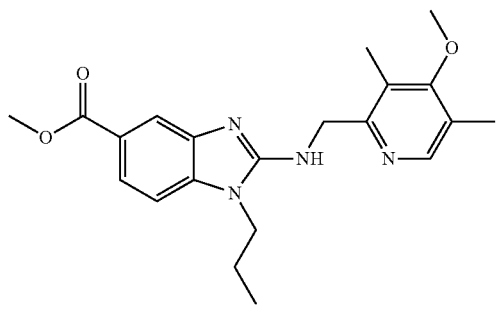<br>Methyl 2-(((4-methoxy-3,5-dimethylpyridin-2-yl)methyl)amino)-1-propyl-1H-benzo[d]imidazole-5-carboxylate |
| 21131 | 421.09 | 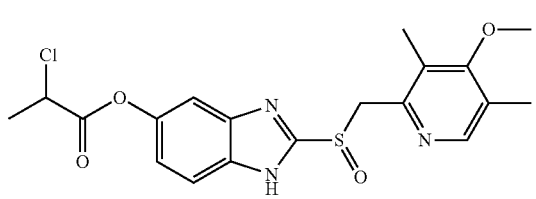 [SMILES: COc1c(C)cnc(CS(=O)c2nc3cc(OC(=O)C(C)Cl)ccc3[nH]2)c1C]<br>(2-(((4-methoxy-3,5-dimethylpyridin-2-yl)methyl)sulfinyl)-1H-benzo[d]imidazol-5-yl 2-chloropropanoate) |
| 12082 | 465.61 | 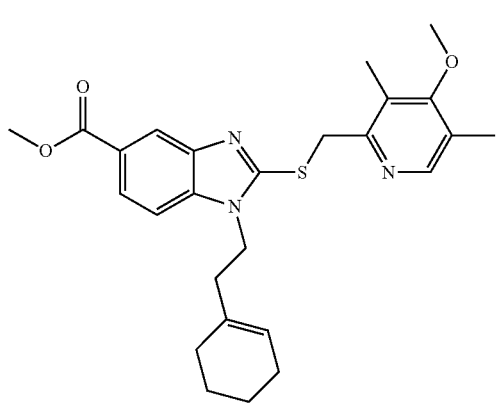<br>Methyl 1-(2-(cyclohex-1-en-1-yl)ethyl)-2-(((4-methoxy-3,5-dimethylpyridin-2-yl)methyl)thio)-1H-benzo[d]imidazole-5-carboxylate |

| NCTU-SUN-ID | M.W. | Chemical Structure |
|---|---|---|
| 28095 | 471.61 | 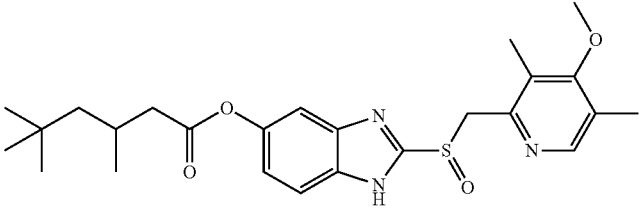 [SMILES: COc1c(C)cnc(CS(=O)c2nc3cc(OC(=O)CC(C)CC(C)(C)C)ccc3[nH]2)c1C]<br>(2-(((4-methoxy-3,5-dimethylpyridin-2-yl)methyl)sulfinyl)-1H-benzo[d]imidazol-5-yl 3,5,5-trimethylhexanoate) |
| 11031 | 487.93 | 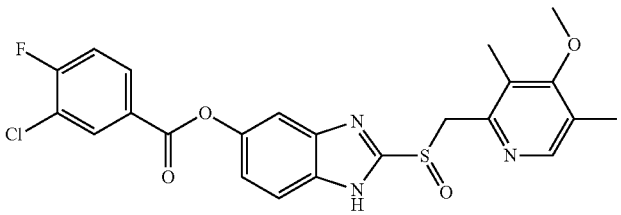 [SMILES: COc1c(C)cnc(CS(=O)c2nc3cc(OC(=O)c4ccc(F)c(Cl)c4)ccc3[nH]2)c1C]<br>(2-(((4-methoxy-3,5-dimethylpyridin-2-yl)methyl)sulfinyl)-1H-benzo[d]imidazol-5-yl 3-chloro-4-fluorobenzoate) | or a pharmaceutically acceptable salt thereof.

The present invention encompasses all stereoisomeric forms of the compounds of Formula I, Formula I-a and Formula I-b. Centers of asymmetry that are present in the compounds of Formula I, Formula I-a and Formula I-b can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula I-a and Formula I-b or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

General Preparation Procedures of the Compounds of the Present Invention

The compounds of Formula (I) of the present invention are prepared according to general chemical synthetic procedures. The preparation of the embodiments of the compounds of the present invention is illustrated below.

Synthetic Scheme and Procedure for the Preparation of the Compounds of the Invention from RS-D7

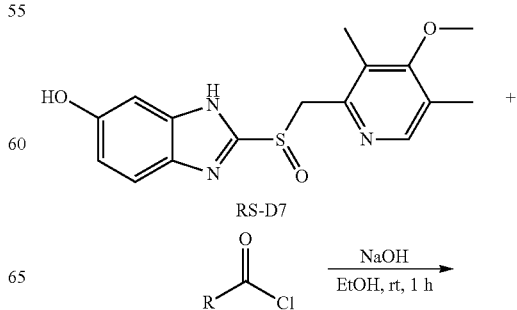

57
-continued
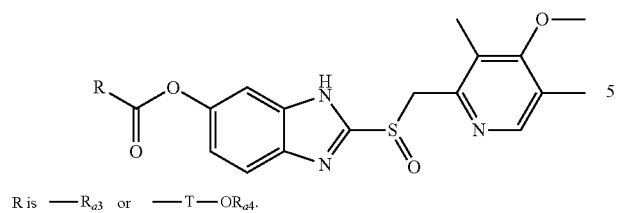
R is —$R_{a3}$ or —T—$OR_{a4}$.
Synthetic Scheme and Procedure for the Preparation of NCTU-SUN-26065 Series
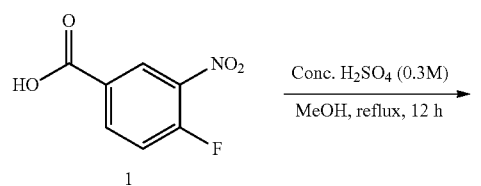
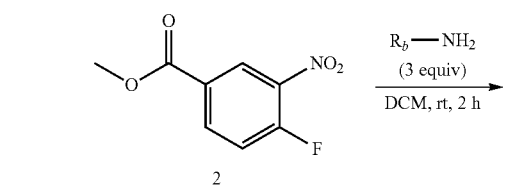
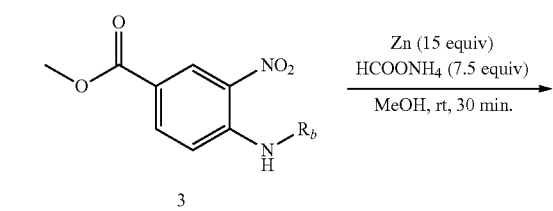
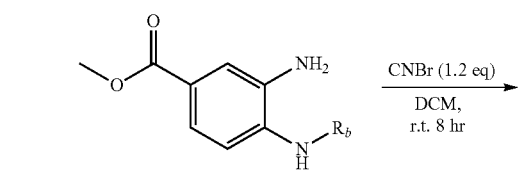
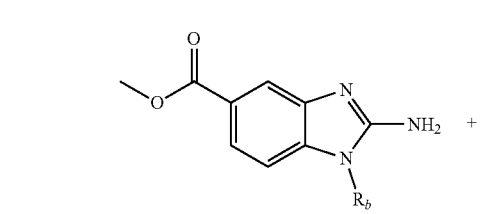
58
-continued
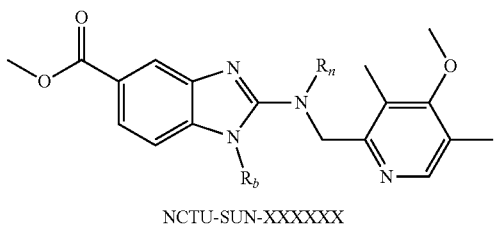
NCTU-SUN-XXXXXX
$R_b$ = H, linear or branched C1-15alkyl, linear or branched C2-15 alkenyl, C1-3alkoxy-C1-15alkyl-, —T'-C3-10cycloalkyl, —T'-C3-10cycloalkenyl, —T'-C6-10 aryl or —T'-C5-10heteroaryl
$R_n$ = H, 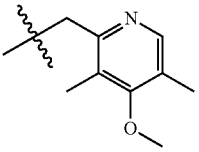
Synthetic Scheme and Procedure for the Preparation of NCTU-SUN-26070 Series
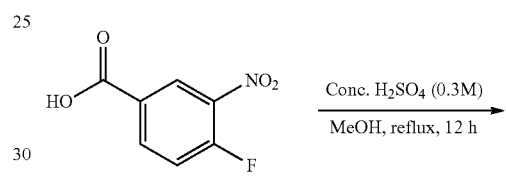
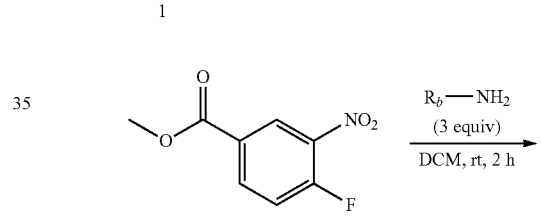
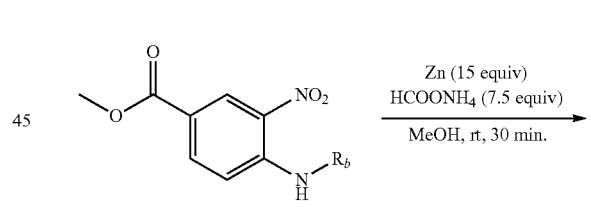
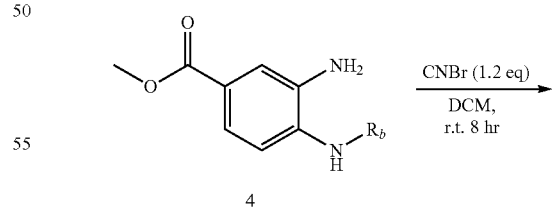
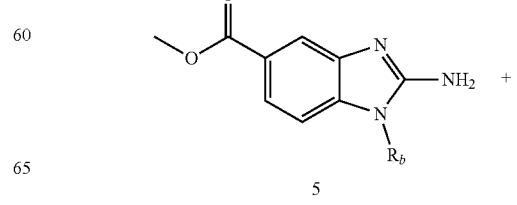

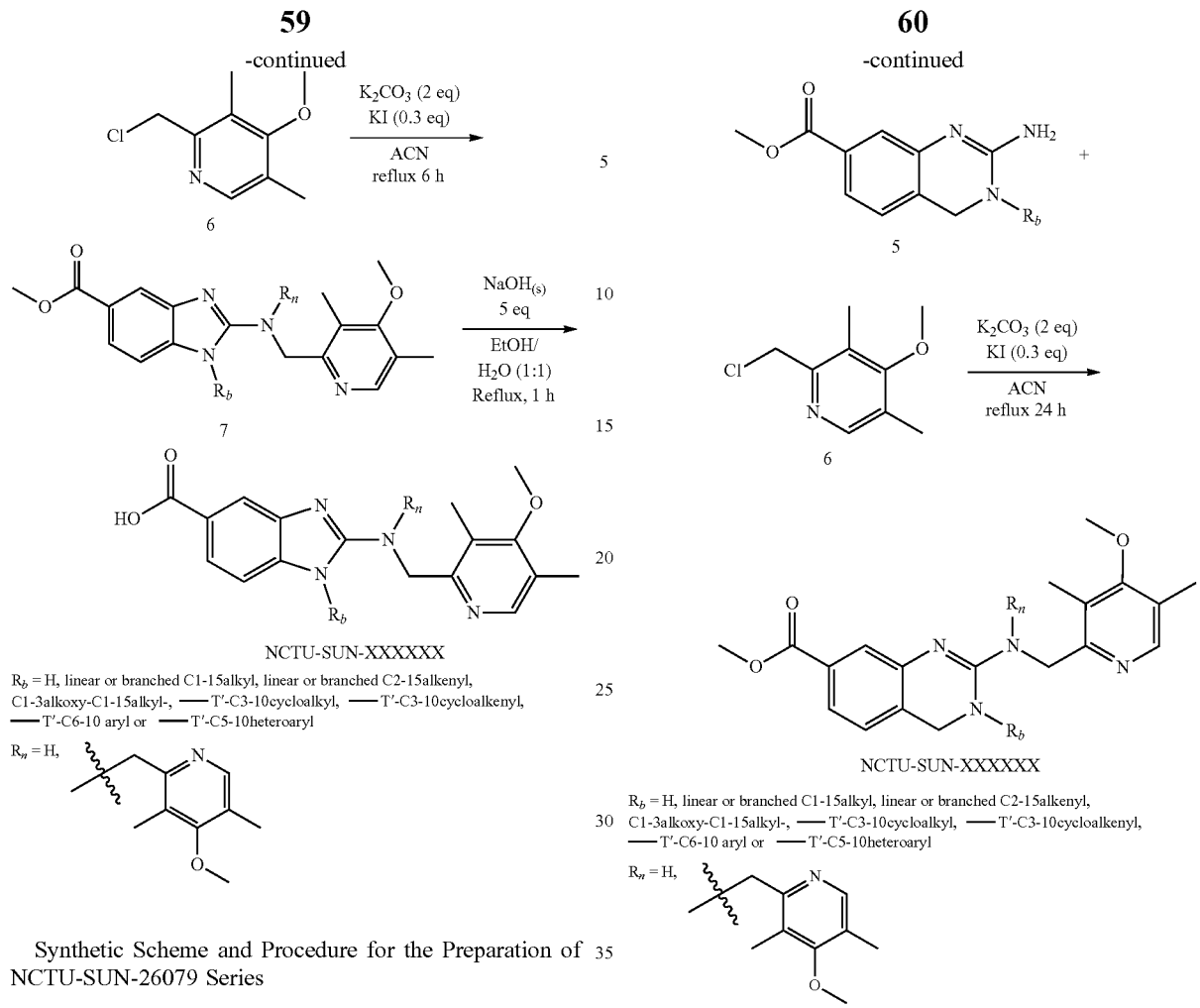
Synthetic Scheme and Procedure for the Preparation of NCTU-SUN-26079 Series
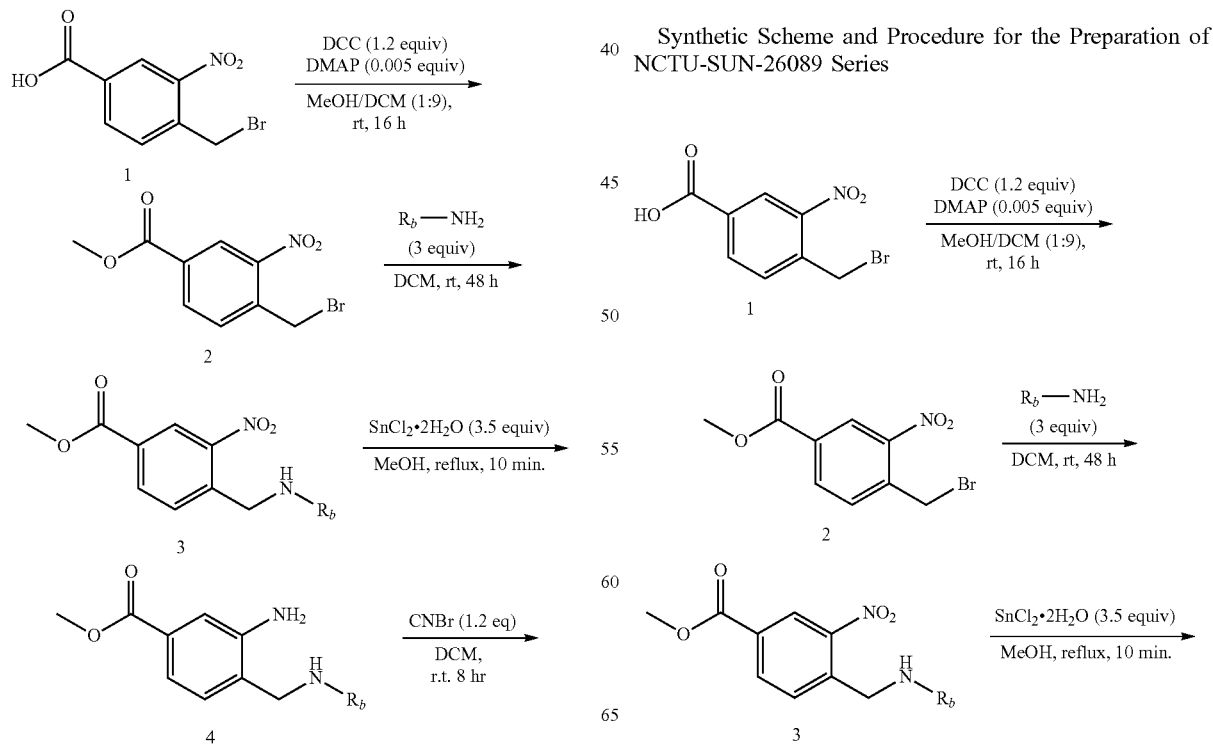
Synthetic Scheme and Procedure for the Preparation of NCTU-SUN-26089 Series

61

-continued

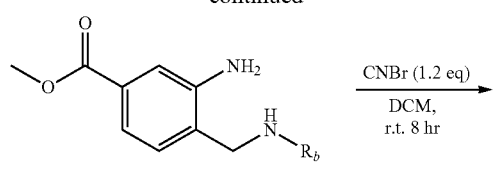

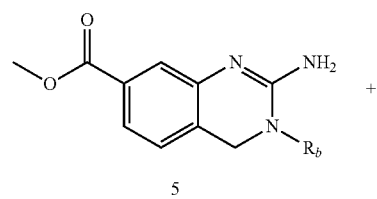

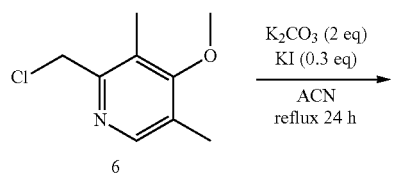

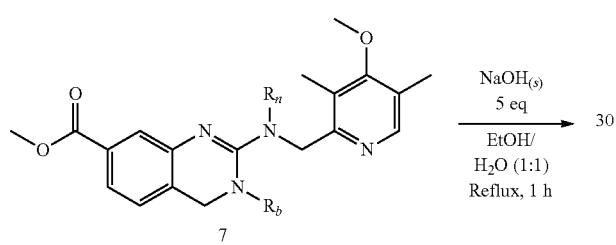

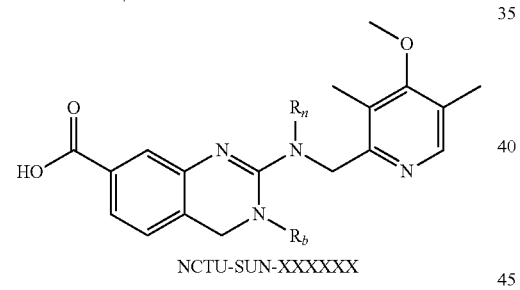

NCTU-SUN-XXXXXX $R_b$ = H, linear or branched C1-15alkyl, linear or branched C2-15alkenyl, C1-3alkoxy-C1-15alkyl-, —T'-C3-10cycloalkyl, —T'-C3-10cycloalkenyl, —T'-C6-10 aryl or —T'-C5-10heteroaryl $R_n$ = H, 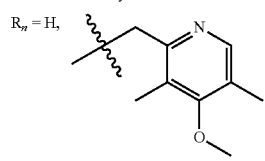

Synthetic Scheme and Procedure for the Preparation of NCTU-SUN-12082 Series

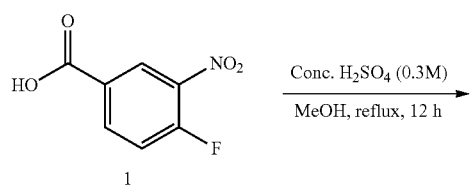

62

-continued

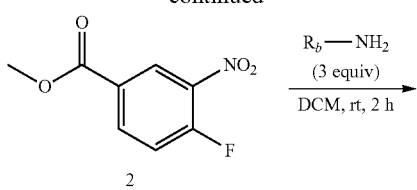

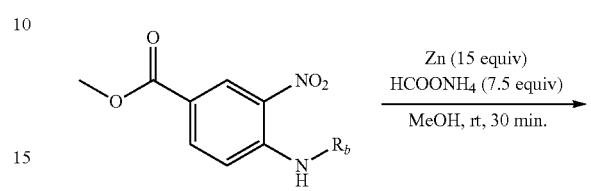

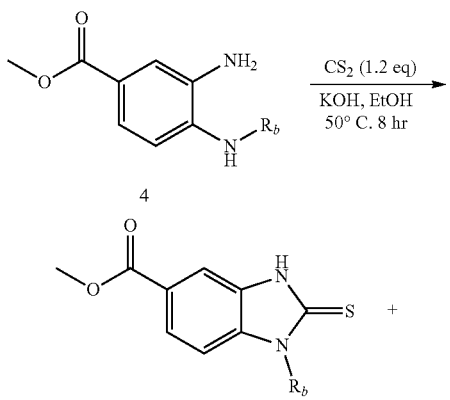

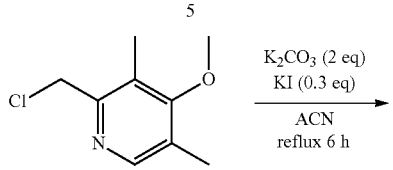

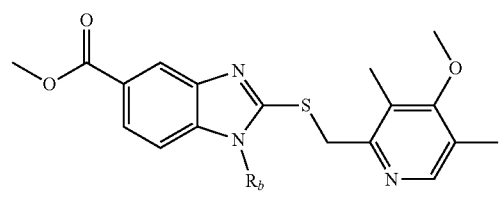

NCTU-SUN-XXXXXX $R_b$ = H, linear or branched C1-15alkyl, linear or branched C2-15alkenyl, C1-3alkoxy-C1-15alkyl-, —T'-C3-10cycloalkyl, —T'-C3-10cycloalkenyl, —T'-C6-10 aryl or —T'-C5-10heteroaryl Synthetic Scheme and Procedure for the Preparation of NCTU-SUN-12083 Series

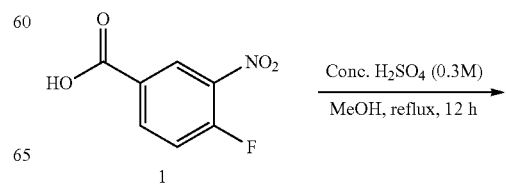

-continued
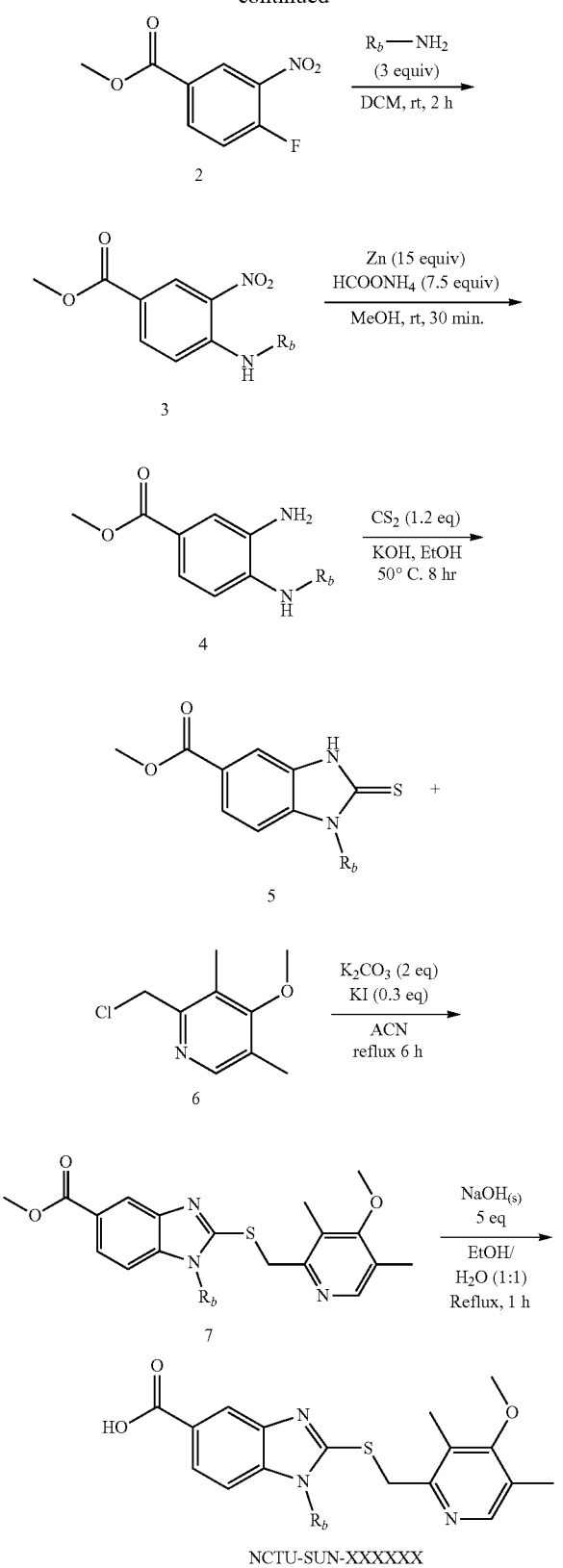
$R_b$ = H, linear or branched C1-15alkyl, linear or branched C2-15alkenyl, C1-3alkoxy-C1-15alkyl-, —T'-C3-10cycloalkyl, —T'-C3-10cycloalkenyl, —T'-C6-10 aryl or —T'-C5-10heteroaryl
Synthetic Scheme and Procedure for the Preparation of NCTU-SUN-12084
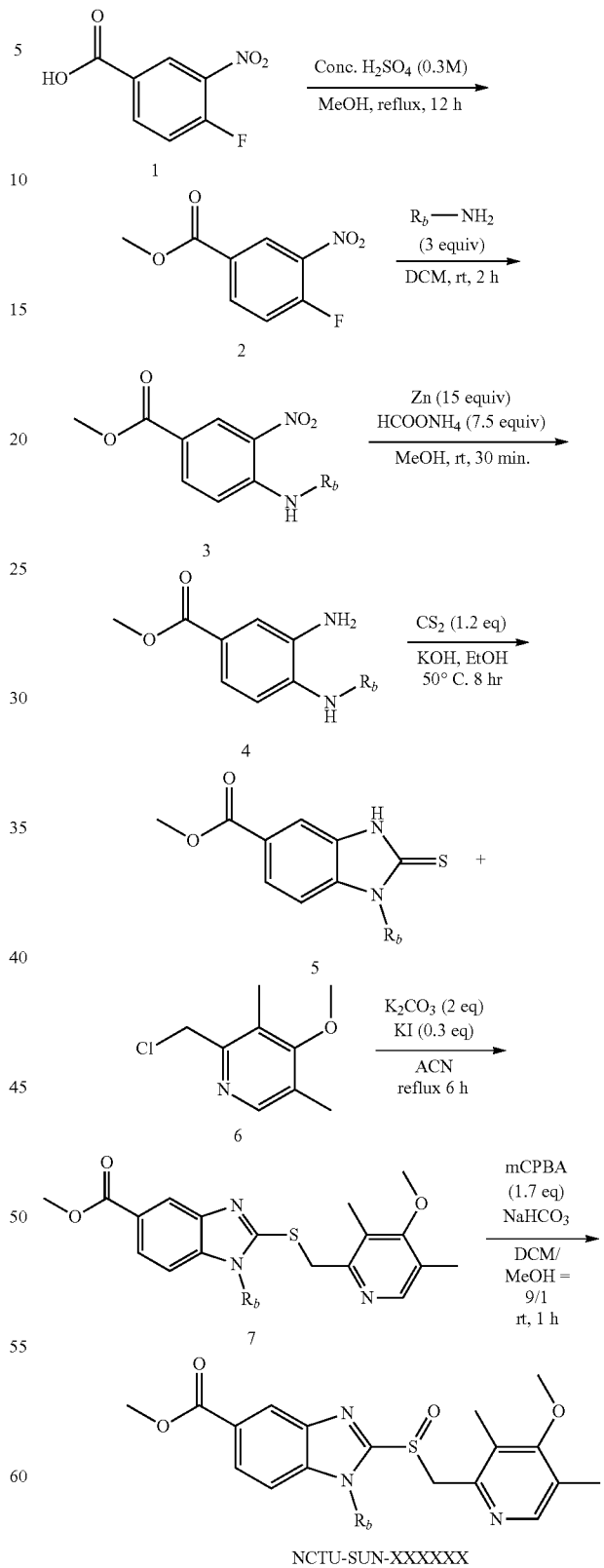
$R_b$ = H, linear or branched C1-15alkyl, linear or branched C2-15alkenyl, C1-3alkoxy-C1-15alkyl-, —T'-C3-10cycloalkyl, —T'-C3-10cycloalkenyl, —T'-C6-10 aryl or —T'-C5-10heteroaryl Synthetic Scheme and Procedure for the Preparation of NCTU-SUN-12092 Series
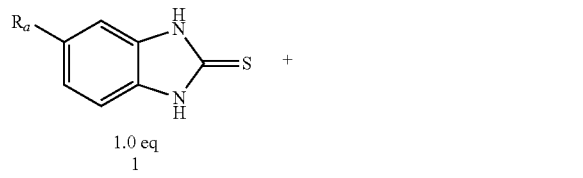
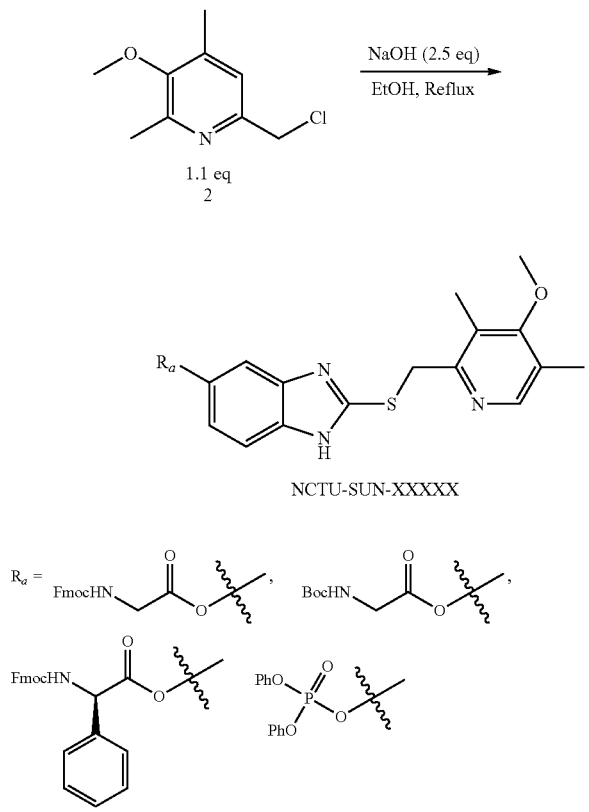
Synthetic Scheme and Procedure for the Preparation of NCTU-SUN-22138 Series
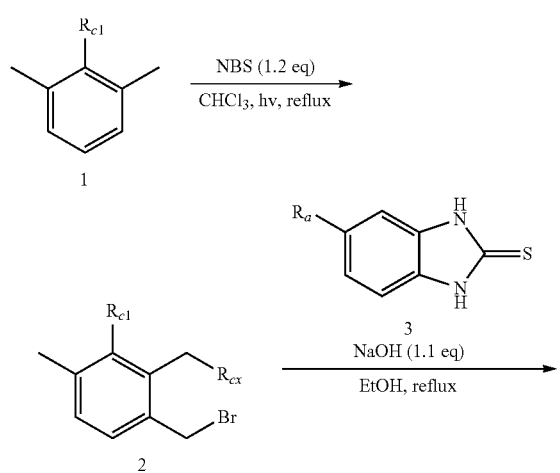
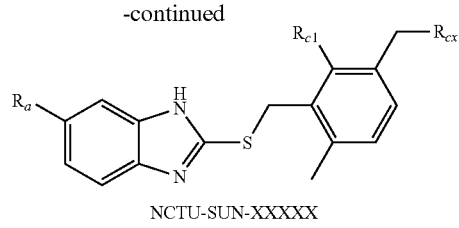
NCTU-SUN-XXXXX
$R_a$ = OH, OMe
$R_{c1}$ = OMe, OTBS
$R_{cx}$ = H, Br
Synthetic Scheme and Procedure for the Preparation of NCTU-SUN-22139
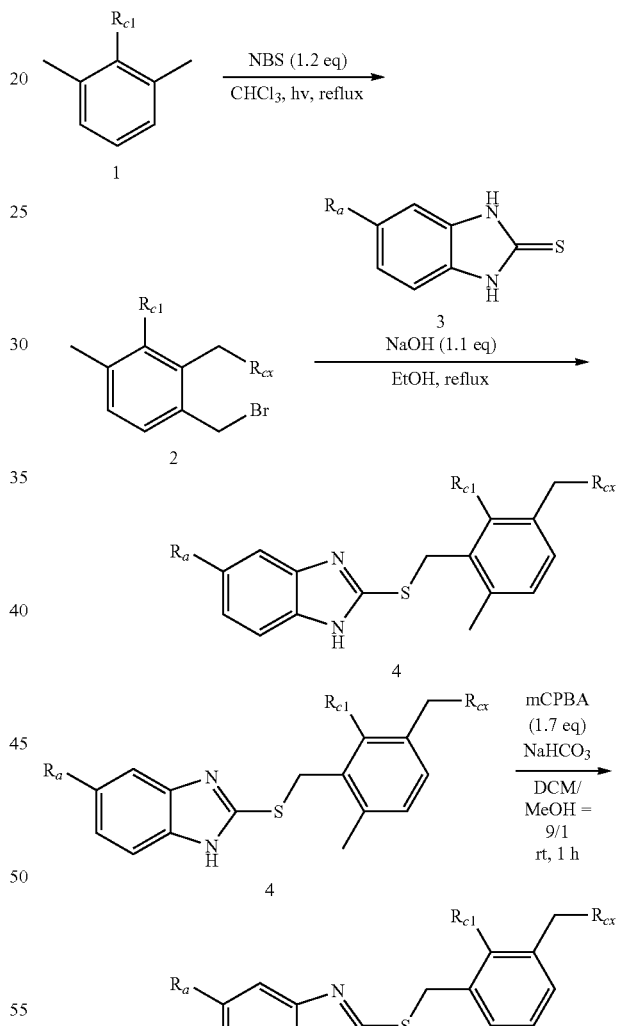
$R_a$ = OH, OMe
$R_{c1}$ = OMe, OTBS
$R_{cx}$ = H, Br, Utilities The compounds of the invention are useful for treating or preventing any disease and/or condition, wherein modulation of D-serine levels, and/or its oxidative products, is effective in ameliorating symptoms. Inhibition of the enzyme can lead to increases in D-serine levels and a reduction in the formation of toxic D-serine oxidation products. Thus, the invention provides methods for the treatment or prevention of neurological disorders and methods of enhancing learning, memory and/or cognition. The invention also provides methods for the treatment or prevention of the disease mediated by DAAO inhibition; preferably, symptom domains of schizophrenia and schizoaffective disorder, depression, Tourette Syndrome, Post-traumatic stress disorder (PTSD), Obsessive-compulsive disorder (OCD), analgesics, loss of memory and/or cognition associated with neurodegenerative diseases or loss of neuronal function characteristic of neurodegenerative diseases. In some embodiments, the symptom domains of schizophrenia and schizoaffective disorder include negative, cognitive, depressive, positive and general psychopathology symptom domains. In another embodiment, the disease associated with DAAO inhibition is mild cognitive impairment (MCI), Alzheimer's disease, Parkinson's disease or schizophrenia. In some embodiments, the disease associated with DAAO inhibition is pain, ataxia or convulsion. In some embodiments, the compounds of the invention can be used for treating or preventing loss of memory and/or cognition associated with neurodegenerative diseases (e.g., Alzheimer's disease and schizophrenia) and for preventing loss of neuronal function characteristic of neurodegenerative diseases. Further, methods are provided for the treatment or prevention of pain, ataxia and convulsion.

In some embodiment, the effective amount of the compound described herein ranges from about 0.5 mg/kg body weight to about 20 g/kg, about 1 mg/kg body weight to about 20 g/kg, about 2 mg/kg body weight to about 20 g/kg, about 4 mg/kg body weight to about 20 g/kg, about 6 mg/kg body weight to about 20 g/kg, about 8 mg/kg body weight to about 20 g/kg, about 10 mg/kg body weight to about 20 g/kg, about 12 mg/kg body weight to about 20 g/kg, about 14 mg/kg body weight to about 20 g/kg, about 16 mg/kg body weight to about 20 g/kg, about 0.5 mg/kg body weight to about 15 g/kg, about 0.5 mg/kg body weight to about 12 g/kg, about 0.5 mg/kg body weight to about 10 g/kg, about 0.5 mg/kg body weight to about 8 g/kg, about 0.5 mg/kg body weight to about 6 g/kg, about 2 mg/kg body weight to about 15 g/kg, about 2 mg/kg body weight to about 12 g/kg, about 2 mg/kg body weight to about 10 g/kg, about 2 mg/kg body weight to about 7 g/kg, about 2 mg/kg body weight to about 5 g/kg, about 5 mg/kg body weight to about 15 g/kg or about 5 mg/kg body weight to about 10 g/kg body weight.

Pharmaceutical Composition

Another aspect of the present invention provides pharmaceutical compositions which comprises a compound of Formula I (or a pharmaceutically acceptable salt or solvate thereof) and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

For topical applications, the active ingredient or a pharmaceutical composition thereof can be formulated in a suitable ointment containing the active component suspended or dissolved in one or more carriers. Carriers for topical administration of the active ingredient or a pharmaceutical composition thereof include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the active ingredient or a pharmaceutical composition thereof suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the active ingredient or a pharmaceutical composition thereof. Those additional agents can be administered sequentially in any order, as part of a multiple dosage regimen, from the active ingredient or a pharmaceutical composition thereof (consecutive or intermittent administration). Alternatively, those agents can be part of a single dosage form, mixed together with the active ingredient or a pharmaceutical composition thereof (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, t the active ingredient or a pharmaceutical composition thereof of this invention can be combined with various sweetening agents, flavoring agents, coloring agents, emulsifying agents and/or suspending agents, as well as such diluents as water, ethanol, propylene glycol, glycerin and various like combinations thereof.

The term "parenteral" as used herein refers to modes of administration which include intravenous, intramuscular, intraperitoneal, intrasternal, subcutaneous, intramedullary and intraarticular injection and infusion. A pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

Administration by slow infusion is particularly useful when intrathecal or epidural routes are employed. A number of implantable or body-mountable pumps useful in delivering compound at a regulated rate are known in the art.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Compositions for rectal or vaginal administration are preferably suppositories which can be prepared by mixing the active ingredient or a pharmaceutical composition thereof with suitable non-irritating excipients or carriers such as cocoa butter, polyethylene glycol or a suppository wax which are solid at room temperature but liquid at body temperature and therefore melt in the rectum or vaginal cavity and release the drugs.

Other pharmaceutically acceptable carriers include, but are not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. 1995.

Without further elaboration, it is believed that one skilled in the art can utilize the present invention to its fullest extent on the basis of the preceding description. The following examples are, therefore, to be construed as merely illustrative and not a limitation of the scope of the present invention in any way.

EXAMPLES

Example 1-1 NCTU-SUN-21122: (2-(((4-methoxy-3,5-dimethylpyridin-2-yl)methyl)sulfinyl)-1H-benzo[d]imidazol-5-yl acetate)

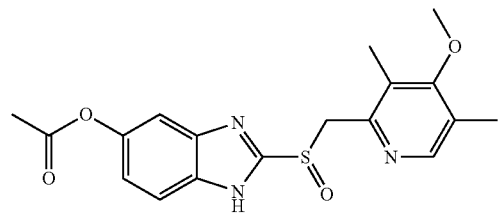 [SMILES: COc1c(C)cnc(CS(=O)c2nc3cc(OC(C)=O)ccc3[nH]2)c1C]

To a solution of RS-D7 (0.1 g, 0.30 mmol) in DCM (10 mL) was added NaOH (0.90 mmol) and the reaction mixture was stirred for 5-10 minutes in the nitrogen. Then acetyl chloride (0.60 mmol) was added at 0° C. (in the ice bath). After stirring for 5-10 minutes, the reaction was allowed to warm to room temperature and stirred further for 1 hour. The reaction was extracted with ethyl acetate and pure water. The organic layer was dried over MgSO$_4$, filtered and concentrated to give the reaction mixture. The reaction mixture was purified by silica-gel column chromatography to obtain the pure product.

$^1$H NMR (400 MHz, Acetone-d$_6$) δ 8.17 (s, 1H), 7.68 (d, J=8.8 Hz, 1H), 7.44 (s, 1H), 7.09 (d, J=8.7 Hz, 1H), 4.71 (s, 2H), 3.75 (s, 3H), 2.29 (s, 3H), 2.24 (s, 6H).

LRMS (ESI$^+$) m/z: 374.1 (M+H)$^+$.

Example 1-2 NCTU-SUN-21124: (2-(((4-methoxy-3,5-dimethylpyridin-2-yl)methyl)sulfinyl)-1H-benzo[d]imidazol-5-yl benzoate)

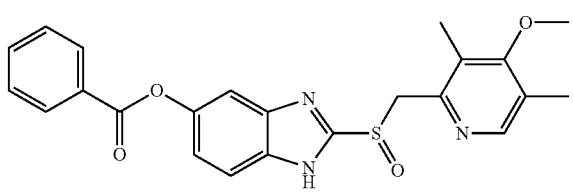 [SMILES: COc1c(C)cnc(CS(=O)c2nc3cc(OC(=O)c4ccccc4)ccc3[nH]2)c1C]

Except that acetyl chloride is replaced by benzyl chloride, the other reactants and preparation steps are similar to those described in Example 1 to afford the title compound.

$^1$H NMR (400 MHz, Acetone-d$_6$) δ 8.24 (s, 1H), 8.22 (d, J=1.4H z, 1H), 8.18 (s, 1H), 7.78-7.71 (m, 2H), 7.65-7.59 (m, 3H), 7.27 (dd, J=8.8, 2.2 Hz, 1H), 4.74 (s, 2H), 3.76 (s, 3H), 2.26 (s, 3H), 2.25 (s, 3H).

LRMS (ESI$^+$) m/z: 436.2 (M+H)$^+$.

Example 1-3 NCTU-SUN-26096: (2-(((4-methoxy-3,5-dimethylpyridin-2-yl)methyl)sulfinyl)-1H-benzo[d]imidazol-5-yl butyrate)

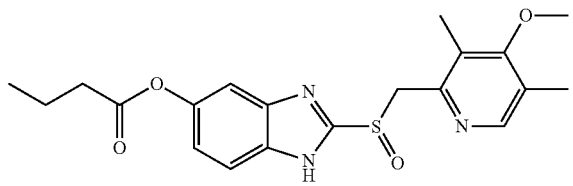 [SMILES: CCCC(=O)Oc1ccc2[nH]c(S(=O)Cc3ncc(C)c(OC)c3C)nc2c1]

Except that acetyl chloride is replaced by butyryl chloride, the other reactants and preparation steps are similar to those described in Example 1 to afford the title compound.

$^1$H NMR (400 MHz, Acetone-d$_6$) δ 8.17 (s, 1H), 7.68 (d, J=8.7 Hz, 1H), 7.43 (d, J=2.0 Hz, 1H), 7.08 (dd, J=8.7, 2.1 Hz, 1H), 4.72 (s, 1H), 3.74 (s, 3H), 2.60 (t, J=7.3 Hz, 2H), 2.24 (s, 6H), 1.77 (h, J=7.3 Hz, 3H), 1.04 (t, J=7.4 Hz, 3H).

LRMS (ESI$^+$) m/z: 402.1 (M+H)$^+$.

Example 1-4 NCTU-SUN-26097: (2-(((4-methoxy-3,5-dimethylpyridin-2-yl)methyl)sulfinyl)-1H-benzo[d]imidazol-5-yl cyclohexanecarboxylate)

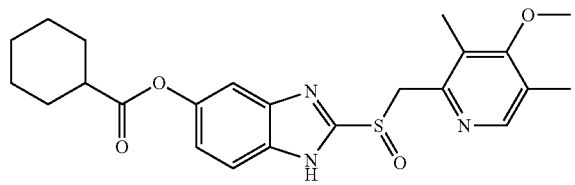 [SMILES: COc1c(C)cnc(CS(=O)c2nc3cc(OC(=O)C4CCCCC4)ccc3[nH]2)c1C]

Except that acetyl chloride is replaced by hexahydrobenzoyl chloride, the other reactants and preparation steps are similar to those described in Example 1 to afford the title compound.

$^1$H NMR (400 MHz, Acetone-d$_6$) δ 8.17 (s, 1H), 7.68 (d, J=8.7 Hz, 1H), 7.42 (s, 1H), 7.07 (d, J=8.7 Hz, 1H), 4.72 (s, 2H), 3.75 (s, 3H), 2.64 (t, J=11.1 Hz, 1H), 2.24 (s, 7H), 1.88-1.76 (m, 2H), 1.69 (d, J=12.1 Hz, 1H), 1.65-1.52 (m, 3H), 1.42 (q, J=11.8 Hz, 2H).

LRMS (ESI$^+$) m/z: 442.2 (M+H)$^+$.

Example 1-5 NCTU-SUN-26098: (2-(((4-methoxy-3,5-dimethylpyridin-2-yl)methyl)sulfinyl)-1H-benzo[d]imidazol-5-yl 4-butylbenzoate)

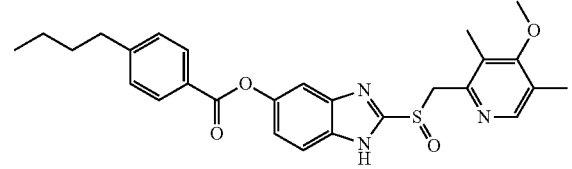 [SMILES: CCCCc1ccc(C(=O)Oc2ccc3[nH]c(S(=O)Cc4ncc(C)c(OC)c4C)nc3c2)cc1]

Except that acetyl chloride is replaced by 4-Butylbenzoyl chloride, the other reactants and preparation steps are similar to those described in Example 1 to afford the title compound.

$^1$H NMR (400 MHz, Acetone-d$_6$) δ 8.18 (s, 1H), 8.13 (d, J=8.2 Hz, 2H), 7.75 (d, J=8.8 Hz, 1H), 7.61 (s, 1H), 7.45 (d, J=8.2 Hz, 2H), 7.25 (d, J=8.7 Hz, 1H), 4.74 (s, 2H), 3.76 (s, 3H), 2.25 (d, J=6.2 Hz, 6H), 1.66 (q, J=7.7 Hz, 3H), 1.47-1.28 (m, 3H), 0.95 (t, J=7.3 Hz, 3H).

LRMS (ESI$^+$) m/z: 492.1 (M+H)$^+$.

Example 1-6 NCTU-SUN-21127: (2-(((4-methoxy-3,5-dimethylpyridin-2-yl)methyl)sulfinyl)-1H-benzo[d]imidazol-5-yl 3-methylbenzoate)

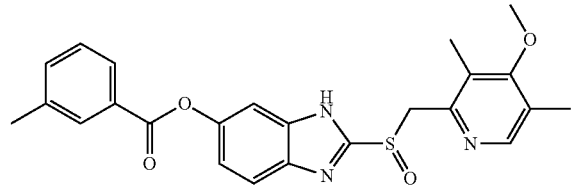

Except that acetyl chloride is replaced by m-Toluoyl chloride, the other reactants and preparation steps are similar to those described in Example 1 to afford the title compound.

¹H NMR (400 MHz, Acetone-d₆) δ 8.18 (s, 1H), 8.06-7.99 (m, 2H), 7.74 (d, J=8.8 Hz, 1H), 7.61 (d, J=2.2 Hz, 1H), 7.56 (d, J=7.5 Hz, 1H), 7.49 (t, J=7.6 Hz, 1H), 7.25 (dd, J=8.7, 2.2 Hz, 1H), 4.76 (d, J=3.2 Hz, 2H), 3.74 (s, 3H), 2.47 (s, 3H), 2.25 (s, 3H), 2.23 (s, 3H).

LRMS (ESI⁺) m/z: 450.1 (M+H)⁺.

Example 1-7 NCTU-SUN-27076: 2-(((4-methoxy-3,5-dimethylpyridin-2-yl)methyl)sulfinyl)-1H-benzo[d]imidazol-5-yl hexanoate

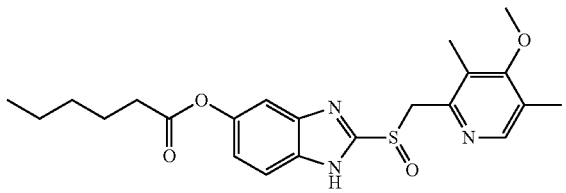 [SMILES: CCCCCC(=O)Oc1ccc2[nH]c(S(=O)Cc3ncc(C)c(OC)c3C)nc2c1]

Except that acetyl chloride is replaced by hexanoyl chloride, the other reactants and preparation steps are similar to those described in Example 1 to afford the title compound.

¹H NMR (400 MHz, Acetone-d₆) δ 8.17 (s, 1H), 7.68 (d, J=8.7 Hz, 1H), 7.44 (s, 1H), 7.09 (d, J=8.8 Hz, 1H), 4.72 (s, 2H), 3.74 (s, 3H), 2.62 (t, J=7.4 Hz, 2H), 2.24 (s, 6H), 1.75 (p, J=7.3 Hz, 2H), 1.41 (h, J=7.9, 7.5 Hz, 6H), 0.94 (t, J=6.7 Hz, 3H).

LRMS (ESI⁺) m/z: 430.2 (M+H)⁺.

Example 1-8 NCTU-SUN-27077: 2-(((4-methoxy-3,5-dimethylpyridin-2-yl)methyl)sulfinyl)-1H-benzo[d]imidazol-5-yl isobutyrate

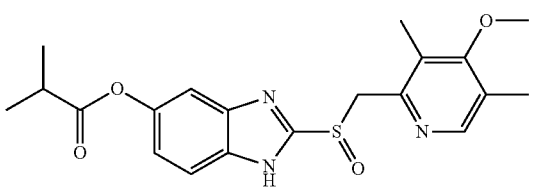

Except that acetyl chloride is replaced by isobutyryl chloride, the other reactants and preparation steps are similar to those described in Example 1 to afford the title compound.

¹H NMR (400 MHz, Acetone-d₆) δ 8.17 (s, 1H), 7.69 (d, J=8.7 Hz, 1H), 7.44 (d, J=2.1 Hz, 1H), 7.08 (dd, J=8.7, 2.1 Hz, 1H), 4.71 (s, 2H), 3.75 (s, 3H), 2.89-2.84 (m, 1H), 2.24 (d, J=2.4 Hz, 6H), 1.31 (d, J=7.0 Hz, 6H).

LRMS (ESI⁺) m/z: 402.2 (M+H)⁺.

Example 1-9 NCTU-SUN-27078: (2-(((4-methoxy-3,5-dimethylpyridin-2-yl)methyl)sulfinyl)-1H-benzo[d]imidazol-5-yl cyclohex-3-ene-1-carboxylate)

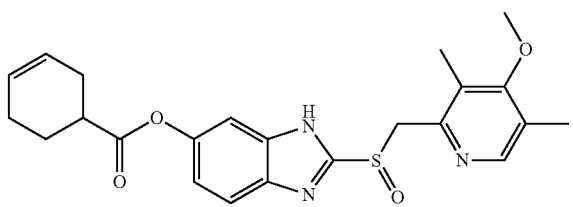 [SMILES: COc1c(C)cnc(CS(=O)c2nc3ccc(OC(=O)C4CC=CCC4)cc3[nH]2)c1C]

Except that acetyl chloride is replaced by cyclohex-3-enecarbonyl chloride, the other reactants and preparation steps are similar to those described in Example 1 to afford the title compound.

¹H NMR (400 MHz, Acetone-d₆) δ 8.17 (s, 1H), 7.66 (d, J=8.2 Hz, 1H), 7.42 (s, 1H), 7.07 (dd, J=8.7, 1.8 Hz, 1H), 5.74 (s, 2H), 4.78 (d, J=13.6 Hz, 1H), 4.73 (d, J=13.7 Hz, 1H), 3.70 (s, 3H), 2.96-2.80 (m, 2H), 2.54-2.30 (m, 3H), 2.22 (d, J=2.6 Hz, 6H), 1.95-1.72 (m, 2H).

LRMS (ESI⁺) m/z: 440.1 (M+H)⁺.

Example 1-10 NCTU-SUN-27079: 2-(((4-methoxy-3,5-dimethylpyridin-2-yl)methyl)sulfinyl)-1H-benzo[d]imidazol-5-ylcyclohex-3-enecarboxylate

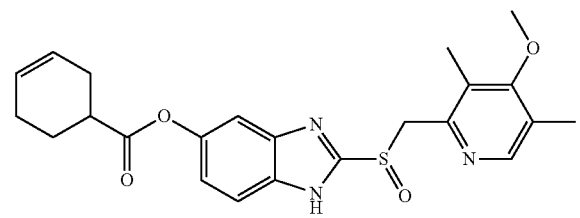 [SMILES: COc1c(C)cnc(CS(=O)c2nc3cc(OC(=O)C4CC=CCC4)ccc3[nH]2)c1C]

Except that acetyl chloride is replaced by 2-methylbenzoyl chloride, the other reactants and preparation steps are similar to those described in Example 1 to afford the title compound.

¹H NMR (400 MHz, Acetone-d₆) δ 8.20-8.17 (m, 2H), 7.76 (d, J=8.7 Hz, 1H), 7.63 (d, J=2.2 Hz, 1H), 7.57 (td, J=7.5, 1.5 Hz, 1H), 7.42 (dt, J=7.4, 3.4 Hz, 2H), 7.27 (dd, J=8.7, 2.2 Hz, 1H), 4.74 (s, 2H), 3.77 (s, 3H), 2.67 (s, 3H), 2.26 (s, 4H), 2.25 (s, 4H).

LRMS (ESI⁺) m/z: 450.1 (M+H)⁺.

Example 1-11 NCTU-SUN-28087: (2-(((4-methoxy-3,5-dimethylpyridin-2-yl)methyl)sulfinyl)-1H-benzo[d]imidazol-5-yl 4-methylbenzoate)

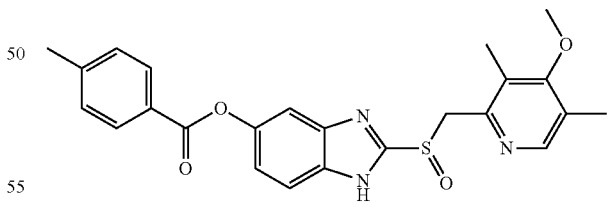

Except that acetyl chloride is replaced by 4-methylbenzoyl chloride, the other reactants and preparation steps are similar to those described in Example 1 to afford the title compound.

¹H NMR (400 MHz, Acetone-d₆) δ 8.18 (s, 1H), 8.10 (d, J=8.1 Hz, 2H), 7.73 (d, J=8.7 Hz, 1H), 7.60 (s, 1H), 7.42 (d, J=7.9 Hz, 2H), 7.24 (d, J=7.1 Hz, 1H), 4.82-4.69 (m, 2H), 3.73 (s, 3H), 2.47 (s, 3H), 2.24 (s, 3H), 2.23 (s, 3H).

LRMS (ESI⁺) m/z: 450.1 (M+H)⁺.

Example 1-12 NCTU-SUN-28091: (2-(((4-methoxy-3,5-dimethylpyridin-2-yl)methyl)sulfinyl)-1H-benzo[d]imidazol-5-yl 2-nitrobenzoate)

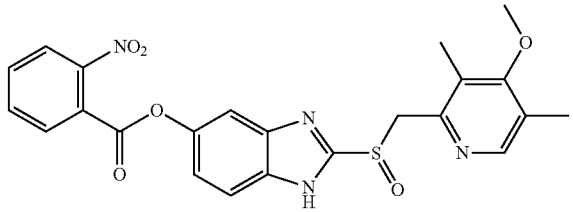 [SMILES: COc1c(C)cnc(CS(=O)c2nc3cc(OC(=O)c4ccccc4[N+](=O)[O-])ccc3[nH]2)c1C]

Except that acetyl chloride is replaced by 2-nitrobenzoyl chloride, the other reactants and preparation steps are similar to those described in Example 1 to afford the title compound.

$^1$H NMR (400 MHz, Acetone-$d_6$) δ 8.16 (d, J 5.9 Hz, 2H), 8.10 (d, J=7.3 Hz, 1H), 7.96 (td, J=7.5, 1.8 Hz, 1H), 7.91 (td, J=7.8, 1.8 Hz, 1H), 7.74 (dd, J=8.7, 1.5 Hz, 1H), 7.61 (s, 1H), 7.24 (d, J=8.4 Hz, 1H), 4.75 (dd, J=13.7, 5.7 Hz, 2H), 3.69 (s, 3H), 2.20 (s, 6H).

LRMS (ESI$^+$) m/z: 481.2 (M+H)$^+$.

Example 1-13 NCTU-SUN-28092: (2-(((4-methoxy-3,5-dimethylpyridin-2-yl)methyl)sulfinyl)-1H-benzo[d]imidazol-5-yl cyclopropanecarboxylate)

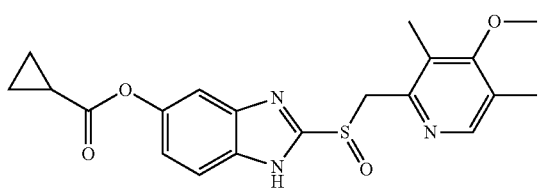 [SMILES: COc1c(C)cnc(CS(=O)c2nc3cc(OC(=O)C4CC4)ccc3[nH]2)c1C]

Except that acetyl chloride is replaced by cyclopropanecarbonyl chloride, the other reactants and preparation steps are similar to those described in Example 1 to afford the title compound.

$^1$H NMR (400 MHz, Acetone-$d_6$) δ 8.17 (s, 1H), 7.67 (d, J=8.7 Hz, 1H), 7.45 (d, J=2.2 Hz, 1H), 7.09 (dd, J=8.8, 2.2 Hz, 1H), 4.73 (dd, J=13.7, 2.5 Hz, 2H), 3.73 (s, 3H), 2.23 (s, 6H), 1.92 (dt, J=12.5, 6.3 Hz, 1H), 1.08 (s, 2H), 1.06 (s, 2H).

LRMS (ESI$^+$) m/z: 400.2 (M+H)$^+$.

Example 1-14 NCTU-SUN-28093: (2-(((4-methoxy-3,5-dimethylpyridin-2-yl)methyl)sulfinyl)-1H-benzo[d]imidazol-5-yl 2-ethylbutanoate)

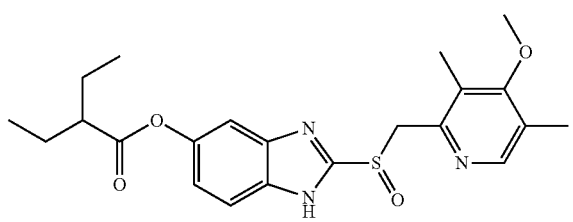 [SMILES: CCC(CC)C(=O)Oc1ccc2[nH]c(S(=O)Cc3ncc(C)c(OC)c3C)nc2c1]

Except that acetyl chloride is replaced by 2-ethylbutanoyl chloride, the other reactants and preparation steps are similar to those described in Example 1 to afford the title compound.

$^1$H NMR (400 MHz, Acetone-$d_6$) δ 8.15 (s, 1H), 7.64 (d, J=8.7 Hz, 1H), 7.39 (d, J=2.2 Hz, 1H), 7.05 (dd, J=8.8, 2.2 Hz, 1H), 4.81 (dd, J=28.8, 13.7 Hz, 2H), 3.65 (s, 3H), 2.51 (tt, J=8.6, 5.5 Hz, 1H), 2.19 (s, 3H), 2.18 (s, 3H), 1.74 (m, 4H), 1.04 (t, 7.5 Hz, 6H).

LRMS (ESI$^+$) m/z: 430.2 (M+H)$^+$.

Example 1-15 NCTU-SUN-28094: (2-(((4-methoxy-3,5-dimethylpyridin-2-yl)methyl)sulfinyl)-1H-benzo[d]imidazol-5-yl 2-phenylacetate)

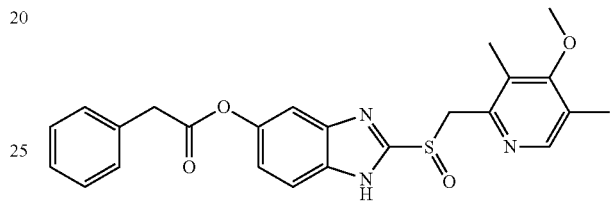

Except that acetyl chloride is replaced by 2-phenylacetyl chloride, the other reactants and preparation steps are similar to those described in Example 1 to afford the title compound.

$^1$H NMR (400 MHz, Acetone-$d_6$) δ 8.16 (s, 1H), 7.66 (d, J=8.8 Hz, 1H), 7.41 (m, 5H), 7.30 (m, 1H), 7.06 (dd, J=8.8, 2.2 Hz, 1H), 4.74 (dd, J=13.7, 19.2 Hz, 2H), 3.98 (s, 2H), 3.70 (s, 3H), 2.21 (s, 6H).

LRMS (ESI$^+$) m/z: 450.2 (M+H)$^+$.

Example 1-16 NCTU-SUN-28095: (2-(((4-methoxy-3,5-dimethylpyridin-2-yl)methyl)sulfinyl)-1H-benzo[d]imidazol-5-yl 3,5,5-trimethylhexanoate

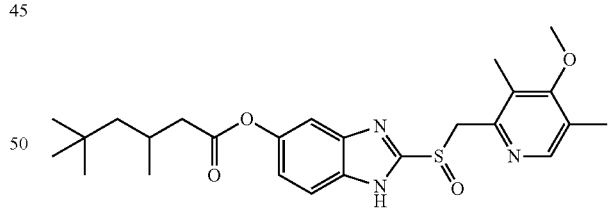

Except that acetyl chloride is replaced by 3,5,5-trimethylhexanoyl chloride, the other reactants and preparation steps are similar to those described in Example 1 to afford the title compound.

$^1$H NMR (400 MHz, Acetone-$d_6$) δ 8.15 (s, 1H), 7.63 (d, J=8.8 Hz, 1H), 7.40 (s, 1H), 7.09 (dd, J=8.8, 2.2 Hz, 1H), 4.80 (dd, J=29.0, 13.7 Hz, 2H), 3.65 (s, 3H), 2.61 (dd, J=15.0, 6.2 Hz, 1H), 2.44 (dd, J=15.0, 7.9 Hz, 1H), 2.19 (m, 1H), 2.19 (s, 3H), 2.18 (s, 3H), 1.43 (dd, J=14.1, 4.0 Hz, 1H), 1.23 (dd, J=14.1, 6.5 Hz, 1H), 1.12 (d, J=6.7 Hz, 3H), 0.97 (s, 9H).

LRMS (ESI$^+$) m/z: 472.1 (M+H)$^+$.

Example 1-17 NCTU-SUN-28096: (2-(((5-methoxy-4,6-dimethylpyridin-2-yl)methyl)sulfinyl)-1H-benzo[d]imidazol-5-yl 2-ethoxybenzoate)

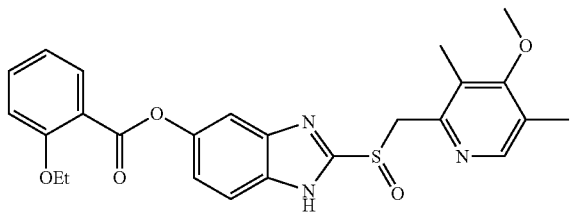 [SMILES: CCOc1ccccc1C(=O)Oc1ccc2[nH]c(S(=O)Cc3ncc(C)c(OC)c3C)nc2c1]

Except that acetyl chloride is replaced by 2-ethoxybenzoyl chloride, the other reactants and preparation steps are similar to those described in Example 1 to afford the title compound.

$^1$H NMR (400 MHz, Acetone-$d_6$) δ 8.18 (s, 1H), 7.92 (dd, J=7.8, 1.8 Hz, 1H), 7.71 (d, J=8.8, 1H), 7.58 (m, 2H), 7.22 (dd, J=8.8, 2.3 Hz, 1H), 7.18 (d, J=8.5, 1H), 4.80 (dd, J=23.0, 13.7 Hz, 2H), 4.19 (q, J=7.0 Hz, 2H), 3.69 (s, 3H), 2.21 (s, 3H), 2.20 (s, 3H), 1.44 (t, J=7.1 Hz, 3H)

LRMS (ESI$^+$) m/z: 480.1 (M+H)$^+$.

Example 1-18 NCTU-SUN-21123: (2-(((4-methoxy-3,5-dimethylpyridin-2-yl)methyl)sulfinyl)-1H-benzo[d]imidazol-5-yl propionate)

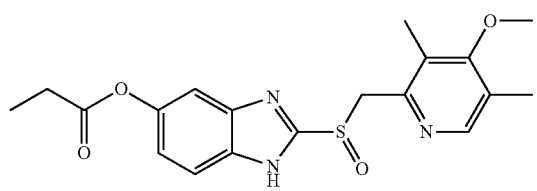 [SMILES: CCC(=O)Oc1ccc2[nH]c(S(=O)Cc3ncc(C)c(OC)c3C)nc2c1]

Except that acetyl chloride is replaced by propionyl chloride, the other reactants and preparation steps are similar to those described in Example 1 to afford the title compound.

$^1$H NMR (400 MHz, Acetone-$d_6$) δ 8.17 (s, 1H), 7.68 (d, J=8.8 Hz, 1H), 7.44 (s, 1H), 7.09 (d, J=8.7 Hz, 1H), 4.73 (s, 2H), 3.74 (s, 3H), 2.64 (d, J=7.6 Hz, 2H), 2.24 (s, 6H), 1.22 (t, J=7.6 Hz, 3H).

LRMS (ESI$^+$) m/z: 388.2 (M+H)$^+$.

Example 1-19 NCTU-SUN-21125: (2-(((4-methoxy-3,5-dimethylpyridin-2-yl)methyl)sulfinyl)-1H-benzo[d]imidazol-5-yl 4-chlorobenzoate)

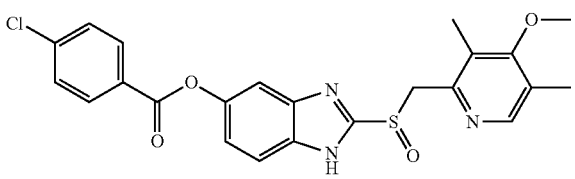 [SMILES: COc1c(C)cnc(CS(=O)c2nc3cc(OC(=O)c4ccc(Cl)cc4)ccc3[nH]2)c1C]

Except that acetyl chloride is replaced by 4-chlorobenzoyl chloride, the other reactants and preparation steps are similar to those described in Example 1 to afford the title compound.

$^1$H NMR (400 MHz, Acetone-$d_6$) δ 8.33-8.12 (m, 1H), 7.76 (d, J=8.7 Hz, 0H), 7.72-7.61 (m, 1H), 7.27 (dd, J=8.7, 2.2 Hz, 0H), 4.74 (s, 1H), 3.76 (s, 1H), 2.25 (d, J=6.00 Hz, 2H).

LRMS (ESI$^+$) m/z: 470.2 (M+H)$^+$.

Example 1-20 NCTU-SUN-21126: (2-(((4-methoxy-3,5-dimethylpyridin-2-yl)methyl)sulfinyl)-1H-benzo[d]imidazol-5-yl 3-nitrobenzoate)

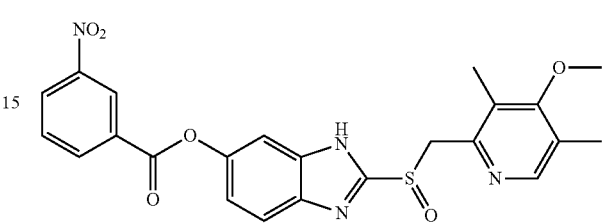

Except that acetyl chloride is replaced by 3-nitrobenzoyl chloride, the other reactants and preparation steps are similar to those described in Example 1 to afford the title compound.

$^1$H NMR (400 MHz, Acetone-$d_6$) δ 8.95 (t, J=2.0 Hz, 1H), 8.64-8.56 (m, 2H), 8.18 (s, 1H), 7.95 (t, J=8.0 Hz, 1H), 7.77 (d, J=8.8 Hz, 1H), 7.69 (d, J=2.2 Hz, 1H), 7.32 (dd, J=8.8, 2.2 Hz, 1H), 4.76 (s, 2H), 3.74 (s, 3H), 2.24 (d, J=7.0 Hz, 6H).

LRMS (ESI$^+$) m/z: 481.2 (M+H)$^+$.

Example 1-21 NCTU-SUN-21128: 2-(((4-methoxy-3,5-dimethylpyridin-2-yl)methyl)sulfinyl)-1H-benzo[d]imidazol-5-yl heptanoate

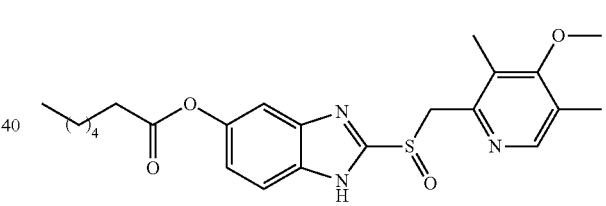

Except that acetyl chloride is replaced by heptanoyl chloride, the other reactants and preparation steps are similar to those described in Example 1 to afford the title compound.

$^1$H NMR (400 MHz, Acetone-$d_6$) δ 8.17 (s, 1H), 7.67 (s, 1H), 7.43 (d, J=2.2 Hz, 1H), 7.08 (dd, J=8.8, 2.1 Hz, 1H), 4.72 (s, 2H), 3.74 (s, 3H), 2.62 (s, 2H), 2.24 (s, 6H), 1.81-1.68 (m, 3H), 1.53-1.25 (m, 8H).

LRMS (ESI$^+$) m/z: 444.3 (M+H)$^+$.

Example 1-22 NCTU-SUN-21129: (2-(((4-methoxy-3,5-dimethylpyridin-2-yl)methyl)sulfinyl)-1H-benzo[d]imidazo-5-yl 4-fluorobenzoate)

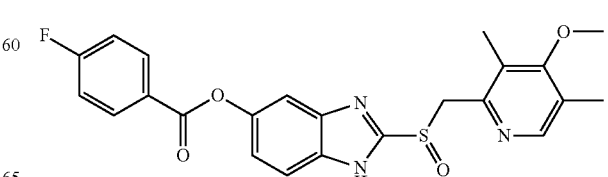

Except that acetyl chloride is replaced by 4-fluorobenzoyl chloride, the other reactants and preparation steps are similar to those described in Example 1 to afford the title compound.

$^1$H NMR (400 MHz, Acetone-$d_6$) δ 8.30 (dd, J=8.6, 5.6 Hz, 1H), 7.75 (d, J=8.7 Hz, 1H), 7.38 (t, J=8.8 Hz, 1H), 7.26 (d, J=8.7 Hz, 1H), 2.24 (d, J=6.5 Hz, 3H).

LRMS (ESI$^+$) m/z: 454.1 (M+H)$^+$.

Example 1-23 NCTU-SUN-21130: (2-(((4-methoxy-3,5-dimethylpyridin-2-yl)methyl)sulfinyl)-1H-benzo[d]imidazol-5-yl (Z)-2-methylbut-2-enoate)

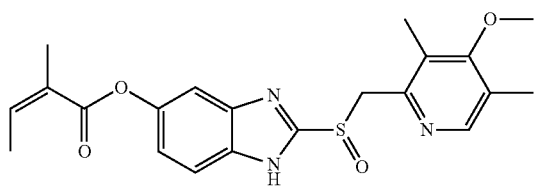 [SMILES: C/C=C(/C)C(=O)Oc1ccc2[nH]c(S(=O)Cc3ncc(C)c(OC)c3C)nc2c1]

Except that acetyl chloride is replaced by (Z)-2-methyl-but-2-enoyl chloride, the other reactants and preparation steps are similar to those described in Example 1 to afford the title compound.

$^1$H NMR (400 MHz, Acetone-$d_6$) δ 8.18 (s, 1H), 7.68 (s, 1H), 7.46 (d, J=2.2 Hz, 1H), 7.19-7.01 (m, 2H), 4.72 (s, 2H), 3.75 (s, 3H), 2.24 (d, J=2.6 Hz, 6H), 1.95 (s, 3H), 1.91 (d, J=7.2 Hz, 3H).

LRMS (ESI$^+$) m/z: 414.2 (M+H)$^+$.

Example 1-24 NCTU-SUN-21131: (2-(((4-methoxy-3,5-dimethylpyridin-2-yl)methyl)sulfinyl)-1H-benzo[d]imidazol-5-yl 2-chloropropanoate)

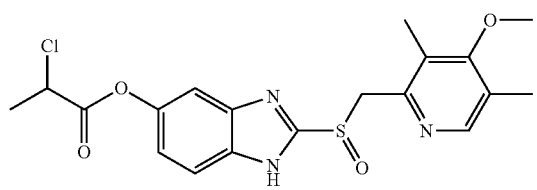 [SMILES: COc1c(C)cnc(CS(=O)c2nc3cc(OC(=O)C(C)Cl)ccc3[nH]2)c1C]

Except that acetyl chloride is replaced by 2-chloropropanoyl chloride, the other reactants and preparation steps are similar to those described in Example 1 to afford the title compound.

$^1$H NMR (400 MHz, Acetone-$d_6$) δ 8.16 (s, 1H), 7.71 (d, J=8.7 Hz, 1H), 7.54-7.40 (m, 1H), 7.13 (dd, J=8.7, 2.0 Hz, 1H), 4.91 (d, J=6.8 Hz, 1H), 4.75 (d, J=4.1 Hz, 2H), 3.71 (s, 4H), 2.22 (s, 6H), 1.83 (d, J=6.8 Hz, 4H).

LRMS (ESI$^+$) m/z: 422.1 (M+H)$^+$.

Example 1-25 NCTU-SUN-21132: tert-butyl (2-(((4-methoxy-3,5-dimethylpyridin-2-yl)methyl)sulfinyl)-1H-benzo[d]imidazol-5-yl)carbonate

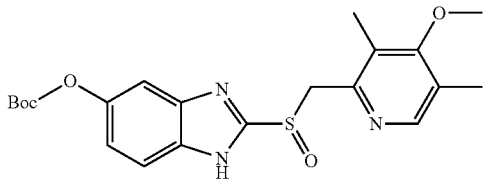 [SMILES: COc1c(C)cnc(CS(=O)c2nc3cc(OC(=O)OC(C)(C)C)ccc3[nH]2)c1C]

Except that acetyl chloride is replaced by tert-butyl carbonochloridate, the other reactants and preparation steps are similar to those described in Example 1 to afford the title compound.

$^1$H NMR (400 MHz, Acetone-$d_6$) δ 8.17 (s, 1H), 7.68 (d, J=8.8 Hz, 1H), 7.49 (s, 1H), 7.15 (d, J=8.9, 1H), 4.72 (s, 2H), 3.74 (s, 3H), 2.24 (s, 6H), 1.54 (s, 9H).

LRMS (ESI$^+$) m/z: 432.2 (M+H)$^+$.

Example 1-26 NCTU-SUN-12124: (2-(((4-methoxy-3,5-dimethylpyridin-2-yl)methyl)sulfinyl)-1H-benzo[d]imidazol-5-yl (Z)-but-2-enoate)

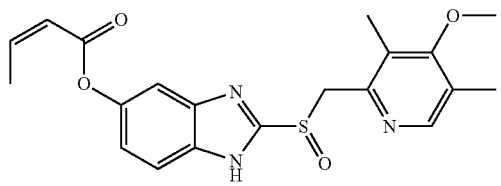 [SMILES: C/C=C\C(=O)Oc1ccc2[nH]c(S(=O)Cc3ncc(C)c(OC)c3C)nc2c1]

Except that acetyl chloride is replaced by (Z)-but-2-enoyl chloride, the other reactants and preparation steps are similar to those described in Example 1 to afford the title compound.

$^1$H NMR (400 MHz, Acetone-$d_6$) δ 8.18 (s, 1H), 7.69 (d, J=8.4 Hz, 1H), 7.47 (dd, J=2.2, 0.4 Hz, 1H), 7.19 (dq, J=15.5, 6.9 Hz, 1H), 7.11 (dd, J=8.8, 2.2 Hz, 1H), 6.13 (dq, J=15.5, 1.7 Hz, 1H), 4.76-4.67 (q, J=13.6, 2H), 3.74 (s, 3H), 2.25 (s, 3H), 2.24 (s, 3H), 1.99 (dd, J=6.9, 1.7 Hz, 3H).

LRMS (ESI$^+$) m/z: 400.2 (M+H)$^+$.

Example 1-27 NCTU-SUN-12125: (2-(((4-methoxy-3,5-dimethylpyridin-2-yl)methyl)sulfinyl)-1H-benzo[d]imidazol-5-yl 3-methylbut-2-enoate)

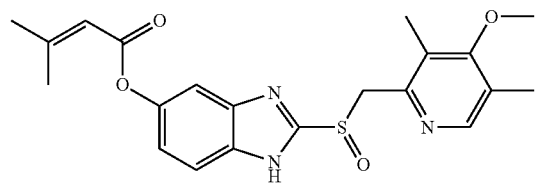 [SMILES: COc1c(C)cnc(CS(=O)c2nc3cc(OC(=O)C=C(C)C)ccc3[nH]2)c1C]

Except that acetyl chloride is replaced by 3-methylbut-2-enoyl chloride, the other reactants and preparation steps are similar to those described in Example 1 to afford the title compound.

¹H NMR (400 MHz, Acetone-d₆) δ 8.18 (s, 1H), 7.69 (d, J=8.7 Hz, 1H), 7.45 (d, J=2.0 Hz, 1H), 7.09 (dd, J=8.7, 2.1 Hz, 1H), 5.98 (dt, J=2.6, 1.3 Hz, 1H), 4.71 (dd, J=13.6 Hz, 2H), 3.74 (s, 3H), 2.24 (s, 3H), 2.24 (s, 3H), 2.22 (d, J=1.2 Hz, 3H), 2.02 (d, J=1.3 Hz, 3H).

LRMS (ESI⁺) m/z: 414.2 (M+H)⁺.

Example 1-28 NCTU-SUN-12122: (2-(((4-methoxy-3,5-dimethylpyridin-2-yl)methyl)sulfinyl)-1H-benzo[d]imidazol-5-yl furan-2-carboxylate)

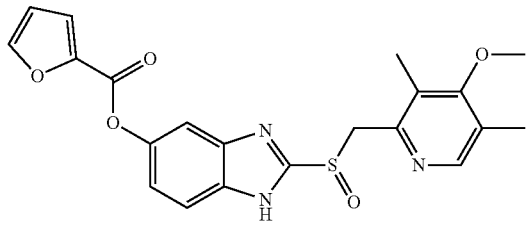 [SMILES: COc1c(C)cnc(CS(=O)c2nc3cc(OC(=O)c4ccco4)ccc3[nH]2)c1C]

Except that acetyl chloride is replaced by furan-2-carbonyl chloride, the other reactants and preparation steps are similar to those described in Example 1 to afford the title compound.

¹H NMR (400 MHz, Acetone-d₆) δ 8.18 (s, 1H), 7.96 (dd, J=1.8, 0.8 Hz, 1H), 7.74 (d, J=8.8 Hz, 1H), 7.60 (d, J=2.1 Hz, 1H), 7.51 (dd, J=3.5, 0.8 Hz, 1H), 7.24 (dd, J=8.8, 2.1 Hz, 1H), 6.77 (dd, J=3.5, 1.8 Hz, 1H), 4.74 (q, J=13.6 Hz, 2H), 3.75 (s, 3H), 2.25 (s, 3H), 2.24 (s, 3H).

LRMS (ESI⁺) m/z: 426.1 (M+H)⁺.

Example 1-29 NCTU-SUN-12123: (2-(((4-methoxy-3,5-dimethylpyridin-2-yl)methyl)sulfinyl)-1H-benzo[d]imidazol-5-ylacrylate)

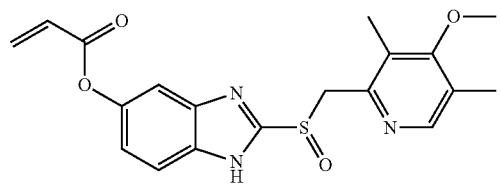

Except that acetyl chloride is replaced by acryloyl chloride, the other reactants and preparation steps are similar to those described in Example 1 to afford the title compound.

¹H NMR (400 MHz, Acetone-d₆) δ 8.17 (s, 1H), 7.71 (d, J=8.8 Hz, 1H), 7.51 (d, J=2.2 Hz, 1H), 7.14 (dd, J=8.8, 2.2 Hz, 1H), 6.59 (dd, J=17.3, 1.5 Hz, 1H), 6.42 (dd, J=17.3, 10.4 Hz, 1H), 6.11 (dd, J=10.4, 1.5 Hz, 1H), 4.73 (q, J=13.6, 2H), 3.74 (s, 3H), 2.24 (s, 3H), 2.24 (s, 3H).

LRMS (ESI⁺) m/z: 386.1 (M+H)⁺.

Example 1-30 NCTU-SUN-12127: (2-(((4-methoxy-3,5-dimethylpyridin-2-yl)methyl)sulfinyl)-1H-benzo[d]imidazol-5-yl 2-methylbutanoate)

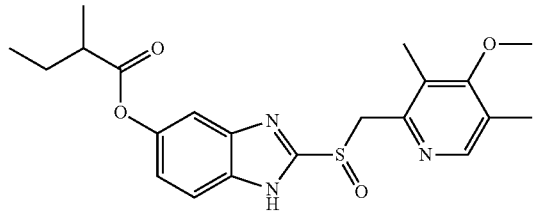 [SMILES: CCC(C)C(=O)Oc1ccc2[nH]c(S(=O)Cc3ncc(C)c(OC)c3C)nc2c1]

Except that acetyl chloride is replaced by 2-methylbutanoyl chloride, the other reactants and preparation steps are similar to those described in Example 1 to afford the title compound.

¹H NMR (400 MHz, Acetone-d₆) δ 8.17 (s, 1H), 7.68 (d, J=8.0 Hz, 1H), 7.42 (s, 1H), 7.07 (dd, J=8.7, 1.9 Hz, 1H), 4.80-4.68 (q, J=13.6 Hz, 2H), 3.72 (s, 3H), 2.75-2.63 (m, 1H), 2.23 (s, 6H), 1.89-1.77 (m, 1H), 1.71-1.60 (m, 1H), 1.29 (d, J=7.0 Hz, 4H), 1.04 (t, J=7.4 Hz, 3H).

LRMS (ESI⁺) m/z: 416.1 (M+H)⁺.

Example 1-31 NCTU-SUN-12128: (2-(((4-methoxy-3,5-dimethylpyridin-2-yl)methyl)sulfinyl)-1H-benzo[d]imidazol-5-yl 3-cyclopentylpropanoate)

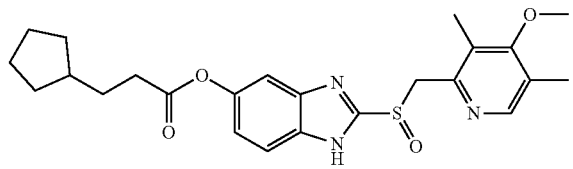 [SMILES: COc1c(C)cnc(CS(=O)c2nc3cc(OC(=O)CCC4CCCC4)ccc3[nH]2)c1C]

Except that acetyl chloride is replaced by cyclopentanecarbonyl chloride, the other reactants and preparation steps are similar to those described in Example 1 to afford the title compound.

¹H NMR (400 MHz, Acetone-d₆) δ 8.17 (s, 1H), 7.68 (d, J=8.7 Hz, 1H), 7.43 (d, J=2.1 Hz, 1H), 7.08 (dd, J=8.8, 2.2 Hz, 1H), 4.78-4.66 (q, J=13.6, 2H), 3.74 (s, 3H), 2.66-2.61 (m, 2H), 2.24 (s, 6H), 1.94-1.81 (m, 3H), 1.77 (dd, J=14.9, 7.4 Hz, 2H), 1.69-1.51 (m, 5H), 1.23-1.13 (m, 2H).

LRMS (ESI⁺) m/z: 456.1 (M+H)⁺.

Example 1-32 NCTU-SUN-12129: (2-(((4-methoxy-3,5-dimethylpyridin-2-yl)methyl)sulfinyl)-1H-benzo[d]imidazol-5-yl(E)-3-(2-chlorophenyl)acrylate)

Except that acetyl chloride is replaced by 2-chlorobenzoyl chloride, the other reactants and preparation steps are similar to those described in Example 1 to afford the title compound.

$^1$H NMR (400 MHz, Acetone-$d_6$) δ 8.26 (d, J=16.0 Hz, 1H), 8.18 (s, 1H), 8.02 (dd, J=7.6, 2.0 Hz, 1H), 7.72 (d, J=7.8 Hz, 1H), 7.58-7.54 (m, 2H), 7.48 (m, 2H), 7.20 (dd, J=8.7, 2.0 Hz, 1H), 6.88 (d, J=16.0 Hz, 1H), 4.81-4.70 (q, J=13.6, 2H), 3.73 (s, 3H), 2.24 (s, 3H), 2.23 (s, 3H).

LRMS (ESI$^+$) m/z: 496.0 (M+H)$^+$.

Example 1-33 NCTU-SUN-12130: (2-(((4-methoxy-3,5-dimethylpyridin-2-yl)methyl)sulfinyl)-1H-benzo[d]imidazol-5-yl 6-bromohexanoate)

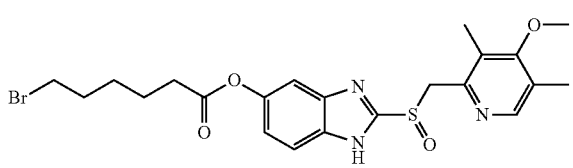 [SMILES: COc1c(C)cnc(CS(=O)c2nc3cc(OC(=O)CCCCCBr)ccc3[nH]2)c1C]

Except that acetyl chloride is replaced by 6-bromohexanoyl chloride, the other reactants and preparation steps are similar to those described in Example 1 to afford the title compound.

$^1$H NMR (400 MHz, Acetone-$d_6$) δ 8.17 (s, 1H), 7.68 (d, J=8.5 Hz, 1H), 7.44 (d, J=2.3 Hz, 1H), 7.09 (dd, J=8.8, 2.2 Hz, 0H), 4.77-4.68 (q, J=13.6, 2H), 3.74 (s, 3H), 3.55 (t, J=6.7 Hz, 2H), 2.66 (t, J=7.4 Hz, 2H), 2.35 (s, 6H) 1.99-1.91 (m, 2H), 1.84-1.76 (m, 2H), 1.66-1.56 (m, 2H).

LRMS (ESI$^+$) m/z: 508.1 (M+H)$^+$.

Example 1-34 NCTU-SUN-11021: (2-(((4-methoxy-3,5-dimethylpyridin-2-yl)methyl)sulfinyl)-1H-benzo[d]imidazol-5-yl 2-fluorobenzoate)

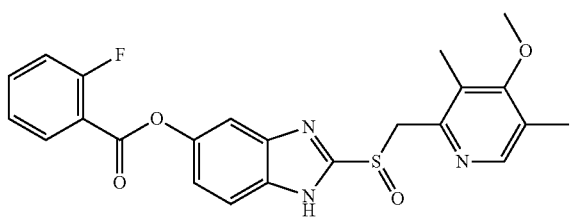 [SMILES: COc1c(C)cnc(CS(=O)c2nc3cc(OC(=O)c4ccccc4F)ccc3[nH]2)c1C]

Except that acetyl chloride is replaced by 2-fluorobenzoyl chloride, the other reactants and preparation steps are similar to those described in Example 1 to afford the title compound.

$^1$H NMR (400 MHz, Acetone-$d_6$) δ 8.24-8.13 (m, 2H), 7.78 (dddd, J=8.4, 7.4, 4.9, 1.8 Hz, 2H), 7.64 (d, J=2.3 Hz, 1H), 7.48-7.32 (m, 2H), 7.28 (dd, J=8.8, 2.2 Hz, 1H), 4.74 (s, 3H), 3.76 (s, 3H), 2.26 (s, 3H), 2.25 (s, 3H).

LRMS (ESI$^+$) m/z: 454.1 (M+H)$^+$.

Example 1-35 NCTU-SUN-11020: (2-(((4-methoxy-3,5-dimethylpyridin-2-yl)methyl)sulfinyl)-1H-benzon[d]imidazok-5-yl 4-methoxybenzoate)

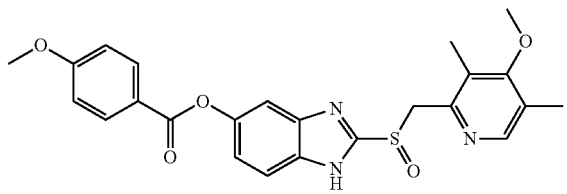

Except that acetyl chloride is replaced by 4-methoxybenzoyl chloride, the other reactants and preparation steps are similar to those described in Example 1 to afford the title compound.

$^1$H NMR (400 MHz, Acetone-$d_6$) δ 8.76-7.84 (m, 3H), 7.74 (dd, J=8.8, 0.6 Hz, 1H), 7.59 (dd, J=2.2, 0.5 Hz, 1H), 7.23 (dd, J=8.7, 2.2 Hz, 1H), 7.13 (d, J=8.9 Hz, 2H), 4.74 (s, 2H), 3.94 (s, 3H), 3.75 (s, 3H), 2.25 (s, 3H), 2.24 (s, 3H).

LRMS (ESI$^+$) m/z: 466.2 (M+H)$^+$.

Example 1-36 NCTU-SUN-11022: (2-(((4-methoxy-3,5-dimethylpyridin-2-yl)methyl)sulfinyl)-1H-benzo[d]imidazol-5-yl (3r,5r,7r)-adamantane-1-carboxylate)

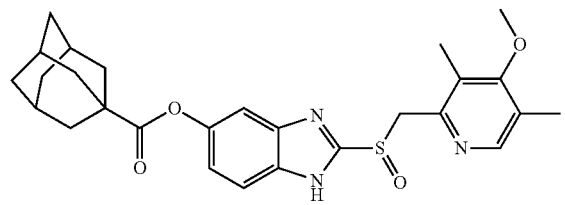 [SMILES: COc1c(C)cnc(CS(=O)c2nc3cc(OC(=O)C45CC6CC(CC(C6)C4)C5)ccc3[nH]2)c1C]

Except that acetyl chloride is replaced by adamantane-1-carbonyl chloride, the other reactants and preparation steps are similar to those described in Example 1 to afford the title compound.

$^1$H NMR (400 MHz, Acetone-$d_6$) δ 8.16 (s, 1H), 7.64 (d, J=8.6 Hz, 1H), 7.37 (d, J=2.2 Hz, 1H), 7.02 (dd, J=8.8, 2.2 Hz, 1H), 4.83-4.71 (m, 2H), 3.69 (s, 3H), 2.22 (s, 3H), 2.21 (s, 3H), 2.20-1.80 (m, 15H)

LRMS (ESI$^+$) m/z: 494.2 (M+H)$^+$.

Example 1-37 NCTU-SUN-11023: (2-(((4-methoxy-3,5-dimethylpyridin-2-yl)methyl)sulfinyl)-1H-benzo[d]imidazol-5-yl isoxazole-5-carboxylate)

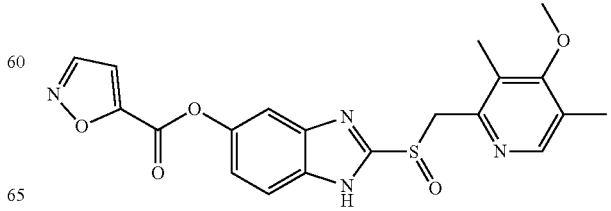

Except that acetyl chloride is replaced by isoxazole-5-carbonyl chloride, the other reactants and preparation steps are similar to those described in Example 1 to afford the title compound.

¹H NMR (400 MHz, Acetone-d₆) δ 8.76 (d, J=1.8 Hz, 1H), 8.17 (s, 1H), 7.74 (d, J=8.8 Hz, 1H), 7.67 (d, J=2.2 Hz, 1H), 7.39 (d, J=1.8 Hz, 1H), 7.30 (dd, J=8.8, 2.2 Hz, 1H), 4.86-4.72 (m, 2H), 3.70 (s, 3H), 2.22 (s, 3H), 2.21 (s, 3H).

LRMS (ESI⁺) m/z: 427.0 (M+H)⁺.

Example 1-38 NCTU-SUN-11030: (2-(((4-methoxy-3,5-dimethylpyridin-2-yl)methyl)sulfinyl)-1H-benzo[d]imidazol-5-yl 4-(tert-butyl)benzoate)

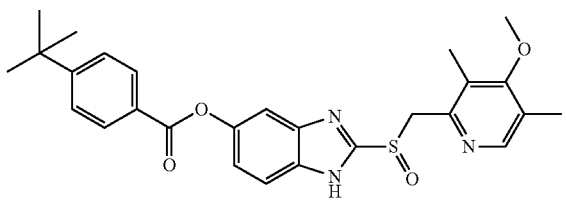 [SMILES: COc1c(C)cnc(CS(=O)c2nc3cc(OC(=O)c4ccc(C(C)(C)C)cc4)ccc3[nH]2)c1C]

Except that acetyl chloride is replaced by 4-(tert-butyl)benzoyl chloride, the other reactants and preparation steps are similar to those described in Example 1 to afford the title compound.

¹H NMR (400 MHz, Methanol-d₄) δ 8.14 (d, J=8.5 Hz, 2H), 8.11 (s, 1H), 7.69 (d, J=8.8 Hz, 1H), 7.62 (d, J=8.5 Hz, 2H) 7.51 (d, J=2.2 Hz, 1H), 7.21 (dd, J=8.8, 2.2 Hz, 1H), 4.78 (d, J=9.4 Hz, 2H), 3.69 (s, 3H), 2.24 (s, 3H), 2.18 (s, 3H), 1.39 (s, 9H).

LRMS (ESI⁺) m/z: 492.1 (M+H)⁺.

Example 1-39 NCTU-SUN-11031: (2-(((4-methoxy-3,5-dimethylpyridin-2-yl)methyl)sulfinyl)-1H-benzo[d]imidazol-5-yl 3-chloro-4-fluorobenzoate)

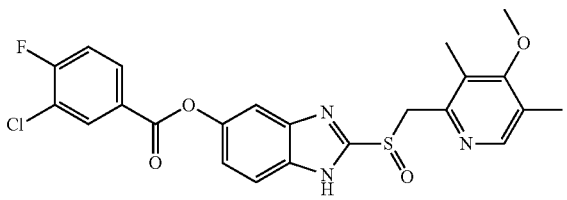 [SMILES: COc1c(C)cnc(CS(=O)c2nc3cc(OC(=O)c4ccc(F)c(Cl)c4)ccc3[nH]2)c1C]

Except that acetyl chloride is replaced by 4-chloro-3-fluorobenzoyl chloride, the other reactants and preparation steps are similar to those described in Example 1 to afford the title compound.

¹H NMR (400 MHz, Acetone-d₆) δ 8.34 (dd, J=7.2, 2.2 Hz, 1H), 8.24 (ddd, J=8.7, 4.7, 2.2 Hz, 1H), 8.18 (t, J=0.8 Hz, 1H), 7.76 (dd, J=8.8, 0.6 Hz, 1H), 7.65 (dd, J=2.3, 0.6 Hz, 1H), 7.58 (t, J=8.8 Hz, 1H), 7.28 (dd, J=8.8, 2.2 Hz, 1H), 4.74 (s, 2H), 3.76 (s, 2H), 2.26 (s, 3H), 2.24 (s, 3H).

LRMS (ESI⁺) m/z: 488.0 (M+H)⁺.

Example 1-40 NCTU-SUN-25015: (2-(((4-methoxy-3,5-dimethylpyridin-2-yl)methyl)sulfinyl)-1H-benzo[d]imidazol-5-yl pivalate)

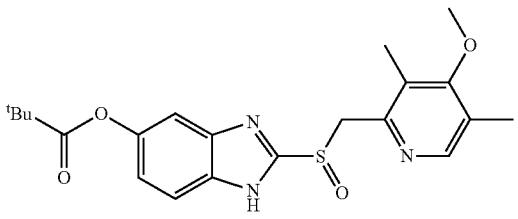 [SMILES: COc1c(C)cnc(CS(=O)c2nc3cc(OC(=O)C(C)(C)C)ccc3[nH]2)c1C]

Except that acetyl chloride is replaced by pivaloyl chloride, the other reactants and preparation steps are similar to those described in Example 1 to afford the title compound.

¹H NMR (400 MHz, Acetone-d₆) δ 8.17 (s, 1H), 7.69 (d, J=8.7 Hz, 1H), 7.42 (d, J=2.0 Hz, 1H), 7.07 (dd, J=8.7, 2.1 Hz, 1H), 5.62 (s, 1H), 4.71 (s, 2H), 3.75 (s, 3H), 2.24 (d, J=2.6 Hz, 6H), 1.37 (s, 9H).

LRMS (ESI⁺) m/z: 416.1 (M+H)⁺.

Example 1-41 NCTU-SUN-25016: (2-(((4-methoxy-3,5-dimethylpyridin-2-yl)methyl)sulfinyl)-1H-benzo[d]imidazol-5-yl pentanoate)

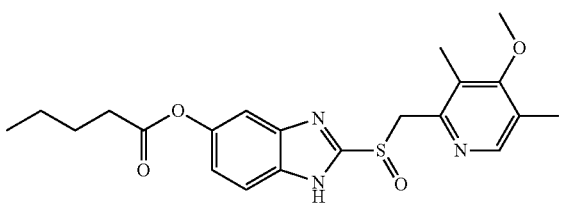 [SMILES: CCCCC(=O)Oc1ccc2[nH]c(S(=O)Cc3ncc(C)c(OC)c3C)nc2c1]

Except that acetyl chloride is replaced by pentanoyl chloride, the other reactants and preparation steps are similar to those described in Example 1 to afford the title compound.

¹H NMR (400 MHz, Acetone-d₆) δ 8.16 (s, 1H), 7.65 (d, J=8.7 Hz, 1H), 7.41 (d, J=2.1 Hz, 1H), 7.07 (dd, J=8.9, 2.1 Hz, 1H), 5.62 (s, 1H), 4.96-4.55 (m, 2H), 3.69 (s, 3H), 2.62 (t, J=7.5 Hz, 2H), 2.21 (d, J=3.3 Hz, 6H), 1.83-1.64 (m, 2H), 1.46 (q, J=7.4 Hz, 2H), 0.97 (t, J=7.4 Hz, 3H).

LRMS (ESI⁺) m/z: 416.1 (M+H)⁺.

Example 1-42 NCTU-SUN-25017: (2-(((4-methoxy-3,5-dimethylpyridin-2-yl)methyl)sulfinyl)-1H-benzo[d]imidazol-5-yl 4-nitrobenzoate)

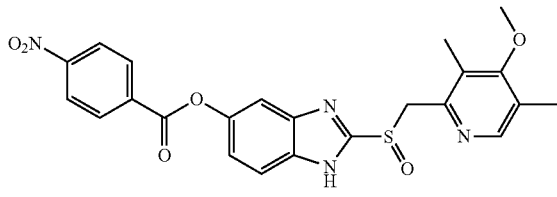 [SMILES: COc1c(C)cnc(CS(=O)c2nc3cc(OC(=O)c4ccc([N+](=O)[O-])cc4)ccc3[nH]2)c1C]

Except that acetyl chloride is replaced by 4-nitrobenzoyl chloride, the other reactants and preparation steps are similar to those described in Example 1 to afford the title compound.

¹H NMR (400 MHz, Acetone-d₆) δ 8.48 (d, J=2.3 Hz, 4H), 8.18 (s, 1H), 7.78 (d, J=8.8 Hz, 1H), 7.70 (d, J=2.2 Hz, 1H), 7.33 (dd, J=8.8, 2.3 Hz, 1H), 4.74 (s, 2H), 3.76 (s, 3H), 2.25 (d, J=7.2 Hz, 6H).

LRMS (ESI⁺) m/z: 481.2 (M+H)⁺.

Example 1-43 NCTU-SUN-25027: (2-(((4-methoxy-3,5-dimethylpyridin-2-yl)methyl)sulfinyl)-1H-benzo[d]imidazol-5-yl cyclobutanecarboxylate)

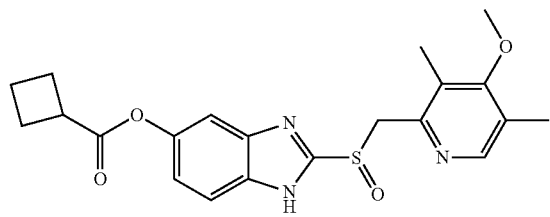 [SMILES: COc1c(C)cnc(CS(=O)c2nc3cc(OC(=O)C4CCC4)ccc3[nH]2)c1C]

Except that acetyl chloride is replaced by cyclobutanecarbonyl chloride, the other reactants and preparation steps are similar to those described in Example 1 to afford the title compound.

¹H NMR (400 MHz, Acetone-d₆) δ 8.17 (s, 1H), 7.69 (d, J=8.8 Hz, 1H), 7.44 (d, J=2.2 Hz, 1H), 7.09 (dd, J=8.8, 2.2 Hz, 1H), 4.71 (s, 2H), 3.75 (s, 3H), 3.48 (t, J=8.6 Hz, 1H), 2.39 (dt, J=29.5, 9.1 Hz, 4H), 2.24 (d, J=2.9 Hz, 5H), 2.05 (m, J=2.4 Hz, 2H).

LRMS (ESI⁺) m/z: 414.2 (M+H)⁺.

Example 1-44 NCTU-SUN-25028: (2-(((4-methoxy-3,5-dimethylpyridin-2-yl)methyl)sulfinyl)-1H-benzo[d]imidazol-5-yl thiophene-2-carboxylate)

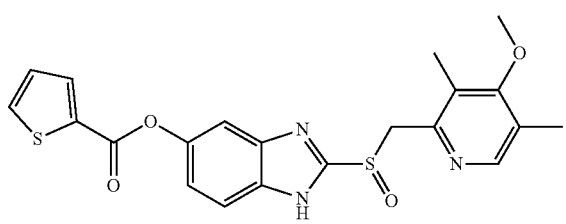 [SMILES: COc1c(C)cnc(CS(=O)c2nc3cc(OC(=O)c4cccs4)ccc3[nH]2)c1C]

Except that acetyl chloride is replaced by thiophene-2-carbonyl chloride, the other reactants and preparation steps are similar to those described in Example 1 to afford the title compound.

¹H NMR (400 MHz, Acetone-d₆) δ 8.18 (s, 1H), 8.04 (dd, J=3.8, 1.4 Hz, 1H), 7.99 (dd, J=5.0, 1.4 Hz, 1H), 7.74 (d, J=8.8 Hz, 1H), 7.62 (d, J=2.1 Hz, 1H), 7.32 (dd, J=5.1, 3.7 Hz, 1H), 7.25 (dd, J=8.8, 2.2 Hz, 1H), 4.75 (d, J=2.1 Hz, 2H), 3.74 (d, J=1.7 Hz, 3H), 2.24 (d, J=5.4 Hz, 6H).

LRMS (ESI⁺) m/z: 442.2 (M+H)⁺.

Example 1-45 NCTU-SUN-25029: (2-(((4-methoxy-3,5-dimethylpyridin-2-yl)methyl)sulfinyl)-1H-benzo[d]imidazol-5-yl 2-methylbutanoate)

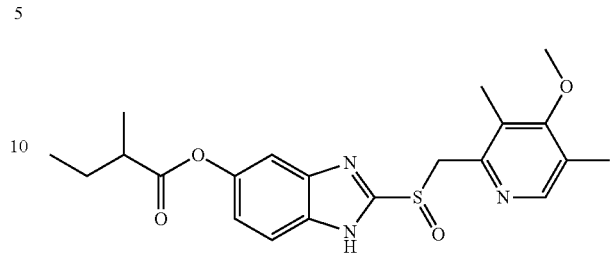

Except that acetyl chloride is replaced by 2-methylbutanoyl chloride, the other reactants and preparation steps are similar to those described in Example 1 to afford the title compound.

¹H NMR (400 MHz, Acetone-d₆) δ 8.17 (s, 1H), 7.68 (d, J=8.7 Hz, 1H), 7.49-7.32 (m, 1H), 7.07 (ddd, J=8.7, 2.3, 1.0 Hz, 1H), 4.76-4.52 (m, 2H), 3.74 (d, J=1.0 Hz, 3H), 2.69 (q, J=7.1 Hz, 1H), 2.24 (s, 6H), 1.92-1.75 (m, 1H), 1.65 (dddd, J=13.7, 7.4, 6.3, 1.1 Hz, 1H), 1.29 (dd, J=7.0, 1.0 Hz, 3H), 1.04 (td, J=7.4, 1.0 Hz, 3H).

LRMS (ESI⁺) m/z: 416.1 (M+H)⁺.

Example 1-46 NCTU-SUN-25030: (2-(((4-methoxy-3,5-dimethylpyridin-2-yl)methyl)sulfinyl)-1H-benzo[d]imidazol-5-yl 3,3-dimethylbutanoate)

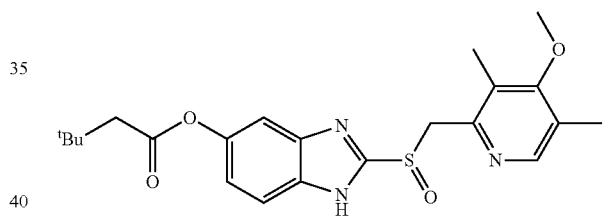

Except that acetyl chloride is replaced by 3,3-dimethylbutanoyl chloride, the other reactants and preparation steps are similar to those described in Example 1 to afford the title compound.

¹H NMR (400 MHz, Acetone-d₆) δ 8.17 (s, 1H), 7.69 (dd, J=8.7, 0.6 Hz, 1H), 7.43 (dd, J=2.2, 0.6 Hz, 1H), 7.08 (dd, J=8.7, 2.2 Hz, 1H), 4.72 (d, J=1.6 Hz, 2H), 3.74 (s, 3H), 2.50 (s, 2H), 2.24 (d, J=1.3 Hz, 6H), 1.15 (s, 9H).

LRMS (ESI⁺) m/z: 430.1 (M+H)⁺.

Example 1-47 NCTU-SUN-25031: (2-(((4-methoxy-3,5-dimethylpyridin-2-yl)methyl)sulfinyl)-1H-benzo[d]imidazol-5-yl 2-methoxyacetate)

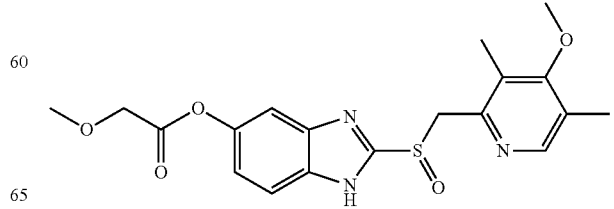

Except that acetyl chloride is replaced by 2-methoxyacetyl chloride, the other reactants and preparation steps are similar to those described in Example 1 to afford the title compound.

$^1$H NMR (400 MHz, Acetone-$d_6$) δ 8.17 (s, 1H), 7.70 (d, J=8.7 Hz, 1H), 7.50 (s, 1H), 7.14 (d, J=8.8 Hz, 1H), 4.72 (s, 2H), 4.36 (s, 2H), 3.75 (s, 3H), 3.49 (d, J=1.2 Hz, 2H), 2.24 (d, J=2.5 Hz, 6H).

LRMS (ESI$^+$) m/z: 404.0 (M+H)$^+$.

Example 1-48 NCTU-SUN-25032 (ethyl (2-(((4-methoxy-3,5-dimethylpyridin-2-yl)methyl)sulfinyl)-1H-benzo[d]imidazol-5-yl) carbonate)

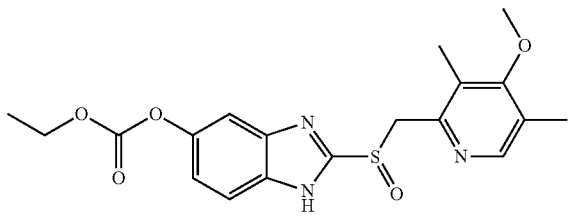 [SMILES: CCC(C)C(=O)Oc1ccc2[nH]c(S(=O)Cc3ncc(C)c(OC)c3C)nc2c1]

Except that acetyl chloride is replaced by ethyl carbonochloridate the other reactants and preparation steps are similar to those described in Example 1 to afford the title compound.

$^1$H NMR (400 MHz, Acetone-$d_6$) δ 8.17 (s, 1H), 7.69 (d, J=8.8 Hz, 1H), 7.53 (d, J=2.2 Hz, 1H), 7.18 (dd, J=8.8, 2.2 Hz, 1H), 4.74 (d, J=2.6 Hz, 2H), 4.30 (q, J=7.1 Hz, 2H), 3.73 (s, 3H), 2.23 (s, 7H), 1.35 (t, J=7.1 Hz, 4H).

LRMS (ESI$^+$) m/z: 404.0 (M+H)$^+$.

Example 2-126065: Methyl 1-(furan-2-ylmethyl)-2-(((4-methoxy-3,5-dimethylpyridin-2-yl)methyl)amino)-1H-benzo[d]imidazole-5-carboxylate

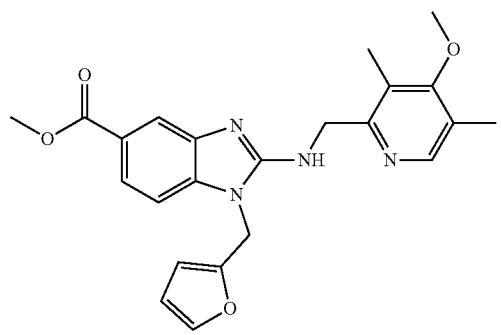

To a solution of 4-fluoro-3-nitrobenzoic acid 1 (5.0 g, 27.0 mmol) in dry MeOH (30 mL), $H_2SO_4$ (5 mL, 0.3 M) was added and the reaction mixture was heated to reflux for 12 h. The solvent was removed under reduced pressure, crude reaction mixture was dissolved in EtOAc (150 mL), washed with saturated $NaHCO_3$(20 mL×2), water (10 mL×2) and brine (10 mL). The EtOAc layer was dried over anhydrous $MgSO_4$ and evaporated to get methyl 4-fluoro-3-nitrobenzoate 2 (95%) as a white solid.

Compound 2 (2.0 g, 10.2 mmol) and 2-Aminomethylfuran (3 equiv.) in dry $CH_2Cl_2$ (50 mL) were stirred at room temperature for 2 h. Upon completion of reaction the solvent was removed and the crude product was purified by flash column chromatography to afford nitro benzoates 3 (90%).

To a solution of compound 3 (2.0 g, 4.8 mmol) in dry MeOH (100 mL), zinc dust (15 equiv., 71.4 mmol) and ammonium formate (7.5 equiv., 35.7 mmol) were added and the resulting reaction mixture was stirred at room temperature for 30 min. Upon completion of reaction, Zn dust was filtered through a bed of celite, filtrate was evaporated and the product was dissolved in $CH_2Cl_2$ (100 mL). The precipitated ammonium formate was filtered off and the solvent was evaporated to furnish compound 4 (92%).

Use DCM to dissolve compound 4 (1.0 g, 4.0 mmol) then add 1.2 equiv. CNBr to react at room temperature. After 8 hours the mixture can be extracted with DCM and water. The solvent was removed and the crude product was purified by flash column chromatography to afford 5 (60%)

To a solution of methyl 2-amino-1-(furan-2-ylmethyl)-1H-benzo[d]imidazole-5-carboxylate 5 (0.05 g, 0.18 mmol) in acetoniritle (10 mL) was added $K_2CO_3$ (0.0497 g, 0.36 mmol) and KI (0.0089 g, 0.054 mmol) followed by 2-(chloromethyl)-4-methoxy-3,5-dimethylpyridine 6 (0.041 g, 0.22 mmol) and the reaction mixture was allowed to reflux for six hours. After 6 h, the solvent was evaporated and the reaction mixture was diluted with saturated aq. $NaHCO_3$(10 mL) and extracted with EtOAc (3*10 mL).

The combined organic phase was washed with saturated brine (30 mL). The crude product was purified by silica-gel column chromatography using 8% methanol/EtOAc to obtain the pure product NCTU-SUN-26065 as a white solid 0.053 g (71%).

$^1$H NMR (400 MHz, Chloroform-d) δ 8.34 (s, 1H), 7.83 (dd, J=8.3, 1.4 Hz, 1H), 7.73 (d, J=1.2 Hz, 1H), 7.34 (dd, J=1.8, 0.7 Hz, 1H), 7.13 (d, J=8.3 Hz, 1H), 6.37 (d, J=3.3 Hz, 1H), 6.32 (dd, J=3.2, 1.9 Hz, 1H), 5.42 (s, 2H), 5.10 (s, 2H), 3.89 (s, 3H), 3.87 (s, 3H), 2.33 (s, 3H), 2.30 (s, 3H); $^{13}$C NMR (101 MHz, Chloroform-d) δ 166.75, 153.88, 142.73, 133.38, 128.36, 124.86, 124.00, 110.60, 109.61, 109.04, 108.26, 77.22, 61.46, 52.24, 38.50, 31.90, 29.67, 29.33, 22.66, 14.64, 14.09, 11.39; LRMS (ESI+): m/z 422.3 (M+H)$^+$.

Example 2-2 21098: Methyl 2-(((4-methoxy-3,5-dimethylpyridin-2-yl)methyl)amino)-1-propyl-1H-benzo[d]imidazole-5-carboxylate

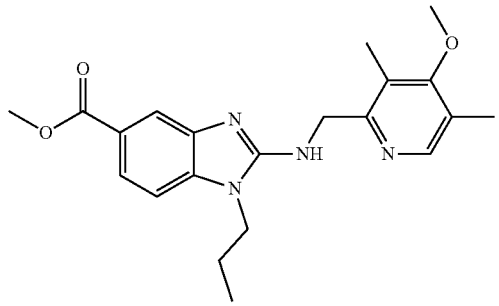

Except that amine is replaced by propan-1-amine, the other reactants and preparation steps are similar to those described in Example 2-1 to afford the title compound.

$^1$H NMR (400 MHz, Methanol-$d_4$) δ 7.96 (s, 1H), 7.91 (d, J=8.4 Hz, 1H), 7.68 (s, 1H), 7.42 (d, J=8.4 Hz, 1H), 5.41 (s, 2H), 4.09 (t, J=7.4 Hz, 2H), 3.81 (d, J=13.8 Hz, 6H), 2.34 (s, 3H), 2.20 (s, 3H), 1.85 (d, J=7.9 Hz, 2H), 1.02 (t, J=7.4

Hz, 3H); $^{13}$C NMR (101 MHz, Methanol-$d_4$) δ 164.54, 148.32, 134.44, 126.25, 124.69, 124.43, 109.95, 108.43, 59.29, 51.27, 45.10, 43.91, 29.31, 20.86, 11.90, 9.78, 9.16; LRMS (ESI+): m/z 383.3 (M+H)$^+$.

Example 2-3 21103: Methyl 2-(((4-methoxy-3,5-dimethylpyridin-2-yl)methyl)amino)-1-(3-methoxypropyl)-1H-benzo[d]imidazole-5-carboxylate

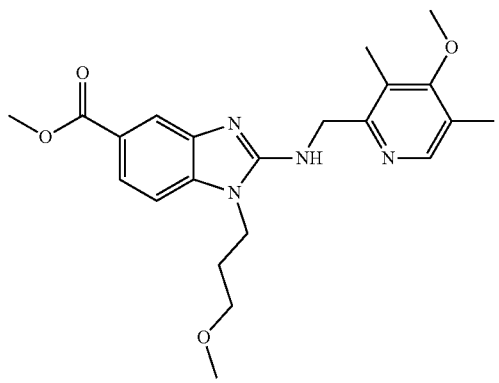

Except that amine is replaced by 3-methoxypropan-1-amine, the other reactants and preparation steps are similar to those described in Example 2-1 to afford the title compound.

$^1$H NMR (400 MHz, Methanol-$d_4$) δ 8.10 (s, 1H), 7.90 (t, J=1.8 Hz, 1H), 7.67 (dt, J=8.4, 1.9 Hz, 1H), 7.11 (dd, J=8.4, 2.1 Hz, 1H), 4.58 (d, J=2.1 Hz, 2H), 4.09-4.01 (m, 2H), 3.82 (d, J=2.1 Hz, 3H), 3.73 (d, J=2.1 Hz, 3H), 3.19 (d, J=2.1 Hz, 3H), 2.19 (dd, J=10.1, 2.1 Hz, 6H), 1.96 (p, J=6.2 Hz, 2H); $^{13}$C NMR (101 MHz, Methanol-$d_4$) δ 167.93, 164.20, 155.50, 153.88, 147.84, 141.23, 138.15, 125.49, 124.19, 122.68, 121.59, 116.14, 106.85, 68.04, 59.16, 57.48, 50.95, 45.26, 38.49, 28.17, 11.97, 9.08; LRMS (ESI+): m/z 413.3 (M+H)$^+$.

Example 2-4 26070: 1-(furan-2-ylmethyl)-2-(((4-methoxy-3,5-dimethylpyridin-2-yl)methyl)amino)-1H-benzo[d]imidazole-5-carboxylic acid

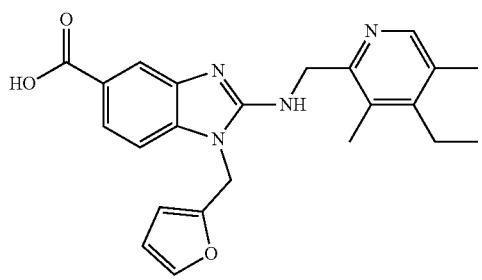 [SMILES: CCc1c(C)cnc(CNc2nc3cc(C(=O)O)ccc3n2Cc2ccco2)c1C]

To a solution of 4-fluoro-3-nitrobenzoic acid 1 (5.0 g, 27.0 mmol) in dry MeOH (30 mL), $H_2SO_4$ (5 mL, 0.3 M) was added and the reaction mixture was heated to reflux for 12 h. The solvent was removed under reduced pressure, crude reaction mixture was dissolved in EtOAc (150 mL), washed with saturated $NaHCO_3$(20 mL×2), water (10 mL×2) and brine (10 mL). The EtOAc layer was dried over anhydrous MgSO$_4$ and evaporated to get methyl 4-fluoro-3-nitrobenzoate 2 (95%) as a white solid.

Compound 2 (2.0 g, 10.2 mmol) and furan-2-ylmethanamine (3 equiv.) in dry $CH_2Cl_2$ (50 mL) were stirred at room temperature for 2 h. Upon completion of reaction the solvent was removed and the crude product was purified by flash column chromatography to afford nitro benzoates 3 (90%).

To a solution of compound 3 (2.0 g, 4.8 mmol) in dry MeOH (100 mL), zinc dust (15 equiv., 71.4 mmol) and ammonium formate (7.5 equiv., 35.7 mmol) were added and the resulting reaction mixture was stirred at room temperature for 30 min. Upon completion of reaction, Zn dust was filtered through a bed of celite, filtrate was evaporated and the product was dissolved in $CH_2Cl_2$ (100 mL). The precipitated ammonium formate was filtered off and the solvent was evaporated to furnish compound 4 (92%).

Use DCM to dissolve compound 4 (1.0 g, 4.0 mmol) then add 1.2 equiv. CNBr to react at room temperature. After 8 hours the mixture can be extracted with DCM and water. The solvent was removed and the crude product was purified by flash column chromatography to afford 5 (60%)

To a solution of methyl 2-amino-1-(furan-2-ylmethyl)-1H-benzo[d]imidazole-5-carboxylate 5 (0.05 g, 0.18 mmol) in acetoniritle (10 mL) was added $K_2CO_3$ (0.0497 g, 0.36 mmol) and KI (0.0089 g, 0.054 mmol) followed by 2-(chloromethyl)-4-methoxy-3,5-dimethylpyridine 6 (0.041 g, 0.22 mmol) and the reaction mixture was allowed to reflux for six hours. After 6 h, the solvent was evaporated and the reaction mixture was diluted with saturated aq. $NaHCO_3$(10 mL) and extracted with EtOAc (3*10 mL). The combined organic phase was washed with saturated brine (30 mL). The crude product was purified by silica-gel column chromatography using 8% methanol/EtOAc to obtain Methyl 1-(furan-2-ylmethyl)-2-(((4-methoxy-3,5-dimethylpyridin-2-yl)methyl)amino)-1H-benzo[d]imidazole-5-carboxylate 7.

And add NaOH (0.0251 g, 0.63 mmol) to a solution of Methyl 1-(furan-2-ylmethyl)-2-(((4-methoxy-3,5-dimethylpyridin-2-yl)methyl)amino)-1H-benzo[d]imidazole-5-carboxylate 7 (0.053 g, 0.126 mmol) in the EtOH/$H_2O$ (1/1, 3 mL) in the reflux condition. After 1 h, the solvent was evaporated and the reaction mixture was diluted with saturated aq. HCl (10 mL) and extracted with EtOAc (3*10 mL). The combined organic phase was washed with saturated brine (10 mL). The crude product was purified by silica-gel column chromatography using 20% methanol/EtOAc to obtain the pure product as a white solid 0.030 g (65%).

LRMS (ESI+): m/z 407.2 (M+H)$^+$.

Example 2-5 26066: Methyl 2-(((4-methoxy-3,5-dimethylpyridin-2-yl)methyl)amino)-1-pentyl-1H-benzo[d]imidazole-5-carboxylate

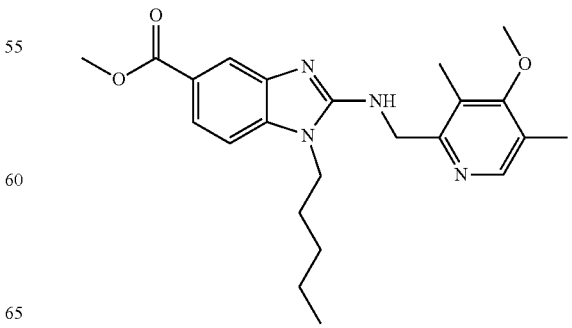

Except that amine is replaced by pentan-1-amine, the other reactants and preparation steps are similar to those described in Example 2-1 to afford the title compound.

¹H NMR (400 MHz, Chloroform-d) δ 8.08 (s, 1H), 8.01 (dd, J=8.4, 1.2 Hz, 1H), 7.72 (s, 1H), 7.29 (d, J=8.5 Hz, 1H), 5.92 (s, 2H), 4.49 (t, J=7.2 Hz, 2H), 3.89 (s, 6H), 2.47 (s, 3H), 2.26 (s, 3H), 1.96-1.83 (m, 2H), 1.54-1.41 (m, 2H), 1.44-1.29 (m, 2H), 0.88 (t, J=7.2 Hz, 3H); LRMS (ESI+): m/z 411.2 (M+H)⁺.

Example 2-6 21102: 2-(((4-methoxy-3,5-dimethylpyridin-2-yl)methyl)amino)-1-propyl-1H-benzo[d]imidazole-5-carboxylic acid

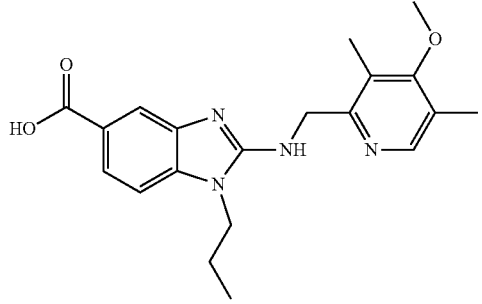 [SMILES: CCCn1c(NCc2ncc(C)c(OC)c2C)nc2cc(C(=O)O)ccc21]

Except that amine is replaced by propan-1-amine, the other reactants and preparation steps are similar to those described in Example 2-4 to afford the title compound.

¹H NMR (400 MHz, Methanol-d₄) δ 8.04 (d, J=8.3 Hz, 1H), 7.95 (s, 1H), 7.89 (s, 1H), 7.64 (d, J=8.1 Hz, 1H), 5.57 (s, 2H), 4.25 (t, J=7.3 Hz, 2H), 3.83 (s, 3H), 2.41 (s, 3H), 2.21 (s, 3H), 1.92 (d, J=7.3 Hz, 2H), 1.07 (t, J=7.3 Hz, 3H); ¹³C NMR (101 MHz, Methanol-d₄) δ 150.03, 148.40, 130.63, 126.40, 125.74, 111.55, 109.87, 59.38, 45.34, 44.56, 20.95, 11.93, 9.68, 9.17; LRMS (ESI+): m/z 369.2 (M+H)⁺.

Example 2-7 26071: Methyl 2-(((4-methoxy-3,5-dimethylpyridin-2-yl)methyl)amino)-1-(4-methoxybenzyl)-1H-benzo[d]imidazole-5-carboxylate

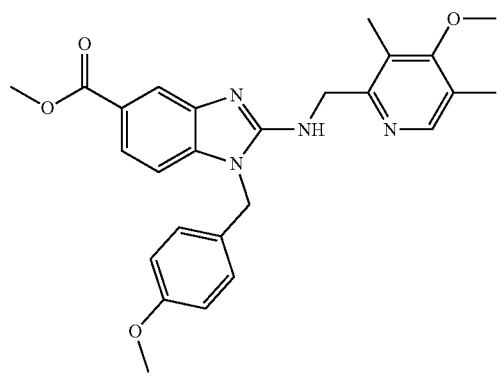

Except a amine is replaced by (4-methoxyphenyl)methanamine, the other reactants and preparation steps are similar to those described in Example 2-1 to afford the title compound.

¹H NMR (400 MHz, Methanol-d₄) δ 8.02 (s, 1H), 7.83 (dd, J=8.4, 1.5 Hz, 1H), 7.68 (d, J=1.6 Hz, 1H), 7.29 (d, J=8.7 Hz, 2H), 7.23 (d, J=8.4 Hz, 1H), 6.92 (d, J=8.7 Hz, 2H), 5.43 (s, 2H), 5.29 (s, 2H), 3.83 (s, 3H), 3.81 (s, 3H), 3.77 (s, 3H), 2.36 (s, 3H), 2.24 (s, 3H); LRMS (ESI+): m/z 461.2 (M+H)⁺.

Example 2-8 21105: 2-(bis((4-methoxy-3,5-dimethylpyridin-2-yl)methyl)amino)-1-(2-(cyclohex-1-en-1-yl)ethyl)-1H-benzo[d]imidazole-5-carboxylic acid

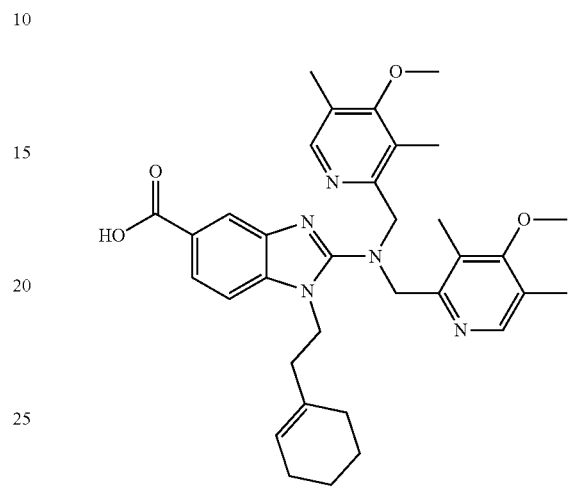

Except that amine is replaced by 2-(cyclohex-1-en-1-yl)ethanamine, the other reactants and preparation steps are similar to those described in Example 2-4 to afford the title compound.

¹H NMR (400 MHz, Methanol-d₄) δ 8.17 (s, 2H), 8.07 (s, 1H), 7.82 (d, J=8.2 Hz, 1H), 7.26 (d, J=8.3 Hz, 1H), 5.13 (s, 1H), 4.77 (s, 4H), 4.11 (t, J=7.8 Hz, 2H), 3.80-3.69 (m, 6H), 2.29 (t, J=8.4 Hz, 2H), 2.18 (d, J=21.8 Hz, 12H), 1.76 (s, 4H), 1.49-1.36 (m, 4H); ¹³C NMR (101 MHz, Methanol-d₄) δ 156.95, 145.93, 139.17, 131.88, 130.28, 125.53, 118.06, 117.75, 117.05, 115.18, 114.79, 110.01, 100.70, 51.25, 46.58, 35.22, 28.52, 19.80, 16.65, 14.33, 13.64, 3.99, 1.48; LRMS (ESI+): m/z 584.3 (M+H)+.

Example 2-9 21104: 2-(bis((4-methoxy-3,5-dimethylpyridin-2-yl)methyl)amino)-1-(3-methoxypropyl)-1H-benzo[d]imidazole-5-carboxylic acid

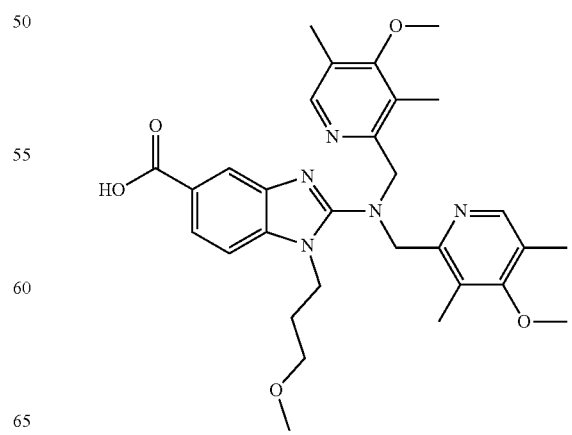

Except that amine is replaced by 3-methoxypropan-1-amine, the other reactants and preparation steps are similar to those described in Example 2-4 to afford the title compound.

$^1$H NMR (400 MHz, DMSO-d$_6$) δ 8.06 (s, 2H), 7.88 (d, J=1.6 Hz, 1H), 7.68 (dd, J=8.4, 1.6 Hz, 1H), 7.32 (d, J=8.4 Hz, 1H), 4.65 (s, 4H), 4.17 (t, J=7.6 Hz, 2H), 3.62 (s, 6H), 3.20 (t, J=5.9 Hz, 2H), 3.09 (s, 3H), 2.10 (s, 6H), 2.05 (s, 6H), 1.94-1.88 (m, 2H); $^{13}$C NMR (101 MHz, DMSO-d$_6$) δ 168.52, 163.68, 158.90, 155.26, 148.49, 141.33, 125.19, 125.04, 124.05, 122.18, 118.11, 109.15, 69.30, 60.07, 58.30, 54.87, 41.74, 29.10, 13.24, 10.68; LRMS (ESI+): m/z 548.3 (M+H)$^+$.

Example 2-10 26076: 2-(((4-methoxy-3,5-dimethylpyridin-2-yl)methyl)amino)-1-pentyl-1H-benzo[d]imidazole-5-carboxylic acid

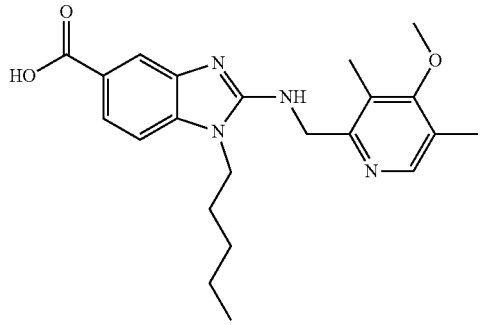 [SMILES: CCCCCn1c(NCc2ncc(C)c(OC)c2C)nc2cc(C(=O)O)ccc21]

Except that amine is replaced by pentan-1-amine, the other reactants and preparation steps are similar to those described in Example 2-4 to afford the title compound.

$^1$H NMR (400 MHz, DMSO-d$_6$) δ 7.88 (s, 1H), 7.81 (dd, J=8.2, 1.3 Hz, 1H), 7.70 (d, J=1.6 Hz, 1H), 7.39 (d, J=8.4 Hz, 2H), 5.59 (s, 2H), 4.23 (t, J=6.9 Hz, 2H), 3.72 (s, 3H), 2.30 (s, 3H), 2.11 (s, 3H), 1.83 (s, 2H), 1.30 (dq, J=6.7, 3.3 Hz, 4H), 0.90-0.73 (m, 3H); LRMS (ESI+): m/z 397.2 (M+H)$^+$.

Example 2-11 26077: 2-(((4-methoxy-3,5-dimethylpyridin-2-yl)methyl)amino)-1-(4-methoxybenzyl)-1H-benzo[d]imidazole-5-carboxylic acid

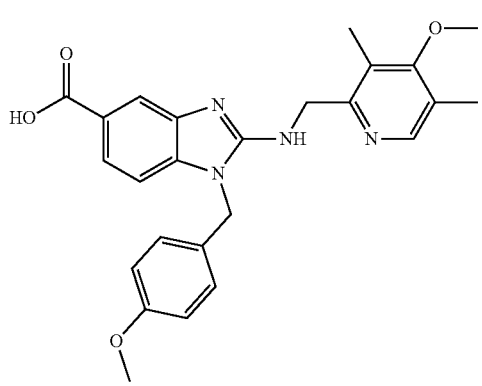 [SMILES: COc1ccc(Cn2c(NCc3ncc(C)c(OC)c3C)nc3cc(C(=O)O)ccc32)cc1]

Except that amine is replaced by (4-methoxyphenyl)methanamine, the other reactants and preparation steps are similar to those described in Example 2-4 to afford the title compound.

LRMS (ESI+): m/z 447.2 (M+H)$^+$.

Example 2-12 21115: 2-(((4-methoxy-3,5-dimethylpyridin-2-yl)methyl)amino)-1-(3-methoxypropyl)-1H-benzo[d]imidazole-5-carboxylic acid

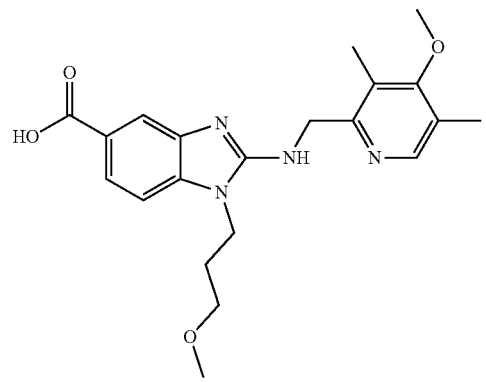 [SMILES: COCCCn1c(NCc2ncc(C)c(OC)c2C)nc2cc(C(=O)O)ccc21]

Except that amine is replaced by 3-methoxypropan-1-amine, the other reactants and preparation steps are similar to those described in Example 2-4 to afford the title compound.

$^1$H NMR (400 MHz, Methanol-d$_4$) δ 8.20 (s, 1H), 7.98-7.92 (m, 2H), 7.50 (d, J=8.7 Hz, 1H), 4.86 (s, 2H), 4.34 (t, J=6.7 Hz, 2H), 3.87 (s, 3H), 3.44 (t, J=5.6 Hz, 2H), 3.27 (s, 3H), 2.35 (s, 3H), 2.28 (s, 3H), 2.17-2.10 (m, 2H); $^{13}$C NMR (101 MHz, Methanol-d$_4$) δ 169.05, 152.95, 147.73, 136.45, 132.73, 127.94, 127.04, 126.46, 125.88, 114.80, 110.19, 69.41, 60.81, 58.69, 46.10, 41.07, 28.74, 13.36, 10.48; LRMS (ESI+): m/z 399.2 (M+H)$^+$.

Example 2-13 21116: Methyl 1-(2-(cyclohex-1-en-1-yl)ethyl)-2-(((4-methoxy-3,5-dimethylpyridin-2-yl)methyl)amino)-1H-benzo[d]imidazole-5-carboxylate

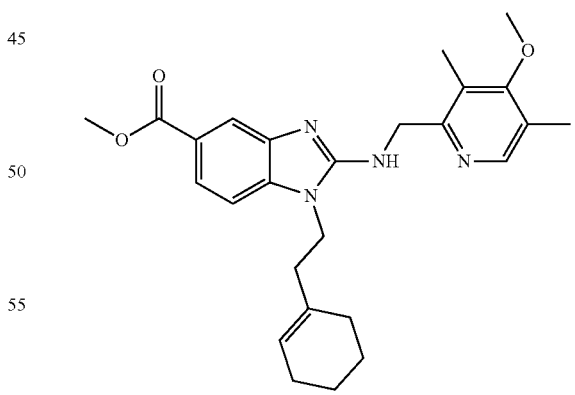

Except that amine is replaced by 2-(cyclohex-1-en-1-yl)ethanamine, the other reactants and preparation steps are similar to those described in Example 2-1 to afford the title compound.

$^1$H NMR (400 MHz, Acetone-d$_6$) δ 8.20 (s, 1H), 7.94 (d, J=1.4 Hz, 1H), 7.70 (dt, J=8.2, 1.4 Hz, 1H), 7.22 (dd, J=8.3, 1.2 Hz, 1H), 6.71 (s, 1H), 5.33 (dt, J=4.8, 2.3 Hz, 1H), 4.68

(d, J=3.7 Hz, 2H), 4.17 (td, J=7.2, 1.2 Hz, 2H), 3.84 (d, J=1.2 Hz, 3H), 3.79 (d, J=1.2 Hz, 3H), 2.41 (t, J=7.2 Hz, 2H), 2.28 (s, 3H), 2.23 (s, 3H), 2.04 (h, J=1.8 Hz, 2H), 2.02-1.97 (m, 2H), 1.82-1.76 (m, 2H), 1.51 (t, J=5.9 Hz, 2H), 1.42-1.37 (m, 2H); $^{13}$C NMR (101 MHz, Acetone-$d_6$) δ 167.29, 163.89, 155.45, 154.37, 148.06, 142.70, 138.71, 133.89, 125.06, 124.16, 123.65, 122.50, 120.86, 116.95, 107.03, 59.48, 50.95, 45.16, 41.27, 36.41, 29.18, 8.99, 28.79, 28.11, 24.91, 22.61, 21.81, 12.36, 9.35.

Example 2-14 21117: 1-(2-(cyclohex-1-en-1-yl)ethyl)-2-(((4-methoxy-3,5-dimethylpyridin-2-yl)methyl)amino)-1H-benzo[d]imidazole-5-carboxylic acid

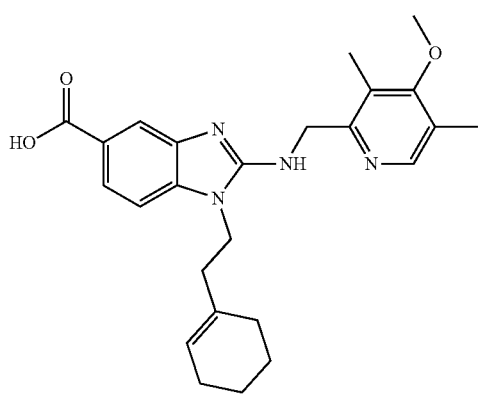 [SMILES: COc1c(C)cnc(CNc2nc3cc(C(=O)O)ccc3n2CCC2=CCCCC2)c1C]

Except that amine is replaced by 2-(cyclohex-1-en-1-yl)ethanamine, the other reactants and preparation steps are similar to those described in Example 2-4 to afford the title compound.

$^1$H NMR (400 MHz, DMSO-$d_6$) δ 8.15 (s, 1H), 7.70 (s, 1H), 7.56 (d, J=8.2 Hz, 1H), 7.15 (d, J=8.3 Hz, 1H), 7.08 (t, J=5.3 Hz, 1H), 5.23 (s, 1H), 4.61 (d, J=4.2 Hz, 2H), 4.12 (t, J=7.1 Hz, 2H), 3.69 (s, 3H), 2.28-2.13 (m, 8H), 1.90 (s, 2H), 1.72 (s, 2H), 1.38 (dq, J=31.9, 5.4 Hz, 4H); $^{13}$C NMR (101 MHz, DMSO-$d_6$) δ 168.24, 155.18, 155.12, 147.74, 141.57, 137.88, 133.55, 124.39, 123.56, 123.09, 123.01, 120.32, 115.84, 106.77, 59.43, 45.42, 40.30, 35.64, 27.52, 24.33, 21.97, 21.29, 12.55, 9.85.

Example 2-15 21118: Methyl 2-(((4-methoxy-3,5-dimethylpyridin-2-yl)methyl)amino)-1-phenethyl-1H-benzo[d]imidazole-5-carboxylate

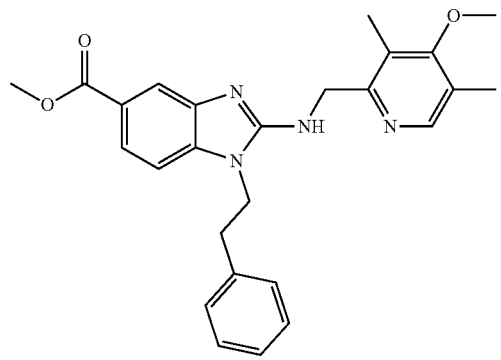

Except that amine is replaced by 2-phenylethanamine, the other reactants and preparation steps are similar to those described in Example 2-1 to afford the title compound.

$^1$H NMR (400 MHz, Methanol-$d_4$) δ 8.16 (s, 1H), 7.89 (s, 1H), 7.63 (d, J=8.2 Hz, 1H), 7.10 (dt, J=16.2, 7.1 Hz, 5H), 6.99 (d, J=8.2 Hz, 1H), 4.57 (s, 3H), 4.30 (t, J=7.0 Hz, 2H), 3.82 (d, J=25.8 Hz, 6H), 3.05 (t, J=7.0 Hz, 2H), 2.29-2.20 (m, 6H); $^{13}$C NMR (101 MHz, Methanol-$d_4$) δ 169.48, 165.74, 156.92, 155.57, 149.24, 142.52, 139.50, 139.30, 130.05, 129.59, 127.73, 127.01, 125.84, 123.98, 122.90, 117.45, 108.52, 60.62, 52.38, 49.85, 46.69, 44.97, 40.00, 39.79, 39.58, 39.37, 39.16, 35.62, 13.36, 10.56; LRMS (ESI+): m/z 445.4 (M+H)$^+$.

Example 2-16 21119: 2-(((4-methoxy-3,5-dimethylpyridin-2-yl)methyl)amino)-1-phenethyl-1H-benzo[d]imidazole-5-carboxylic acid

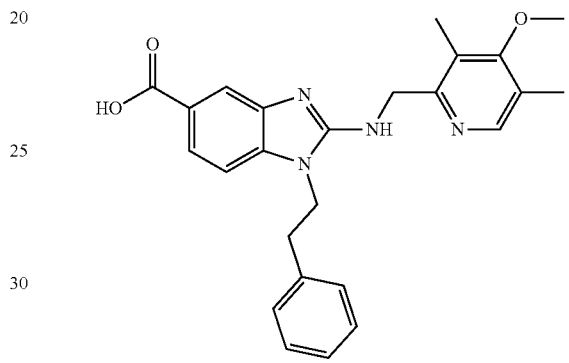

Except that amine is replaced by 2-phenylethanamine, the other reactants and preparation steps are similar to those described in Example 2-4 to afford the title compound.

$^1$H NMR (400 MHz, Methanol-$d_4$) δ 8.19 (s, 1H), 7.89 (d, J=1.5 Hz, 1H), 7.79 (dd, J=8.5, 1.7 Hz, 1H), 7.19-7.07 (m, 6H), 4.73 (s, 2H), 4.48 (t, J=6.8 Hz, 2H), 3.87 (s, 3H), 3.16 (t, J=6.8 Hz, 2H), 2.29 (d, J=14.6 Hz, 6H); $^{13}$C NMR (101 MHz, Methanol-$d_4$) δ 169.15, 167.25, 153.40, 153.06, 148.02, 138.56, 136.34, 130.16, 129.70, 128.21, 128.04, 127.16, 126.66, 126.02, 114.72, 110.61, 61.03, 46.15, 45.80, 34.84, 13.58, 10.68.

Example 2-17 21120: 2-(bis((4-methoxy-3,5-dimethylpyridin-2-yl)methyl)amino)-1-propyl-1H-benzo[d]imidazole-5-carboxylic acid

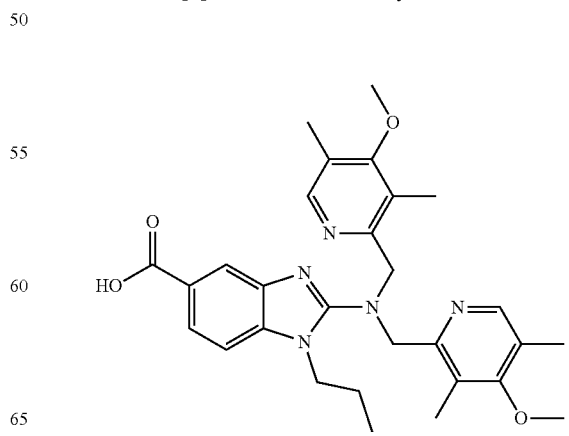

Except that amine is replaced by propan-1-amine, the other reactants and preparation steps are similar to those described in Example 2-4 to afford the title compound.

$^1$H NMR (400 MHz, DMSO-d$_6$) δ 8.09 (s, 2H), 7.88 (d, J=1.6 Hz, 1H), 7.68 (dd, J=8.3, 1.6 Hz, 1H), 7.39 (d, J=8.4 Hz, 1H), 4.63 (s, 4H), 4.11 (t, J=7.9 Hz, 2H), 3.62 (s, 6H), 2.08 (d, J=17.4 Hz, 12H), 1.66 (d, J=7.7 Hz, 2H), 0.73 (t, J=7.3 Hz, 3H).

Example 2-18 21121: 2-(bis((4-methoxy-3,5-dimethylpyridin-2-yl)methyl)amino)-1-phenethyl-1H-benzo[d]imidazole-5-carboxylic acid

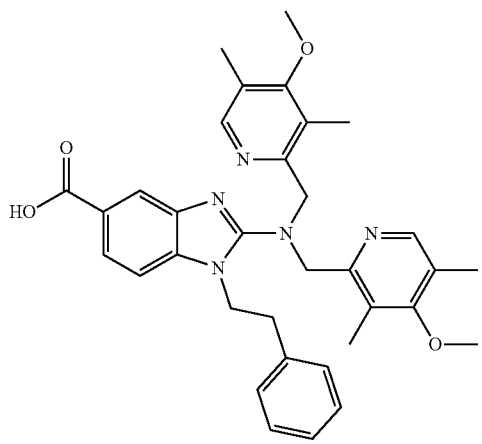 [SMILES: COc1c(C)cnc(CN(Cc2ncc(C)c(OC)c2C)c2nc3cc(C(=O)O)ccc3n2CCc2ccccc2)c1C]

Except that amine is replaced by 2-phenylethanamine, the other reactants and preparation steps are similar to those described in Example 2-4 to afford the title compound.

$^1$H NMR (400 MHz, DMSO-d$_6$) δ 8.07 (s, 2H), 7.89 (d, J=1.5 Hz, 1H), 7.67 (dd, J=8.4, 1.7 Hz, 1H), 7.40 (d, J=8.4 Hz, 1H), 7.19-7.13 (m, 3H), 7.10-7.05 (m, 2H), 4.64 (s, 4H), 4.39 (t, J=8.0 Hz, 2H), 3.59 (s, 6H), 2.97 (t, J=8.1 Hz, 2H), 2.07 (d, J=11.5 Hz, 12H); $^{13}$C NMR (101 MHz, DMSO-d$_6$) δ 168.15, 163.34, 154.81, 148.03, 140.97, 138.79, 138.04, 128.79, 128.39, 126.52, 124.88, 124.76, 123.79, 122.04, 117.97, 109.35, 59.74, 55.15, 45.31, 34.51, 12.91, 10.42.

Example 3-1 NCTU-SUN-26079: Methyl 3-(furan-2-ylmethyl)-2-(((4-methoxy-3,5-dimethylpyridin-2-yl)methyl)amino)-3,4-dihydroquinazoline-7-carboxylate To a solution of 4-(bromomethyl)-3-nitrobenzoic acid 1 (5.0 g, 27.0 mmol) in dry MeOH/CH$_2$Cl$_2$ (3 mL: 30 mL), was added DCC (1.2 equiv) and DMAP (0.005 equiv) and the reaction mixture was stirred at room temperature for 16 hours. The byproduct DCU was filtered off and crude was purified by flash column chromatography to get methyl 4-(bromomethyl)-3-nitrobenzoate 2 (76%) as an off-white solid.

Compound 2 (4.0 g, 14.5 mmol) and 2-aminomethylfuran (3 equiv) in dry CH$_2$Cl$_2$ (50 mL) were stirred at room temperature for 48 hours. Upon completion of reaction the solvent was removed and the crude product was purified by flash column chromatography to afford nitro benzoate 3 (82%).

To a solution of compound 3 (3.65 g, 11.9 mmol) in dry MeOH (100 mL), SnCl$_2$.2H$_2$O (3.5 equiv) was added and the resulting reaction mixture was refluxed for 10 minutes. Upon completion of reaction, the byproduct was filtered through a bed of celite and filtrate was evaporated. The crude product was portioned between 1 N NaOH and ethyl acetate. The aqueous layer was extracted with ethyl acetate (3×20 mL) and the combined layers were dried over MgSO$_4$ and concentrated under reduced pressure to furnish compound 4(87%).

Use DCM to dissolve compound 4 (1.0 g, 3.8 mmol) then add 1.2 equiv. CNBr to react at room temperature. After 8 hours the mixture can be extracted with DCM and water. The solvent was removed and the crude product was purified by flash column chromatography to afford 5 (60%).

To a solution of methyl 2-amino-3-(furan-2-ylmethyl)-3,4-dihydroquinazoline-7-carboxylate 5 (0.3 g, 1.05 mmol) in acetoniritle (20 mL) was added K$_2$CO$_3$ (0.29 g, 2.1 mmol) and KI (0.005 g, 0.03 mmol) followed by 2-(chloromethyl)-4-methoxy-3,5-dimethylpyridine 6 (0.722 g, 3.89 mmol) and the reaction mixture was allowed to reflux for six hours. After 24 hours, the solvent was evaporated and the reaction mixture was diluted with saturated aq. NaHCO$_3$(30 mL) and extracted with EtOAc (3*30 mL).

The combined organic phase was washed with saturated brine (30 mL). The crude product was purified by silica-gel column chromatography using 8% methanol/EtOAc to obtain the pure product NCTU-SUN-26079 as a white solid 0.43 g (70%).

$^1$H NMR (400 MHz, Methanol-d$_4$) δ 8.16 (s, 1H), 7.81 (dd, J=7.9, 1.4 Hz, 1H), 7.56 (dd, J=1.8, 0.8 Hz, 1H), 7.37 (d, J=1.4 Hz, 1H), 7.32 (d, J=7.9 Hz, 1H), 6.60 (d, J=3.3 Hz, 1H), 6.47 (dd, J=3.3, 1.9 Hz, 1H), 5.28 (s, 2H), 4.88 (s, 2H), 4.61 (s, 2H), 3.88 (s, 3H), 3.83 (s, 3H), 2.45 (s, 3H), 2.28 (s, 3H); LRMS (ESI+): m/z 435.3 (M+H)$^+$.

Example 3-2 21106: Methyl 3-(2-(cyclohex-1-en-1-yl)ethyl)-2-(((4-methoxy-3,5-dimethylpyridin-2-yl)methyl)amino)-3,4-dihydroquinazoline-7-carboxylate

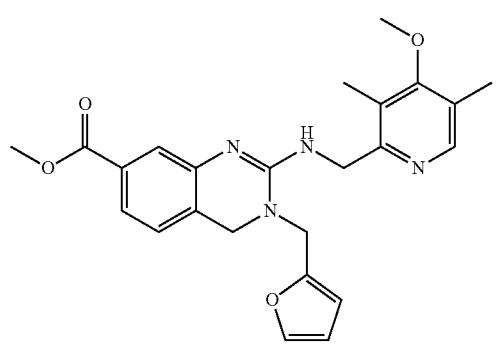

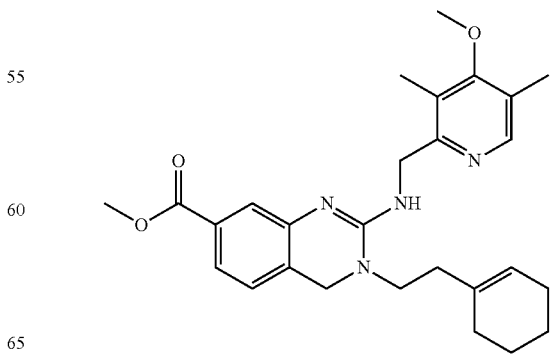

Except that amine is replaced by 2-(cyclohex-1-en-1-yl)ethanamine, the other reactants and preparation steps are similar to those described in Example 3-1 to afford the title compound.

$^1$H NMR (400 MHz, Methanol-d$_4$) δ 8.17 (s, 1H), 7.83 (dd, J=7.9, 1.5 Hz, 1H), 7.40-7.33 (m, 2H), 5.24 (s, 2H), 5.16 (s, 1H), 4.61 (s, 2H), 3.88 (s, 3H), 3.84 (s, 3H), 3.76 (s, 2H), 2.46 (s, 3H), 2.28 (s, 3H), 2.12 (d, J=8.1 Hz, 2H), 1.99 (s, 2H), 1.63-1.55 (m, 4H), 1.43-1.36 (m, 2H); LRMS (ESI+): m/z 314.2 (M+H)$^+$.

Example 3-3 26072: Methyl 2-(bis((4-methoxy-3,5-dimethylpyridin-2-yl)methyl)amino)-3-(furan-2-ylmethyl)-3,4-dihydroquinazoline-7-carboxylate

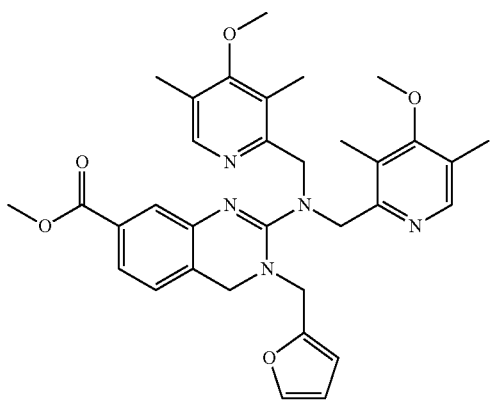

Same as described in Example 3-1 to afford the title compound.

$^1$H NMR (400 MHz, Methanol-d$_4$) δ 8.21-8.19 (m, 1H), 8.07 (d, J=0.8 Hz, 1H), 7.83 (dd, J=7.9, 1.5 Hz, 1H), 7.57 (d, J=1.5 Hz, 1H), 7.43 (dd, J=1.9, 0.8 Hz, 1H), 7.29 (d, J=7.9 Hz, 1H), 6.57 (dd, J=3.4, 0.8 Hz, 1H), 6.41 (dd, J=3.3, 1.9 Hz, 1H), 5.48 (d, J=1.9 Hz, 2H), 4.93 (s, 2H), 4.81 (s, 2H), 4.62 (s, 2H), 3.86 (s, 3H), 3.85 (s, 3H), 3.77 (s, 3H), 2.44 (s, 3H), 2.26 (s, 3H), 2.22 (s, 3H), 2.20 (s, 3H); LRMS (ESI+): m/z 584.31 (M+H)$^+$.

Example 3-4 26091: Methyl 2-(((4-methoxy-3,5-dimethylpyridin-2-yl)methyl)amino)-3-pentyl-3,4-dihydroquinazoline-7-carboxylate

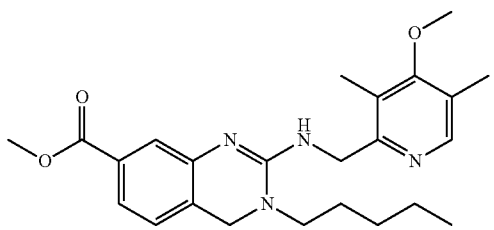

Except that amine is replaced by pentan-1-amine, the other reactants and preparation steps are similar to those described in Example 3-1 to afford the title compound.

$^1$H NMR (400 MHz, Methanol-d$_4$) δ 8.14 (s, 1H), 7.79 (d, J=7.9 Hz, 1H), 7.39 (d, J=7.9 Hz, 1H), 7.32 (s, 1H), 5.24 (s, 2H), 4.70 (s, 2H), 3.86 (s, 3H), 3.81 (s, 3H), 3.64 (t, J=7.8 Hz, 2H), 2.44 (s, 3H), 2.25 (s, 3H), 1.76 (p, J=7.9 Hz, 2H), 1.37 (dp, J=11.3, 7.1, 6.2 Hz, 4H), 0.96-0.83 (m, 3H); $^{13}$C NMR (101 MHz, Methanol-d$_4$) δ 165.84, 165.03, 155.04, 152.00, 148.85, 137.27, 130.52, 128.00, 126.46, 125.87, 125.64, 124.60, 116.16, 59.47, 51.56, 50.90, 50.56, 47.94, 28.23, 26.36, 22.07, 12.93, 12.02, 9.51; LRMS (ESI+): m/z 425.3 (M+H)$^+$.

Example 3-5 26092: Methyl 2-(((4-methoxy-3,5-dimethylpyridin-2-yl)methyl)amino)-3-(4-methoxybenzyl)-3,4-dihydroquinazoline-7-carboxylate

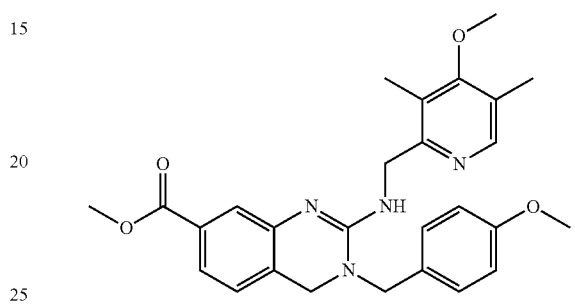

Except that amine is replaced by (4-methoxyphenyl)methanamine, the other reactants and preparation steps are similar to those described in Example 3-1 to afford the title compound.

$^1$H NMR (400 MHz, Methanol-d$_4$) δ 8.09 (s, 1H), 7.71 (dd, J=7.8, 1.4 Hz, 1H), 7.57 (d, J=1.4 Hz, 1H), 7.39 (d, J=8.5 Hz, 2H), 7.31 (d, J=7.8 Hz, 1H), 6.92-6.83 (m, 2H), 5.65 (s, 2H), 5.18 (s, 2H), 4.68 (s, 2H), 3.82 (s, 3H), 3.79 (s, 3H), 3.74 (s, 3H), 2.43 (s, 3H), 2.18 (s, 3H); LRMS (ESI+): m/z 475.3 (M+H)$^+$.

Example 3-6 21110: 2-(((4-methoxy-3,5-dimethylpyridin-2-yl)methyl)amino)-3-(3-methoxypropyl)-3,4-dihydroquinazoline-7-carboxylic acid

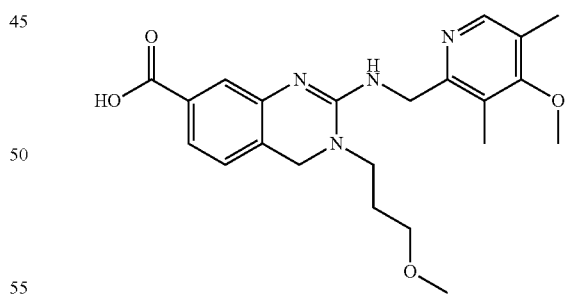

Except that amine is replaced by 3-methoxypropan-1-amine, the other reactants and preparation steps are similar to those described in Example 3-7 to afford the title compound.

$^1$H NMR (400 MHz, Methanol-d$_4$) δ 7.84 (dd, J=7.9, 1.4 Hz, 1H), 7.64 (s, 1H), 7.46 (d, J=1.4 Hz, 1H), 7.40 (d, J=7.9 Hz, 1H), 5.26 (s, 2H), 4.69 (s, 2H), 3.85 (s, 3H), 3.75 (t, J=6.9 Hz, 2H), 3.51 (t, J=5.7 Hz, 2H), 2.27 (s, 3H), 2.04 (d, J=4.9 Hz, 6H), 1.29 (d, J=3.5 Hz, 2H); LRMS (ESI+): m/z 413.3 (M+H)$^+$.

Example 3-7 26089: 3-(furan-2-ylmethyl)-2-(((4-methoxy-3,5-dimethylpyridin-2-yl)methyl)amino)-3,4-dihydroquinazoline-7-carboxylic acid

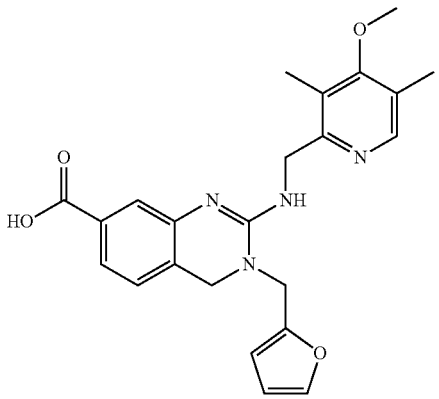 [SMILES: COc1c(C)cnc(CNC2=Nc3cc(C(=O)O)ccc3CN2Cc2ccco2)c1C]

To a solution of 4-(bromomethyl)-3-nitrobenzoic acid 1(5.0 g, 27.0 mmol) in dry MeOH/CH$_2$Cl$_2$ (3 mL: 30 mL), was added DCC (1.2 equiv) and DMAP (0.005 equiv) and the reaction mixture was stirred at room temperature for 16 h. The byproduct DCU was filtered off and crude was purified by flash column chromatography to get methyl 4-(bromomethyl)-3-nitrobenzoate 2 (76%) as an off-white solid.

Compound 2 (4.0 g, 14.5 mmol) and 2-Aminomethyl-furan (3 equiv) in dry CH$_2$Cl$_2$ (50 mL) were stirred at room temperature for 48 hours. Upon completion of reaction the solvent was removed and the crude product was purified by flash column chromatography to afford nitro benzoate 3 (82%).

To a solution of compound 3 (3.65 g, 11.9 mmol) in dry MeOH (100 mL), SnCl$_2$.2H$_2$O (3.5 equiv) was added and the resulting reaction mixture was refluxed for 10 min. Upon completion of reaction, the byproduct was filtered through a bed of celite and filtrate was evaporated. The crude product was portioned between 1 N NaOH and ethyl acetate. The aqueous layer was extracted with ethyl acetate (3×20 mL) and the combined layers were dried over MgSO$_4$ and concentrated under reduced pressure to furnish compound 4(87%).

Use DCM to dissolve compound 4 (1.0 g, 3.8 mmol) then add 1.2 equiv. CNBr to react at room temperature. After 8 hours the mixture can be extracted with DCM and water. The solvent was removed and the crude product was purified by flash column chromatography to afford 5 (60%).

To a solution of methyl 2-amino-3-(furan-2-ylmethyl)-3,4-dihydroquinazoline-7-carboxylate 5 (0.3 g, 1.05 mmol) in acetoniritle (20 mL) was added K$_2$CO$_3$ (0.29 g, 2.1 mmol) and KI (0.005 g, 0.03 mmol) followed by 2-(chloromethyl)-4-methoxy-3,5-dimethylpyridine 6 (0.722 g, 3.89 mmol) and the reaction mixture was allowed to reflux for six hours. After 24 hours, the solvent was evaporated and the reaction mixture was diluted with saturated aq. NaHCO$_3$(30 mL) and extracted with EtOAc (3*30 mL).

The combined organic phase was washed with saturated brine (30 mL). The crude product was purified by silica-gel column chromatography using 8% methanol/EtOAc to obtain Methyl 3-(furan-2-ylmethyl)-2-(((4-methoxy-3,5-dimethylpyridin-2-yl)methyl)amino)-3,4-dihydroquinazoline-7-carboxylate 7 0.43 g (70%).

And add NaOH (0.198 g, 4.95 mmol) to a solution of methyl 3-(furan-2-ylmethyl)-2-(((4-methoxy-3,5-dimethylpyridin-2-yl)methyl)amino)-3,4-dihydroquinazoline-7-carboxylate 7 (0.43 g, 0.99 mmol) in the EtOH/H$_2$O (1/1, 10 mL) in the reflux condition. After 1 hour, the solvent was evaporated and the reaction mixture was diluted with saturated aq. HCl (30 mL) and extracted with EtOAc (3*30 mL). The combined organic phase was washed with saturated brine (30 mL). The crude product was purified by silica-gel column chromatography using 20% methanol/EtOAc to obtain the pure product as a white solid 0.27 g (65%).

$^1$H NMR (400 MHz, Methanol-d$_4$) δ 8.07 (s, 1H), 7.70 (d, J=7.9 Hz, 1H), 7.53 (d, J=1.8 Hz, 1H), 7.35 (s, 1H), 7.14 (d, J=7.8 Hz, 1H), 6.57 (d, J=3.2 Hz, 1H), 6.43 (dd, J=3.2, 1.8 Hz, 1H), 5.22 (s, 2H), 4.84 (s, 2H), 4.53 (s, 2H), 3.82 (s, 3H), 2.40 (s, 3H), 2.22 (s, 3H); $^{13}$C NMR (101 MHz, Methanol-d$_4$) δ 171.74, 164.87, 155.39, 151.73, 148.52, 147.49, 143.54, 138.56, 136.13, 126.27, 125.93, 124.64, 124.63, 116.56, 110.30, 109.86, 59.40, 50.46, 47.46, 46.94, 46.47, 11.97, 9.33; LRMS (ESI+): m/z 421.2 (M+H)$^+$.

Example 3-8 26090: 2-(((4-methoxy-3,5-dimethylpyridin-2-yl)methyl)amino)-3-pentyl-3,4-dihydroquinazoline-7-carboxylic acid

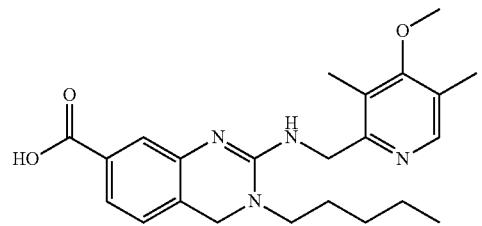 [SMILES: CCCCCN1Cc2ccc(C(=O)O)cc2N=C1NCc1ncc(C)c(OC)c1C]

Except that amine is replaced by pentan-1-amine, the other reactants and preparation steps are similar to those described in Example 3-7 to afford the title compound.

$^1$H NMR (400 MHz, Methanol-d$_4$) δ 8.03 (dd, J=8.4, 1.4 Hz, 1H), 7.96 (s, 1H), 7.84 (d, J=1.3 Hz, 1H), 7.55 (d, J=8.4 Hz, 1H), 3.83 (s, 3H), 2.41 (s, 3H), 2.22 (s, 3H), 1.92-1.83 (m, 2H), 1.43 (tt, J=5.7, 2.8 Hz, 4H), 1.29 (d, J=4.0 Hz, 2H), 0.97-0.92 (m, 3H); LRMS (ESI+): m/z 411.3 (M+H)$^+$.

Example 4-1 NCTU-SUN-12082: Methyl 1-(2-(cyclohex-1-en-1-yl)ethyl)-2-(((4-methoxy-3,5-dimethylpyridin-2-yl)methyl)thio)-1H-benzo[d]imidazole-5-carboxylate

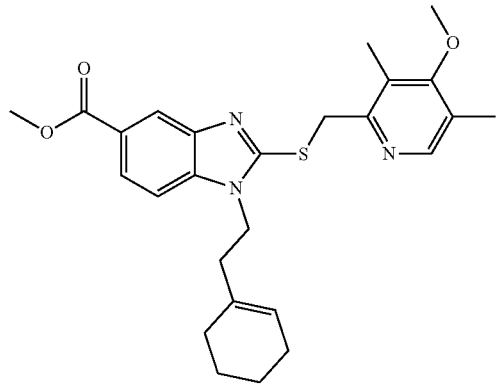

To a solution of 4-fluoro-3-nitrobenzoic acid 1, $H_2SO_4$ (5 mL, 0.3 M) is added and the reaction mixture is heated to reflux. The solvent is removed under reduced pressure; crude reaction mixture is dissolved in EtOAc. The EtOAc layer was dried over anhydrous $MgSO_4$ and evaporated to get methyl 4-fluoro-3-nitrobenzoate 2 as a white solid.

Compound 2 and 2-(cyclohex-1-en-1-yl)ethanamine were stirred at room temperature for 2 hours. Upon completion of reaction the solvent was removed and the crude product was purified to afford nitro benzoates 3.

To a solution of compound 3, zinc dust and ammonium formate are added and the resulting reaction mixture is stirred at room temperature. Upon completion of reaction, Zn dust is filtered and the filtrate is evaporated and the product is dissolved in $CH_2C_2$. The precipitated ammonium formate was filtered off and the solvent was evaporated to furnish compound 4.

To the stirred solution of compound 4 is added carbon disulfide and KOH at 50° C. in the ethanol for 8 hours. The mixture can be neutralized by acetic acid and extracted with EtOAc and water. The solvent was removed and the crude product was purified to afford 5.

To a solution of methyl 1-(2-(cyclohex-1-en-1-yl)ethyl)-2-thioxo-2,3-dihydro-1H-benzo[d]imidazole-5-carboxylate 5 is added $K_2CO_3$ and KI followed by 2-(chloromethyl)-4-methoxy-3,5-dimethylpyridine 6 and the reaction mixture was allowed to reflux. The solvent is evaporated and the reaction mixture is diluted and extracted with EtOAc.

The combined organic phase was washed with saturated brine. The crude product was purified to obtain the pure product NCTU-SUN-12082 as a white solid 0.053 g (71%).

$^1$H NMR (300 MHz, Acetone-$d_6$) δ 8.24 (d, J=1.2 Hz, 1H), 8.20 (s, 1H), 7.91 (dd, J=8.5, 1.4 Hz, 1H), 7.53 (d, J=8.5 Hz, 1H), 5.22 (s, 1H), 4.83 (s, 2H), 4.28 (t, J=7.0 Hz, 2H), 3.91 (s, 3H), 3.80 (s, 3H), 2.47-2.35 (m, 5H), 2.25 (s, 3H), 1.99 (m, 2H), 1.80 (m, 2H), 1.62-1.38 (m, 4H).

Example 4-2 12083: 1-(2-(cyclohex-1-en-1-yl)ethyl)-2-(((4-methoxy-3,5-dimethylpyridin-2-yl)methyl)thio)-1H-benzo[d]imidazole-5-carboxylic acid

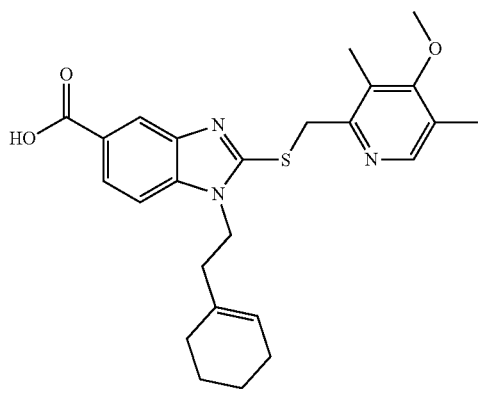 [SMILES: COc1c(C)cnc(CSc2nc3cc(C(=O)O)ccc3n2CCC2=CCCCC2)c1C]

To a solution of 4-fluoro-3-nitrobenzoic acid 1, $H_2SO_4$ (5 mL, 0.3 M) is added and the reaction mixture is heated to reflux. The solvent is removed under reduced pressure; crude reaction mixture is dissolved in EtOAc. The EtOAc layer was dried over anhydrous $MgSO_4$ and evaporated to get methyl 4-fluoro-3-nitrobenzoate 2 as a white solid.

Compound 2 and 2-(cyclohex-1-en-1-yl)ethanamine were stirred at room temperature for 2 h. Upon completion of reaction the solvent was removed and the crude product was purified to afford nitro benzoates 3.

To a solution of compound 3, zinc dust and ammonium formate are added and the resulting reaction mixture is stirred at room temperature. Upon completion of reaction, Zn dust is filtered and the filtrate is evaporated and the product is dissolved in $CH_2C_2$. The precipitated ammonium formate was filtered off and the solvent was evaporated to furnish compound 4.

To the stirred solution of compound 4 is added carbon disulfide and KOH at 50° C. in the ethanol for 8 hours. The mixture can be neutralized by acetic acid and extracted with EtOAc and water. The solvent was removed and the crude product was purified to afford 5.

To a solution of methyl 1-(2-(cyclohex-1-en-1-yl)ethyl)-2-thioxo-2,3-dihydro-1H-benzo[d]imidazole-5-carboxylate 5 is added $K_2CO_3$ and KI followed by 2-(chloromethyl)-4-methoxy-3,5-dimethylpyridine 6 and the reaction mixture was allowed to reflux. The solvent is evaporated and the reaction mixture is diluted and extracted with EtOAc.

The combined organic phase was washed with saturated brine. The crude product was purified to obtain Methyl 1-(2-(cyclohex-1-en-1-yl)ethyl)-2-(((4-methoxy-3,5-dimethylpyridin-2-yl)methyl)thio)-1H-benzo[d]imidazole-5-carboxylate 7 0.053 g (71%).

And add NaOH (0.0251 g, 0.63 mmol) to a solution of Methyl 1-(2-(cyclohex-1-en-1-yl)ethyl)-2-(((4-methoxy-3,5-dimethylpyridin-2-yl)methyl)thio)-1H-benzo[d]imidazole-5-carboxylate 7 (0.053 g, 0.126 mmol) in the EtOH/$H_2O$ (1/1, 3 mL) in the reflux condition. After 1 hour, the solvent was evaporated and the reaction mixture was diluted with saturated aq. HCl (10 mL) and extracted with EtOAc (3*10 mL). The combined organic phase was washed with saturated brine (30 mL). The crude product was purified by silica-gel column chromatography using 20% methanol/EtOAc to obtain the pure product NCTU-SUN-12083 as a white solid 0.030 g (65%).

$^1$H NMR (300 MHz, $CD_3OD$) δ 8.30 (d, J=1.4 Hz, 1H), 8.14 (s, 1H), 7.98 (dd, J=8.5, 1.5 Hz, 1H), 7.49 (d, J=8.5 Hz, 1H), 5.51 (s, 2H), 5.08 (s, 1H), 4.71 (s, 2H), 4.24 (t, J=6.8 Hz, 2H), 3.79 (s, 3H), 2.44-2.31 (m, 5H), 2.27 (s, 3H), 2.04-1.89 (m, 2H), 1.88-1.70 (m, 2H), 1.62-1.39 (m, 4H).

Example 4-3 12084: Methyl 1-(2-(cyclohex-1-en-1-yl)ethyl)-2-(((4-methoxy-3,5-dimethylpyridin-2-yl)methylsulfinyl)-1H-benzo[d]imidazole-5-carboxylate

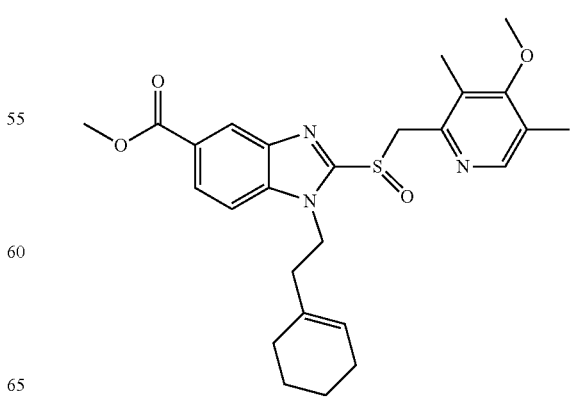

To a solution of 4-fluoro-3-nitrobenzoic acid 1, H₂SO₄ (5 mL, 0.3 M) is added and the reaction mixture is heated to reflux. The solvent is removed under reduced pressure; crude reaction mixture is dissolved in EtOAc. The EtOAc layer was dried over anhydrous MgSO₄ and evaporated to get methyl 4-fluoro-3-nitrobenzoate 2 as a white solid.

Compound 2 and 2-(cyclohex-1-en-1-yl)ethanamine were stirred at room temperature for 2 hours. Upon completion of reaction the solvent was removed and the crude product was purified to afford nitro benzoates 3.

To a solution of compound 3, zinc dust and ammonium formate are added and the resulting reaction mixture is stirred at room temperature. Upon completion of reaction, Zn dust is filtered and the filtrate is evaporated and the product is dissolved in CH₂C₂. The precipitated ammonium formate was filtered off and the solvent was evaporated to furnish compound 4.

To the stirred solution of compound 4 is added carbon disulfide and KOH at 50° C. in the ethanol for 8 hours. The mixture can be neutralized by acetic acid and extracted with EtOAc and water. The solvent was removed and the crude product was purified to afford 5.

To a solution of methyl 1-(2-(cyclohex-1-en-1-yl)ethyl)-2-thioxo-2,3-dihydro-1H-benzo[d]imidazole-5-carboxylate 5 is added K₂CO₃ and KI followed by 2-(chloromethyl)-4-methoxy-3,5-dimethylpyridine 6 and the reaction mixture was allowed to reflux. The solvent is evaporated and the reaction mixture is diluted and extracted with EtOAc.

The combined organic phase was washed with saturated brine. The crude product was purified to obtain Methyl 1-(2-(cyclohex-1-en-1-yl)ethyl)-2-(((4-methoxy-3,5-dimethylpyridin-2-yl)methyl)thio)-1H-benzo[d]imidazole-5-carboxylate 7 0.053 g (71%).

And add mCPBA (0.0058 g, 0.034 mmol) to a solution of Methyl 1-(2-(cyclohex-1-en-1-yl)ethyl)-2-(((4-methoxy-3,5-dimethylpyridin-2-yl)methyl)thio)-1H-benzo[d]imidazole-5-carboxylate 7 (0.053 g, 0.0126 mmol) in the DCM/MeOH (9/1, 4.5 mL) in the ice bath. Then, add NaHCO₃ (0.0007 g, 0.0088 mmol) and remove the ice bath. Let the crude stir at room temperature in 1 hour. The reaction mixture was washed with DCM (5 mL). The solvent was evaporated and the to obtain the pure product NCTU-SUN-12084 as a white solid 0.030 g (65%).

¹H NMR (300 MHz, CDCl₃) δ 8.55 (s, 1H), 8.13 (s, 1H), 8.10 (dd, J=8.7, 1.5 Hz, 1H), 7.43 (d, J=8.8 Hz, 1H), 5.03 (q, J=12.9 Hz, 3H), 4.59-4.35 (t, J=8.3 Hz, 2H), 4.58-4.36 (m, 2H), 3.97 (s, 3H), 3.71 (s, 3H), 2.49 (t, J=8.3 Hz, 2H), 2.30 (s, 3H), 2.22 (s, 3H), 2.03-1.78 (m, 4H), 1.51 (m, 4H).

Example 5-1 12092: 2-(((4-methoxy-3,5-dimethylpyridin-2-yl)methyl)thio)-1H-benzo[d]imidazol-5-yl (((9H-fluoren-9-yl)methoxy)carbonyl)glycinate

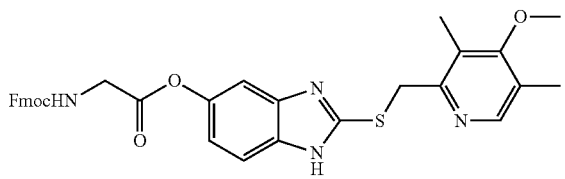

To a solution of 2-thioxo-2,3-dihydro-1H-benzo[d]imidazol-5-yl 2-((((9H-fluoren-9-yl)methoxy)carbonyl)amino)acetate 1 (0.08 g, 0.18 mmol) in ethanol (9 mL) was added NaOH (0.079 g, 0.198 mmol) followed by 2-(chloromethyl)-4-methoxy-3,5-dimethylpyridine 2 (0.367 g, 0.198 mmol) and the reaction mixture was allowed to reflux for one hour. Once the reaction was completed, the solvent was evaporated and the crude product was purified by silica-gel column chromatography using 2% MeOHDCM to obtain the pure product NCTU-SUN-12092 as a white solid. 0.31 g, 54.5%.

¹H NMR (300 MHz, Acetone-d₆) δ 8.26 (s, 1H), 7.87 (d, J=7.4 Hz, 2H), 7.74 (d, J=7.4 Hz, 2H), 7.51 (d, J=8.6 Hz, 1H), 7.41 (t, J=7.3 Hz, 2H), 7.32 (t, J=7.4 Hz, 3H), 7.14 (t, J=6.6 Hz, 1H), 6.95 (dd, J=8.7, 2.1 Hz, 1H), 4.67 (s, 2H), 4.40 (d, J=7.3 Hz, 2H), 4.36-4.21 (m, 3H), 3.80 (s, 3H), 2.36 (s, 3H), 2.25 (s, 3H).

Example 5-2 12093: 2-(((4-methoxy-3,5-dimethylpyridin-2-yl)methyl)thio)-1H-benzo[d]imidazol-5-yl (tert-butoxycarbonyl)glycinate

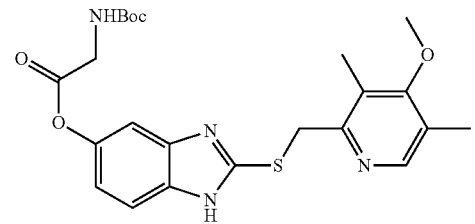 [SMILES: COc1c(C)cnc(CSc2nc3cc(OC(=O)CNC(=O)OC(C)(C)C)ccc3[nH]2)c1C]

Except that imidazole is replaced by 2-thioxo-2,3-dihydro-H-benzo[d]imidazol-5-yl 2-((tert-butoxycarbonyl)amino)acetate, the other reactants and preparation steps are similar to those described in Example 5-1 to afford the title compound.

¹H NMR (300 MHz, Acetone) δ 8.27 (s, 1H), 7.50 (s, 1H), 7.29 (d, J=2.1 Hz, 1H), 6.93 (dd, J=8.6, 2.1 Hz, 1H), 6.50 (s, 1H), 4.67 (s, 2H), 4.12 (d, J=6.2 Hz, 2H), 3.81 (s, 3H), 2.38 (s, 3H), 2.26 (s, 3H), 1.45 (s, 9H).

Example 5-3 12094: 2-(((4-methoxy-3,5-dimethylpyridin-2-yl)methyl)thio)-1H benzo[d]-imidazole-5-yl (S)-2-((((9H-fluoren-9-yl)methoxy)carbonyl)amino)-2-phenylacetate

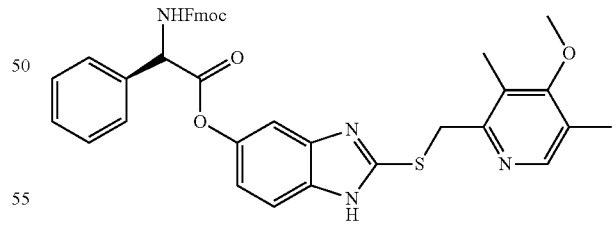

Except that imidazole is replaced by (S)-2-thioxo-2,3-dihydro-1H-benzo[d]imidazol-5-yl 2-((((9H-fluoren-9-yl)methoxy)carbonyl)amino)-2-phenylacetate, the other reactants and preparation steps are similar to those described in Example 5-1 to afford the title compound.

¹H NMR (300 MHz, Acetone-d₆) δ 8.24 (s, 1H), 7.85 (d, J=7.5 Hz, 2H), 7.75 (d, J=7.4 Hz, 2H), 7.65 (d, J=7.2 Hz, 2H), 7.52-7.39 (m, 6H), 7.32 (m, 2H), 7.22 (d, J=1.6 Hz, 1H), 6.83 (dd, J=9.1, 1.5 Hz, 1H), 5.67 (s, 1H), 4.66 (s, 2H), 4.48-4.25 (m, 3H), 2.35 (s, 3H), 2.25 (s, 3H).

Example 6-1 NCTU-SUN-22138: 5-methoxy-2-((2-methoxy-3,6-dimethylbenzyl)thio)-1H-benzo[d]imidazole

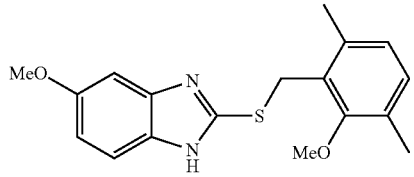 [SMILES: COc1ccc2[nH]c(SCc3c(C)ccc(C)c3OC)nc2c1]

To a solution of 2-methoxy-1,3,4-trimethylbenzene 1 (0.3 g, 2.00 mmol) in chloroform (30 mL) was added NBS (0.177 g, 1.00 mmol) and in the light-induced reactions, two Philips "IR 250 W lamps were placed at such a distance from the reaction flask that reflux was maintained. Once the reaction was completed, the solvent was evaporated and the crude product was purified by silica-gel column chromatography using hexane to obtain brominated product 2 0.092 g, 20%.

To a solution of t brominated product 2 (0.1 g, 0.43 mmol) in ethanol (2 mL) was added NaOH (0.017 g, 0.43 mmol) followed by 2-(chloromethyl)-4-methoxy-3,5-dimethylpyridine 3 (0.071 g, 0.39 mmol) and the reaction mixture was allowed to reflux for one hour. Once the reaction was completed, the solvent was evaporated and the crude product was purified by silica-gel column chromatography using 2% MeOHDCM to obtain NCTU-SUN-22138 0.077 g, 60%.

LRMS (ESI+): m/z 329.2 (M+H)$^+$

Example 6-2 22141: 2-((2-methoxy-3,6-dimethylbenzyl)thio)-1H-benzo[d]imidazol-5-ol

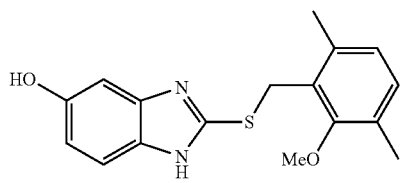 [SMILES: COc1c(C)ccc(C)c1CSc1nc2cc(O)ccc2[nH]1]

To a solution of 2-methoxy-1,3,4-trimethylbenzene 1 (0.3 g, 2.00 mmol) in chloroform (30 mL) was added NBS (0.177 g, 1.00 mmol) and in the light-induced reactions, two Philips "IR 250 W lamps were placed at such a distance from the reaction flask that reflux was maintained. Once the reaction was completed, the solvent was evaporated and the crude product was purified by silica-gel column chromatography using hexane to obtain brominated product 2 0.092 g, 20%.

To a solution of t brominated product 2 (0.1 g, 0.43 mmol) in ethanol (2 mL) was added NaOH (0.017 g, 0.43 mmol) followed by 2-(chloromethyl)-4-hydroxy-3,5-dimethylpyridine 3 (0.071 g, 0.39 mmol) and the reaction mixture was allowed to reflux for one hour. Once the reaction was completed, the solvent was evaporated and the crude product was purified by silica-gel column chromatography using 2% MeOHDCM to obtain NCTU-SUN-22138 0.077 g, 60%.

LRMS (ESI+): m/z 315.1 (M+H)$^+$

Example 6-3 21133: 2-((3-(bromomethyl)-2-((tert-butyldimethylsilyl)oxy)-6-methylbenzyl)thio)-5-methoxy-1H-benzo[d]imidazole

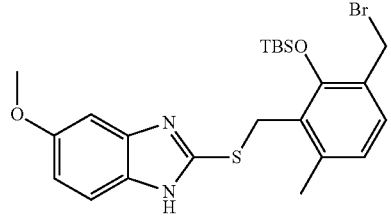 [SMILES: COc1ccc2[nH]c(SCc3c(C)ccc(CBr)c3O[Si](C)(C)C(C)(C)C)nc2c1]

To a solution of tert-butyldimethyl(2,3,6-trimethylphenoxy)silane 1 (1.2 g, 4.7 mmol) in chloroform (50 mL) was added NBS (1.7 g, 9.5 mmol) and in the light-induced reactions, two Philips "IR 250 W lamps were placed at such a distance from the reaction flask that reflux was maintained. Once the reaction was completed, the solvent was evaporated and the crude product was purified by silica-gel column chromatography using hexane to obtain dibrominated product 2 0.31 g, 20%.

To a solution of dibrominated product 2 (0.3 g, 0.90 mmol) in ethanol (9 mL) was added NaOH (0.036 g, 0.90 mmol) followed by 2-(chloromethyl)-4-methoxy-3,5-dimethylpyridine 3 (0.148 g, 0.82 mmol) and the reaction mixture was allowed to reflux for one hour. Once the reaction was completed, the solvent was evaporated and the crude product was purified by silica-gel column chromatography using 2% MeOH/DCM to obtain NCTU-SUN-21133 0.23 g, 60%.

$^1$H NMR (400 MHz, Chloroform-d) δ 7.43 (d, J=8.8 Hz, 1H), 7.16 (s, 1H), 7.04 (d, J=2.3 Hz, 1H), 6.82 (d, J=2.3 Hz, 1H), 4.69 (s, 2H), 3.78 (s, 4H), 2.22 (s, 3H), 2.13 (s, 4H), 0.98 (s, 9H), 0.09 (s, 6H).

LRMS (ESI+): m/z 507.1 (M+H)$^+$

Example 6-4 22139: 5-methoxy-2-((2-methoxy-3,6-dimethylbenzyl)sulfinyl)-1H-benzo[d]imidazole

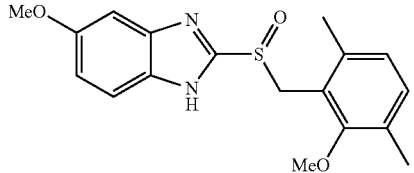 [SMILES: COc1ccc2[nH]c(S(=O)Cc3c(C)ccc(C)c3OC)nc2c1]

To a solution of 2-methoxy-1,3,4-trimethylbenzene 1 (0.3 g, 2.00 mmol) in chloroform (30 mL) was added NBS (0.177 g, 1.00 mmol) and in the light-induced reactions, two Philips "IR 250 W lamps were placed at such a distance from the reaction flask that reflux was maintained. Once the reaction was completed, the solvent was evaporated and the crude product was purified by silica-gel column chromatography using hexane to obtain brominated product 2 0.092 g, 20%.

To a solution of t brominated product 2 (0.1 g, 0.43 mmol) in ethanol (2 mL) was added NaOH (0.017 g, 0.43 mmol) followed by 2-(chloromethyl)-4-methoxy-3,5-dimethylpyridine 3 (0.071 g, 0.39 mmol) and the reaction mixture was allowed to reflux for one hour. Once the reaction was completed, the solvent was evaporated and the crude product was purified by silica-gel column chromatography using 2% MeOH/DCM to obtain 5-methoxy-2-((2-methoxy-3,6-dimethylbenzyl)thio)-1H-benzo[d]imidazole 3 0.077 g, 60%.

And add mCPBA (0.069 g, 0.40 mmol) to a solution of 5-methoxy-2-((2-methoxy-3,6-dimethylbenzyl)thio)-1H-benzo[d]imidazole 3 (0.077 g, 0.23 mmol) in the DCM/MeOH (9/1, 10 mL) in the ice bath. Then, add NaHCO$_3$ (0.013 g, 0.16 mmol) and remove the ice bath. Let the crude stir at room temperature in 1 h. The reaction mixture was washed with DCM (10 mL). The solvent was evaporated and the to obtain the pure product as a white solid 0.047 g (65%).

LRMS (ESI+): m/z 345.1 (M+H)$^+$

Example 7 DAAO Enzymatic Assay

The DAAO enzymatic activity assay was modified according to the report of Oguri et al (*Oguri, S., Screening of d-amino acid oxidase inhibitor by a new multi-assay method. Food chemistry* 2007, 100 (2), 616). The DAAO activity was measured by using substrate D-alanine reaction produced hydrogen peroxide (H$_2$O$_2$) to further react with 3-(4-hydroxyphenyl) propionic acid (HPPA). The HPPA were oxidized by H$_2$O$_2$ and peroxidase to become the fluorogenic dimer which was measured to represent the activity of DAAO.

For porcine kidney DAO IC50 assay, the DAO substrate was prepared in 50 mM D-alanine (dissolved in 0.2 M Tris-HCl buffer, pH 8.3). A 100 µl of D-alanine solution was mixed with 4 µl (in 100% dimethyl sulfoxide, DMSO) of different concentrations of candidate compounds shown in tables below ranging from 48.83 µM, 97.66 µM, 195.31 µM, 390.63 µM, 781.25 µM, 1.56 mM, 3.13 mM, 6.25 mM, 12.50 mM, 25.00 mM, and 50.00 mM, with a final DMSO concentration of 0.167% in each reaction concentration. 10 µl of D-alanine and candidate compound mixture was incubated with 220 µl of Reaction Master Mix in black 96 well plate at 37° C. for 5 minutes. The Reaction Master Mix contained 110 µl of 5 U/mL porcine kidney DAO (Sigma-Aldrich, USA) solution (dissolved with 0.2 M Tris-HCl buffer, pH 8.3), 1.1 mL of 15 U/mL peroxidase solution (dissolved with 0.2 M Tris-HCl buffer, pH 8.3), 1.1 mL of 20 mM HPPA solution (dissolved with 0.2 M Tris-HCl buffer, pH 8.3), and 22 ml of 2 M Tris-HCl buffer (pH 8.3) for 110 reaction assays.

Fluorescence intensity (Fs) was measured at 405 nm by irradiation excitation at 320 nm. The higher the DAO enzymatic activity was, the higher the fluorescence intensity. The fluorometric inhibition indicator (Fi) was obtained from the following equation: Fi=(Fs-F$_{Drug}$)/(F$_{DMSO}$), where the fluorescent drug blank (F$_{Drug}$) was measured in the drug mixture solution (using 0.2 M Tris HCl buffer, pH 8.3, without D-alanine). A DMSO blank (F$_{DMSO}$) was measured under a 100% DMSO solution.

Although FAD is generally included in the reaction mixture in the D-amino acid oxidase assay since it easily dissociates from the holoenzyme, the present method was performed without FAD. The inhibitory effect of DAO inhibitors was compared by using inhibitory concentrations leading to 50% inhibition of DAAO activity (IC$_{50}$). The IC$_{50}$ values were calculated by nonlinear regression model using GraphPad Prism, version 5(GraphPad Software, Inc., La Jolla, Calif.). The results of DAO IC50 assay of the candidate compounds of the invention are shown in the table below.

| | | pkDAO Enzymatic Assay | |
|---|---|---|---|
| ID | M.W. | IC50 (uM) | IC50 95% Confidence Range (uM) |
| CBIO | 169.6 | 0.5827 | 0.5165 to 0.6573 |
| RS-D7 | 331.39 | 1.1850 | 0.9970 to 1.408 |
| 12083 | 451.5811 | 366.6000 | 302.2 to 444.8 |
| 21105 | 583.73 | 300.8000 | 223.0 to 405.9 |
| 26072 | 583.69 | 236.4000 | 211.2 to 264.5 |
| 21106 | 462.59 | 488.1000 | 309.4 to 769.9 |
| 21132 | 431.15 | 64.1500 | 60.86 to 67.61 |
| 13084 | 563.56 | 181.2000 | 154.3 to 212.8 |
| 12122 | 425.4577 | 12.5400 | 11.55 to 13.62 |
| 21122 | 373.1096 | 21.0900 | 16.63 to 26.75 |
| 11020 | 465.13 | 10.4400 | 9.549 to 11.40 |
| 12124 | 399.46 | 11.1600 | 10.11 to 12.32 |
| 12125 | 413.49 | 13.3100 | 12.26 to 14.44 |
| 25016 | 415.16 | 13.3600 | 12.39 to 14.42 |
| 28092 | 399.13 | 46.7000 | 41.85 to 52.10 |
| 28094 | 449.52 | 21.1100 | 19.18 to 23.23 |
| 25027 | 413.1409 | 21.0000 | 19.70 to 22.37 |

Example 8 Cell-Based DAO Assay

Neuronal Cell Culture

The SK-N-SH neuroblastoma cell line was purchased from American Type Culture Collection (ATCC). It was cultured in MEM media (Invitrogen/GIBCO, Rockville, Md.) supplemented with 10% fetal bovine serum, 1×NEAA (Invitrogen/GIBCO) at 37° C. with 5% CO2 in a humidified atmosphere. Cells were trypsinized and plated into a black 96-well plate (NUNC No. 237108) at a density of 125,000 cells/well in 50 µl before cell-based DAO assay.

Cell-Based DAO Assay

The cellular DAO activity assay was using a method modified according to the report of Brandish et al. (Brandish, P. E., et al., *A cell-based ultra-high-throughput screening assay for identifying inhibitors of D-amino acid oxidase. J Biomol Screen,* 2006. 11(5): p. 481-7). SK-N-SH cells were suspended in assay buffers of HANKS buffer solution (Invitrogen/GIBCO No. 14025-092) with 20 mM HEPES. D-serine of (final concentration 50 mM) was added in each well as the substrate for DAO enzyme. The Amplex Red Hydrogen Peroxide/Proxidase Assay Kit (Molecular Probes/Invitrogen, cat. A22188) was used to measure H$_2$O$_2$ production which diffused across the cell membrane into the assay medium after DAO reaction. After seeding cells into black 96-well plate (Nunc No. 237108, Denmark), 50 µl of SK-N-SH cells (125,000 cells/well) was mixed with 50 µl drug solution (2.5 fold of interesting final concentration) and incubate at 37° C. with 5% CO$_2$ in a humidified atmosphere for 30 minutes. After 30 minutes later, 25 µl of a 5 fold mixture containing D-serine, horseradish peroxidase (HRP), and Amplex Red was added into wells containing 100 µl of cell-drugs mixture and incubated at 37° C. with 5% CO$_2$ in a humidified atmosphere for 3 hours. The final concentration of DMSO is below 1%. The fluorescence signal was then detected in SpectraMax M2e microplate reader (Molecular Devices, USA) with excitation at 544 nm and emission at 590 nm. The optimized assay buffer contained a final concentration of 50 mM D-serine, 0.625 units HRP, and 50 µM Amplex Red in a 125 µl assay volume. The results of the cell-base DAO assay of the candidate compounds of the invention are shown in the table below.

| | | Cell-base DAO assay SK-N-SH 1.25*10^5 cells/well (Drug treated for 3.5 hr) | | | |
|---|---|---|---|---|---|
| | | Relative DAO activity normalize to DMSO at Final Conc. | | Cell-based IC50 assay | |
| ID | M.W. | 100 uM | 10 uM | IC50 (uM) | IC50 95% Confidence Range (uM) |
| CBIO | 169.6 | 0.83 | 1.00 | 392.30 | 281.4 to 547.0 |
| RS-D7 | 331.39 | 0.69 | 1.05 | 141.00 | 81.07 to 245.1 |
| 12083 | 451.5811 | 0.48 | 0.62 | 74.15 | 27.04 to 203.4 |
| 21105 | 583.73 | 0.58 | 0.89 | 218.80 | 98.89 to 484.3 |
| 26072 | 583.69 | 0.74 | 0.87 | 393.00 | 215.3 to 717.2 |
| 21106 | 462.59 | 0.77 | 1.02 | 477.60 | 245.5 to 929.2 |
| 21132 | 431.15 | 0.61 | 0.94 | 174.80 | 137.9 to 221.7 |
| 13084 | 563.56 | 0.49 | 0.71 | 34.91 | 21.34 to 57.09 |
| 12122 | 425.4577 | 0.57 | 0.98 | 146.60 | 106.1 to 202.6 |
| 21122 | 373.1096 | 0.50 | 0.99 | 149.40 | 94.76 to 235.5 |
| 11020 | 465.13 | 0.67 | 0.97 | 220.90 | 121.5 to 401.9 |
| 12124 | 399.46 | 0.36 | 0.97 | 107.60 | 73.47 to 157.6 |
| 12125 | 413.49 | 0.50 | 0.80 | 122.20 | 61.25 to 243.7 |
| 25016 | 415.16 | 0.62 | 1.00 | 187.60 | 107.7 to 326.8 |
| 28092 | 399.13 | 0.58 | 0.94 | 136.40 | 86.51 to 215.1 |
| 28094 | 449.52 | 0.58 | 1.10 | 121.50 | 73.91 to 199.9 |
| 25027 | 413.1409 | 0.69 | 1.15 | 240.20 | 142.0 to 406.3 |

Example 9 Animal Studies of Potency in Treating Schizophrenia Symptoms

Drug Efficacy Screening

The NMDA-receptor antagonist MK-801-induced negative or cognitive deficits in C57BL/6 mice were in a well-established drug-induced schizophrenia mouse model and as a useful pharmacological animal model to identify if the RS-D7, its analog and its prodrug improve the symptoms through the NMDA receptor.

Animals

All wild-type (WT) mice used in this study were backcrossed onto a C57BL/6J background from the Laboratory Animal Center of National Taiwan University Hospital, and all behavioral examinations were conducted in WT mice. For acclimatizing to laboratory conditions, the mice were allowed free access to food and water and were housed in groups with a 12 hours light-dark cycle in a temperature and humidity controlled room of the Psychology Department, National Taiwan University. All animals within the age of 3 months were housed individually one week before experiment testing with food and water available ad libitum. In the beginning of the experiments, the mice were handled and weighted daily at least 1 week before the behavioral experiments. The entire animal procedures were performed according to protocols approved by the Animal Care and Use Committee established by the National Taiwan University.

Drug Preparation for Treating Animals

MK-801 was dissolved in saline and administered at a volume of 0.01 ml/g body weight. RS-D7, Drug 12083 (analog of RS-D7) and was freshly dissolved in 1% CMC to the concentration of 2 mg/ml before usage. Prodrug 28095 was freshly dissolved in NMP:HP-beta-CD:H$_2$O (5:25:70) to the concentration of 2 mg/ml before usage. All animals were given vehicle (saline) or MK-801 (0.2 mg/kg, i.p.) 25 minutes before the behavioral experiments. Both vehicle (1% CMC or NMP:HP-beta-CD:H$_2$O) and experimental groups (RS-D7, Drug 12083 or Prodrug 28095) were treated after 5 minutes MK-801 administration with the appropriate dose via P.O. injections (at a volume of 0.01 ml/g body weight).

Behavioral Experiment Procedure

For investigating the treatment effect of RS-D7 for negative and cognitive symptoms, a series of three behavioral tests (run from the first to the third week), which included open field, sucrose preference test and prepulse inhibition were performed in sequence with a 1-week interval between tests.

Open Field

To assess spontaneous locomotor activity, each subject was placed into the center of an open-field apparatus (25.40*25.40*40.64 cm$^3$, Coulbourn Instruments, Whitehall, Pa., USA) under dim lighting condition (60 lx). Motor activity parameters (including total travel distance and travel distance per 10 minutes) were monitored and recorded over a 60 minutes period by using Smart video tracking software (Panlab, Harvard apparatus, US). For comparing the treatment effects of different treatment groups, the percentage change of rescue effect on MK-801-induced hyperlocomotion was calculated using the following formula: %=(rescue effect of drug−MK-801 effect)×100%/MK-801 effect.

Compared with the saline controls, mice exhibit the hyperlocomotion in the open field after acute MK-801 injection. The injection of 200 and 400 mg/kg RS-D7 rescued the MK-801 induced hyperlocomotion in mice. However, the 100 mg/kg RS-D7 did not display the treatment effect. This result suggests that acute RS-D7 injection normalized MK-801-induced hyperlocomotion as a positive symptom of schizophrenia in the open field test. Drug 12083 alleviated MK-801 induced hyperlocomotion deficits at 20 and 40 mg/kg dose. 100 mg/kg Prodrug 28095 alleviated MK-801 induced hyperlocomotion. In conclusion, compared to the MK-801 group, different dosages of RS-D7, Drug 12083 and Prodrug 28095 can rescue the MK-801-induced hyperlocomotion. The rescue effects of these drugs on MK-801 induced hyperlocomotion were indicated in FIG. 1.

Sucrose Preference Test

To assess the anhedonia, one of the negative symptoms of schizophrenia, all mice underwent 4-day testing. In the beginning of the sucrose preference, all mice were deprived of water for 23 hours in all the experiment from one day before the first day. On the first day, each mouse was given free access to 2 identical bottles with water for 1 hour. Then, the 2 identical bottles were replaced that one filled with 1% (wt/vol) sucrose solution and the other with water on the second day. On the third and fourth day, each mouse was received MK-801 and RS-D7 treatment before the experiment, and also free accessed to bottles for 1 hour. After the experiment, the 2 bottles were weighted to measure the 1-hour consumption of sucrose solution and water. The sucrose preference percentage (SPP) was calculated using the following formula: % SPP=sucrose solution consumption (g)×100%/[water consumption (g)+sucrose solution consumption (g)].

Figure 2:
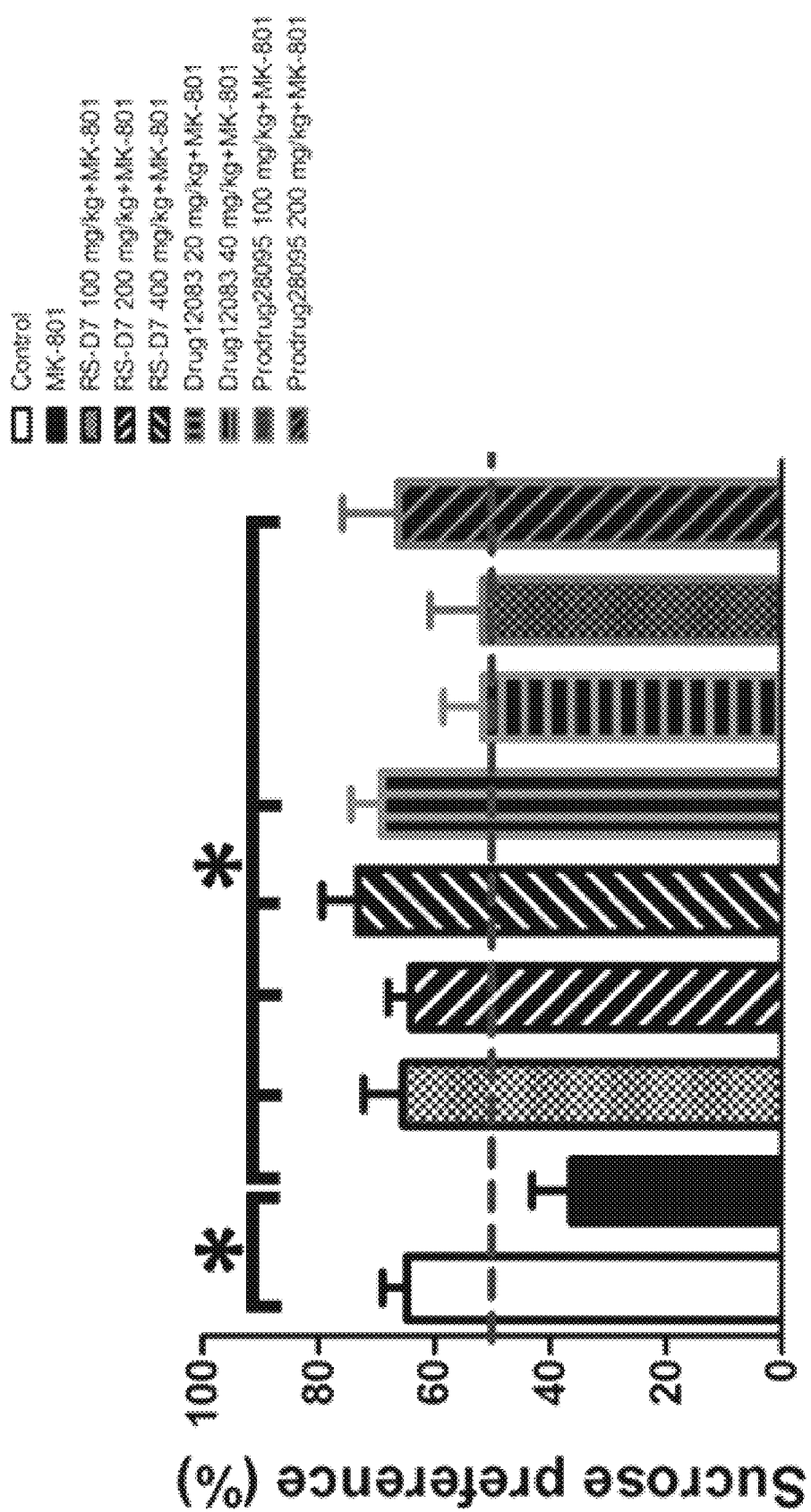
FIG. 2 shows that different dosages of RS-D7, Drug 12083 and Prodrug 28095 rescue the anhedonia after acute MK-801 injection.

Compared with the saline controls, a significant reduction of sucrose intake in the sucrose preference test was observed in testing mice after acute MK-801 injection. The injection of 100, 200 and 400 mg/kg RS-D7 rescued the MK-801 induced anhedonia deficit in mice. 20 mg/kg Drug 12083 and 200 mg/kg Prodrug 28095 also normalized MK-801 induced anhedonia. As a result, different dosages of RS-D7, Drug 12083 and Prodrug 28095 rescued the anhedonia after acute MK-801 injection. The rescue effects of these drugs on MK-801 induced anhedonia were indicated in FIG. 2.

Prepulse Inhibition

To assess the sensorimotor gating function, each mouse was tested with the SR-LAB startle apparatus (San Diego Instruments, San Diego, Calif., USA). The background noise was 72 dB during testing. Each session was initiated with a 5 minutes acclimatization period followed by 64 trials, consisting of pulse-alone (P-alone) trials, prepulse pulse (pp+P) trials, and no stimulation (nostim) trials. A P-alone trial was a 120 dB white noise burst of 40 msec. In the pp+P trials, the 120 dB pulse was preceded (by 100 msec) by a 20 msec of white noise prepulse burst of 78 dB (PP6), 82 dB (PP10), or 90 dB (PP18). The nostim trials consisted of background noise only. The session began and ended with a block of six presentations of the P-alone trial. Between these two blocks, the rest of the 52 trials were performed pseudorandomly and separated by intertrial intervals of 15 sec on average (varying between 10 and 20 sec). PPI was calculated as a percentage of the startle response using the formula: % PPI=100× [(P-alone score)-(pp+P score)]/(pulse-alone score), where the pulse-alone score was the average of the pulse-alone values from the in-between block of 52 trials.

Figure 3:
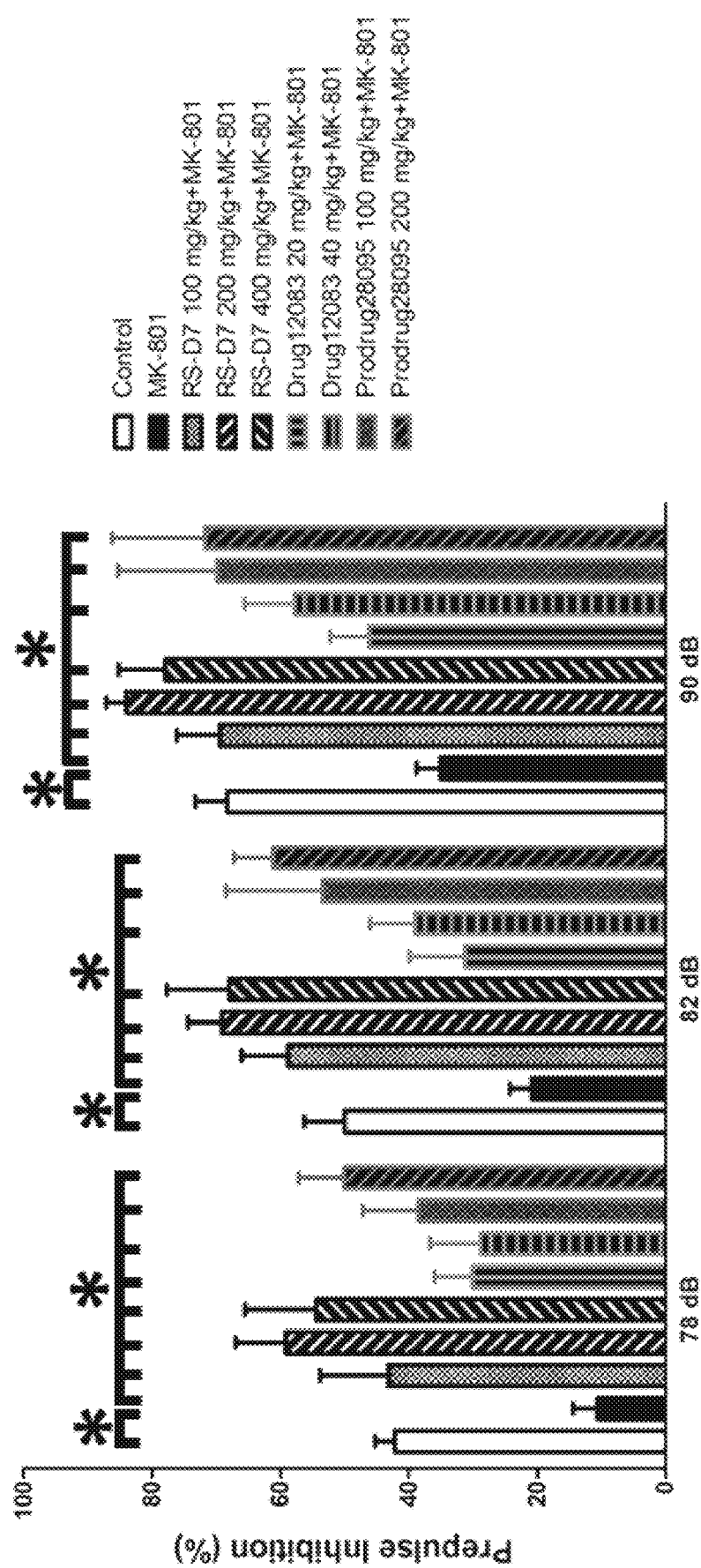
FIG. 3 shows a significant reduction of PPI after acute MK-801 injections.

Mice with acute MK-801 injection exhibited a profound reduction of acoustic PPI. However, the injection of 100, 200, and 400 mg/kg RS-D7, 20 and 40 mg/kg Drug 12083, and 100 and 200 mg/kg Prodrug 28095 significantly alleviated MK-801 induced PPI deficit in these mice. In other words, Mice displayed a significant reduction of PPI after acute MK-801 injections and they can be normalized by all dosages of RS-D7, Drug 12083 and Prodrug 28095. The recovery rates of MK-801 induced PPI deficit were indicated in FIG. 3.

What is claimed is:

1. A compound of formula (I),

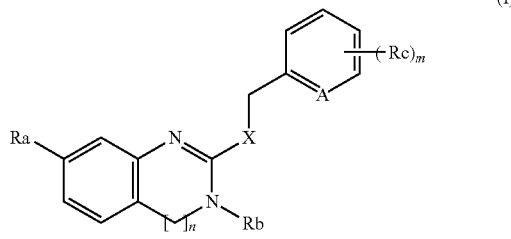

(I)

wherein n is 0,
X is —S(=O);
A is N;
$R_a$ is —O—C(=O)$R_{a3}$ or —O—C(=O)—T—O$R_{a4}$; wherein
  $R_{a3}$ is a linear or branched $C_{1-15}$alkyl, linear or branched $C_{2-15}$alkenyl, —T—$C_{3-10}$cycloalkyl, —T—NH$R_{a3p}$, —T—$C_{3-10}$cycloalkenyl, —T—$C_{6-10}$aryl, —T—$C_{5-10}$heteroaryl, —T—NH—C(=O)—O—$C_{1-10}$alkyl, —T—adamantyl or —$C_{1-3}$alkylene—$C_{6-10}$aryl where the alkylene is substituted with —T—NH$R_{a3p}$;
  $R_{a4}$ is a linear or branched $C_{1-15}$alkyl, linear or branched $C_{2-15}$alkenyl, —T—$C_{3-10}$cycloalkyl, —T—NH$R_{a3p}$, —T—$C_{3-10}$cycloalkenyl, —T—$C_{6-10}$aryl, —T—$C_{5-10}$heteroaryl, —T—NH—C(=O)—O-$C_{1-10}$alkyl, —T—adamantyl or —$C_{1-3}$alkylene—$C_{6-10}$aryl where the alkylene is substituted with —T—NH$R_{a3p}$;
  $R_{a3p}$ is H or an N-protecting group selected from Fmoc or Boc;
  $R_b$ is H, linear or branched $C_{1-15}$alkyl, linear or branched $C_{2-15}$alkenyl, $C_{1-3}$alkoxy—$C_{1-15}$alkyl—, —T'-$C_{3-10}$cycloalkyl, —T'—$C_{3-10}$cycloalkenyl, —T'—$C_{6-10}$aryl or —T'—$C_{5-10}$heteroaryl;
  $R_c$ each is independently halogen, linear or branched $C_{1-15}$alkyl, linear or branched $C_{1-15}$alkoxyl, hydroxyl group, or —$C_{1-10}$alkylene—Y—$C_{6-10}$heteroaryl wherein —Y— is —CH$_2$—, —NH—, —O— or —S—;
  m is an integer from 0 to 4;
  -T- is absent, $C_{1-3}$alkylene or $C_{2-3}$alkenylene;
  -T'- is $C_{1-3}$alkylene or $C_{2-3}$alkenylene; and
  wherein the heteroaryl contains at least one heteroatom, each heteroatom being independently S, N or O;
  wherein the alkyl, alkenyl, cycloalkyl, aryl, heteroaryl, alkylene and alkenylene are each independently unsubstituted or substituted with at least one substituent;
  wherein the substituent is each independently a halogen, nitro, nitroso, linear or branched $C_{1-15}$ alkyl, or linear or branched $C_{1-15}$ alkoxy or $C_{3-10}$cycloalkyl;
  wherein the alkoxy is unsubstituted; and
  when $R_b$ is H, the tautomers are included,
  or a pharmaceutically acceptable salt thereof.

2. The compound of claim 1, wherein
A is N;
$R_b$ is H;
m is 3; and
$R_c$ each is independently linear or branched $C_{1-15}$alkyl, linear or branched $C_{1-15}$alkoxyl;
or a pharmaceutically acceptable salt.

3. The compound of claim 1, wherein m is an integer from 0 to 3.

4. The compound of claim 1, wherein $R_a$ is —O—C(=O)$R_{a3}$ wherein $R_{a3}$ is adamantyl; linear or branched $C_{1-10}$alkyl unsubstituted or substituted by halogen; $C_{1-4}$alkoxy; —$C_{6-10}$aryl unsubstituted or substituted by $C_{1-10}$ alkyl, nitro, $C_{1-15}$alkoxy or halogen; $C_{3-10}$cycloalkyl; —$C_{3-10}$cycloalkenyl; linear or branched $C_{2-10}$alkenyl; —$C_{5-10}$heteroaryl; —$C_{1-3}$alkylene—$C_{3-10}$cycloalkyl; $C_{2-3}$alkenylene—$C_{6-10}$aryl wherein $C_{6-10}$aryl is unsubstituted or substituted by halogen; —O—C(=O)—O—$C_{1-10}$alkyl.

5. The compound of claim 1, wherein $R_a$ is —O—C(=O)$R_{a3}$ wherein $R_{a3}$ is adamantly adamantyl; linear or branched $C_{1-8}$alkyl unsubstituted or substituted by halogen; $C_{1-4}$alkoxy; -phenyl unsubstituted or substituted by $C_{1-6}$ alkyl, nitro, $C_{1-4}$alkoxy or halogen; $C_{3-6}$cycloalkyl; —$C_{3-6}$cycloalkenyl; linear or branched $C_{2-6}$alkenyl; —$C_{5-6}$heteroaryl; —$C_{1-3}$alkylene—$C_{3-6}$cycloalkyl; $C_{2-3}$alkenylene-phenyl wherein phenyl is unsubstituted or substituted by halogen; —O—C(=O)—O—$C_{1-4}$alkyl.

6. The compound of claim 1, wherein $R_a$ is —O—C(=O)—$C_{1-6}$alkyl, —O—C(=O)—$C_{1-3}$alkylene-NHFmoc, —O—C(=O)—$C_{1-3}$alkylene-NHBoc or —O—C(=O)—NH—C(=O)—O—$C_{1-10}$alkyl.

7. The compound of claim 1, wherein $R_c$ each is independently halogen, linear or branched $C_{1-6}$alkyl, linear or branched $C_{1-6}$alkoxyl, or —$C_{1-10}$alkenylene—Y—$C_{6-10}$heteroaryl; wherein Y is S and $C_{6-10}$heteroaryl is unsubstituted or substituted by $C_{1-15}$alkyl, $C_{1-15}$alkoxy, —OH, —NH$_2$, —NO$_2$ or halogen.

8. A compound of selected from the group consisting of:
21122: (2-(((4-methoxy-3,5-dimethylpyridin-2-yl)methyl)sulfinyl)-1H-benzo[d]imidazol-5-yl acetate),
21124: (2-(((4-methoxy-3,5-dimethylpyridin-2-yl)methyl)sulfinyl)-1H-benzo[d]imidazol-5-yl benzoate),
26096: (2-(((4-methoxy-3,5-dimethylpyridin-2-yl)methyl)sulfinyl)-1H-benzo[d]imidazol-5-yl butyrate), 26097: (2-(((4-methoxy-3,5-dimethylpyridin-2-yl)methyl)sulfinyl)-1H-benzo[d]imidazol-5-yl cyclohexanecarboxylate), 26098: (2-(((4-methoxy-3,5-dimethylpyridin-2-yl)methyl)sulfinyl)-1H-benzo[d]imidazol-5-yl 4-butylbenzoate), 21127: (2-(((4-methoxy-3,5-dimethylpyridin-2-yl)methyl)sulfinyl)-1H-benzo[d]imidazol-5-yl 3-methylbenzoate), 27076: 2-(((4-methoxy-3,5-dimethylpyridin-2-yl)methyl)sulfinyl)-1H-benzo[d]imidazol-5-yl hexanoate, 27077: 2-(((4-methoxy-3,5-dimethylpyridin-2-yl)methyl)sulfinyl)-1H-benzo[d]imidazol-5-yl isobutyrate, 27078: (2-(((4-methoxy-3,5-dimethylpyridin-2-yl)methyl)sulfinyl)-1H-benzo[d]imidazol-5-yl cyclohex-3-ene-1-carboxylate), 27079: 2-(((4-methoxy-3,5-dimethylpyridin-2-yl)methyl)sulfinyl)-1H-benzo[d]imidazol-5-yl cyclohex-3-enecarboxylate 28087: (2-(((4-methoxy-3,5-dimethylpyridin-2-yl)methyl)sulfinyl)-1H-benzo[d]imidazol-5-yl 4-methylbenzoate), 28091: (2-(((4-methoxy-3,5-dimethylpyridin-2-yl)methyl)sulfinyl)-1H-benzo[d]imidazol-5-yl 2-nitrobenzoate), 28092: (2-(((4-methoxy-3,5-dimethylpyridin-2-yl)methyl)sulfinyl)-1H-benzo[d]imidazol-5-yl cyclopropanecarboxylate), 28093: (2-(((4-methoxy-3,5-dimethylpyridin-2-yl)methyl)sulfinyl)-1H-benzo[d]imidazol-5-yl 2-ethylbutanoate), 28094: (2-(((4-methoxy-3,5-dimethylpyridin-2-yl)methyl)sulfinyl)-1H-benzo[d]imidazol-5-yl 2-phenylacetate), 28095: (2-(((4-methoxy-3,5-dimethylpyridin-2-yl)methyl)sulfinyl)-1H-benzo[d]imidazol-5-yl 3,5,5-trimethylhexanoate 28096: (2-(((5-methoxy-4,6-dimethylpyridin-2-yl)methyl)sulfinyl)-1H-benzo[d]imidazol-5-yl 2-ethoxybenzoate), 21123: (2-(((4-methoxy-3,5-dimethylpyridin-2-yl)methyl)sulfinyl)-1H-benzo[d]imidazol-5-yl propionate), 21125: (2-(((4-methoxy-3,5-dimethylpyridin-2-yl)methyl)sulfinyl)-1H-benzo[d]imidazol-5-yl 4-chlorobenzoate), 21126: (2-(((4-methoxy-3,5-dimethylpyridin-2-yl)methyl)sulfinyl)-1H-benzo[d]imidazol-5-yl 3-nitrobenzoate), 21128: 2-(((4-methoxy-3,5-dimethylpyridin-2-yl)methyl)sulfinyl)-1H-benzo[d]imidazol-5-yl heptanoate 21129: (2-(((4-methoxy-3,5-dimethylpyridin-2-yl)methyl)sulfinyl)-1H-benzo[d]imidazol-5-yl 4-fluorobenzoate), 21130: (2-(((4-methoxy-3,5-dimethylpyridin-2-yl)methyl)sulfinyl)-1H-benzo[d]imidazol-5-yl (Z)-2-methylbut-2-enoate), 21131: (2-(((4-methoxy-3,5-dimethylpyridin-2-yl)methyl)sulfinyl)-1H-benzo[d]imidazol-5-yl 2-chloropropanoate), 21132: tert-butyl (2-(((4-methoxy-3,5-dimethylpyridin-2-yl)methyl)sulfinyl)-1H-benzo[d]imidazol-5-yl) carbonate 12124: (2-(((4-methoxy-3,5-dimethylpyridin-2-yl)methyl)sulfinyl)-1H-benzo[d]imidazol-5-yl (Z)-but-2-enoate), 12125: (2-(((4-methoxy-3,5-dimethylpyridin-2-yl)methyl)sulfinyl)-1H-benzo[d]imidazol-5-yl 3-methylbut-2-enoate), 12122: (2-(((4-methoxy-3,5-dimethylpyridin-2-yl)methyl)sulfinyl)-1H-benzo[d]imidazol-5-yl furan-2-carboxylate), 12123: (2-(((4-methoxy-3,5-dimethylpyridin-2-yl)methyl)sulfinyl)-1H-benzo[d]imidazol-5-yl acrylate), 12127: (2-(((4-methoxy-3,5-dimethylpyridin-2-yl)methyl)sulfinyl)-1H-benzo[d]imidazol-5-yl 2-methylbutanoate), 12128: (2-(((4-methoxy-3,5-dimethylpyridin-2-yl)methyl)sulfinyl)-1H-benzo[d]imidazol-5-yl 3-cyclopentylpropanoate), 12129: (2-(((4-methoxy-3,5-dimethylpyridin-2-yl)methyl)sulfinyl)-1H-benzo[d]imidazol-5-yl (E)-3-(2-chlorophenyl)acrylate), 12130: (2-(((4-methoxy-3,5-dimethylpyridin-2-yl)methyl)sulfinyl)-1H-benzo[d]imidazol-5-yl 6-bromohexanoate), 11021: (2-(((4-methoxy-3,5-dimethylpyridin-2-yl)methyl)sulfinyl)-1H-benzo[d]imidazol-5-yl 2-fluorobenzoate), 11020: (2-(((4-methoxy-3,5-dimethylpyridin-2-yl)methyl)sulfinyl)-1H-benzo[d]imidazol-5-yl 4-methoxybenzoate), 11022: (2-(((4-methoxy-3,5-dimethylpyridin-2-yl)methyl)sulfinyl)-1H-benzo[d]imidazol-5-yl (3r,5r,7r)-adamantane-1-carboxylate)

11023: (2-(((4-methoxy-3,5-dimethylpyridin-2-yl)methyl)sulfinyl)-1H-benzo[d]imidazol-5-yl isoxazole-5-carboxylate), 11030: (2-(((4-methoxy-3,5-dimethylpyridin-2-yl)methyl)sulfinyl)-1H-benzo[d]imidazol-5-yl 4-(tert-butyl)benzoate), 11031: (2-(((4-methoxy-3,5-dimethylpyridin-2-yl)methyl)sulfinyl)-1H-benzo[d]imidazol-5-yl 3-chloro-4-fluorobenzoate), 25015: (2-(((4-methoxy-3,5-dimethylpyridin-2-yl)methyl)sulfinyl)-1H-benzo[d]imidazol-5-yl pivalate), 25016: (2-(((4-methoxy-3,5-dimethylpyridin-2-yl)methyl)sulfinyl)-1H-benzo[d]imidazol-5-yl pentanoate), 25017: (2-(((4-methoxy-3,5-dimethylpyridin-2-yl)methyl)sulfinyl)-1H-benzo[d]imidazol-5-yl 4-nitrobenzoate), 25027: (2-(((4-methoxy-3,5-dimethylpyridin-2-yl)methyl)sulfinyl)-1H-benzo[d]imidazol-5-yl cyclobutanecarboxylate), 25028: (2-(((4-methoxy-3,5-dimethylpyridin-2-yl)methyl)sulfinyl)-1H-benzo[d]imidazol-5-yl thiophene-2-carboxylate), 25029: (2-(((4-methoxy-3,5-dimethylpyridin-2-yl)methyl)sulfinyl)-1H-benzo[d]imidazol-5-yl 2-methylbutanoate), 25030: (2-(((4-methoxy-3,5-dimethylpyridin-2-yl)methyl)sulfinyl)-1H-benzo[d]imidazol-5-yl 3,3-dimethylbutanoate)

25031: (2-(((4-methoxy-3,5-dimethylpyridin-2-yl)methyl)sulfinyl)-1H-benzo[d]imidazol-5-yl 2-methoxyacetate), and 25032: (ethyl (2-(((4-methoxy-3,5-dimethylpyridin-2-yl)methyl)sulfinyl)-1H-benzo[d]imidazol-5-yl) carbonate), or a pharmaceutically acceptable salt thereof.

9. The compound

13001: 2-(((4-methoxy-3,5-dimethylpyridin-2-yl)methyl)sulfinyl)-1H-benzo[d]imidazol-6-yl 2-((tert-butoxycarbonyl)amino)acetate or a pharmaceutically acceptable salt thereof.

10. A pharmaceutical composition, comprising a compound of claim 1.

* * * * *